United States Patent
Terakawa et al.

(10) Patent No.: US 8,937,218 B2
(45) Date of Patent: Jan. 20, 2015

(54) TRANSFORMED SOYBEAN PLANT WHICH ACCUMULATES VACCINE, AND USE THEREOF

(75) Inventors: Teruhiko Terakawa, Atsugi (JP);
Hisakazu Hasegawa, Atsugi (JP);
Masao Ishimoto, Sapporo (JP); Shigeru Utsumi, Kyoto (JP); Yasuko Utsumi, legal representative, Kyoto (JP); Mikio Shoji, Hirosaki (JP); Takeshi Kawarabayashi, Hirosaki (JP)

(73) Assignee: Hokko Chemical Industry Co., Ltd., Chuo-Ku, Tokyo (JP)

( * ) Notice: Subject to any disclaimer, the term of this patent is extended or adjusted under 35 U.S.C. 154(b) by 595 days.

(21) Appl. No.: 13/130,465

(22) PCT Filed: Nov. 26, 2009

(86) PCT No.: PCT/JP2009/069977
§ 371 (c)(1),
(2), (4) Date: May 20, 2011

(87) PCT Pub. No.: WO2010/061899
PCT Pub. Date: Jun. 3, 2010

(65) Prior Publication Data
US 2011/0243975 A1    Oct. 6, 2011

(30) Foreign Application Priority Data
Nov. 28, 2008   (JP) ................. 2008-304006

(51) Int. Cl.
| | |
|---|---|
| C12N 15/62 | (2006.01) |
| A01H 5/00 | (2006.01) |
| A01H 5/10 | (2006.01) |
| A61K 38/00 | (2006.01) |
| A61K 38/08 | (2006.01) |
| A61P 25/28 | (2006.01) |
| C12N 15/82 | (2006.01) |
| C12N 5/04 | (2006.01) |
| C07K 7/06 | (2006.01) |
| A61K 36/48 | (2006.01) |
| C07K 16/18 | (2006.01) |
| A61K 39/00 | (2006.01) |

(52) U.S. Cl.
CPC ........ *C12N 15/8258* (2013.01); *C07K 2317/13* (2013.01); *C07K 2317/34* (2013.01); *C07K 16/18* (2013.01); *A61K 2039/517* (2013.01); *A61K 39/0005* (2013.01)
USPC ............ 800/288; 800/312; 800/278; 514/1.1; 514/17.8; 514/783; 435/69.1; 435/468; 435/415; 435/419; 435/320.1; 530/300; 424/184.1; 424/185.1

(58) Field of Classification Search
None
See application file for complete search history.

(56) References Cited

U.S. PATENT DOCUMENTS

| | | | |
|---|---|---|---|
| 6,576,820 B1 | 6/2003 | Takaiwa et al. | |
| 2003/0232758 A1* | 12/2003 | St. George-Hyslop et al. | 514/12 |
| 2007/0136896 A1 | 6/2007 | Takaiwa et al. | |
| 2007/0192905 A1* | 8/2007 | Piller et al. | 800/288 |
| 2007/0280953 A1* | 12/2007 | Rosenberg et al. | 424/184.1 |

FOREIGN PATENT DOCUMENTS

WO   WO 2006/093277   9/2006

OTHER PUBLICATIONS

Takagi et al (PNAS, 102(48), pp. 17525-17530, 2005).*
Youm et al (Biotechnol Lett., 30, pp. 1839-1845, 2008).*
Takaiwa et al (AAY80994, published Jun. 5, 2000).*
GenBank AB353075 (published 2007).*
Oono, et al. "Analysis of ER Stress in Developing Rice endosperm Accumulating β-amyloid Peptide," *Plant Biotechnology Journal*, vol. 8, No. 6, pp. 691-718, Mar. 15, 2010.
Extended European Search Report dated May 12, 2029, issued to the corresponding European patent application No. 09829144.6.
Adachi, et al. "Crystal Structure of Soybean Proglycinin A1aB1b Homotrimer," *Journal of Molecular Biology*, vol. 305, pp. 291-305, 2001.
Hasagawa, et al. "2-6 Technological Development of Soybean that Produces Highly Functional Substance," Preprints of Biotechnology Symposium, Nov. 6, 2008, 28th, pp. 87-88.
Manea, et al. "Polypeptide Conjugates Comprising a β-Amyloid Plaque-Specific Epitope as New Vaccine Structures Against Alzheimer's Disease," *Biopolymers*, vol. 76, pp. 503-511, 2004.
Takagi, et al. "A Rice-based Edible Vaccine Expressing Multiple T Cell Epitopes Induces Oral Tolerance for Inhibition of Th2-mediated IgE Responses," *Proceedings of the National Academy of Sciences USA*, vol. 102, No. 48, pp. 17525-17530, 2005.
Terakawa, et al. 3-6 Technological Development of Soybean that Produces Highly Functional Substance, Preprints of Biotechnology Symposium, Nov. 6, 2007, pp. 103-104.
Utsumi, et al. "Synthesis, Processing and Accumulation of Modified Glycinins of Soybean in the Seeds, Leaves and Stems of Transgenic Tobacco," *Plant Science*, vol. 92, pp. 191-202, 1993.

(Continued)

*Primary Examiner* — David T Fox
*Assistant Examiner* — Stephen Uyeno
(74) *Attorney, Agent, or Firm* — Knobbe, Martens, Olson & Bear LLP

(57) ABSTRACT

A transformed soybean plant having a gene encoding a modified seed storage protein introduced therein, obtained by inserting a gene encoding an Alzheimer's disease vaccine to a variable region(s) of a gene encoding a wild-type seed storage protein, is produced, and said vaccine is produced and accumulated in the seeds thereof.

36 Claims, 5 Drawing Sheets

(56) References Cited

OTHER PUBLICATIONS

Figure 2:
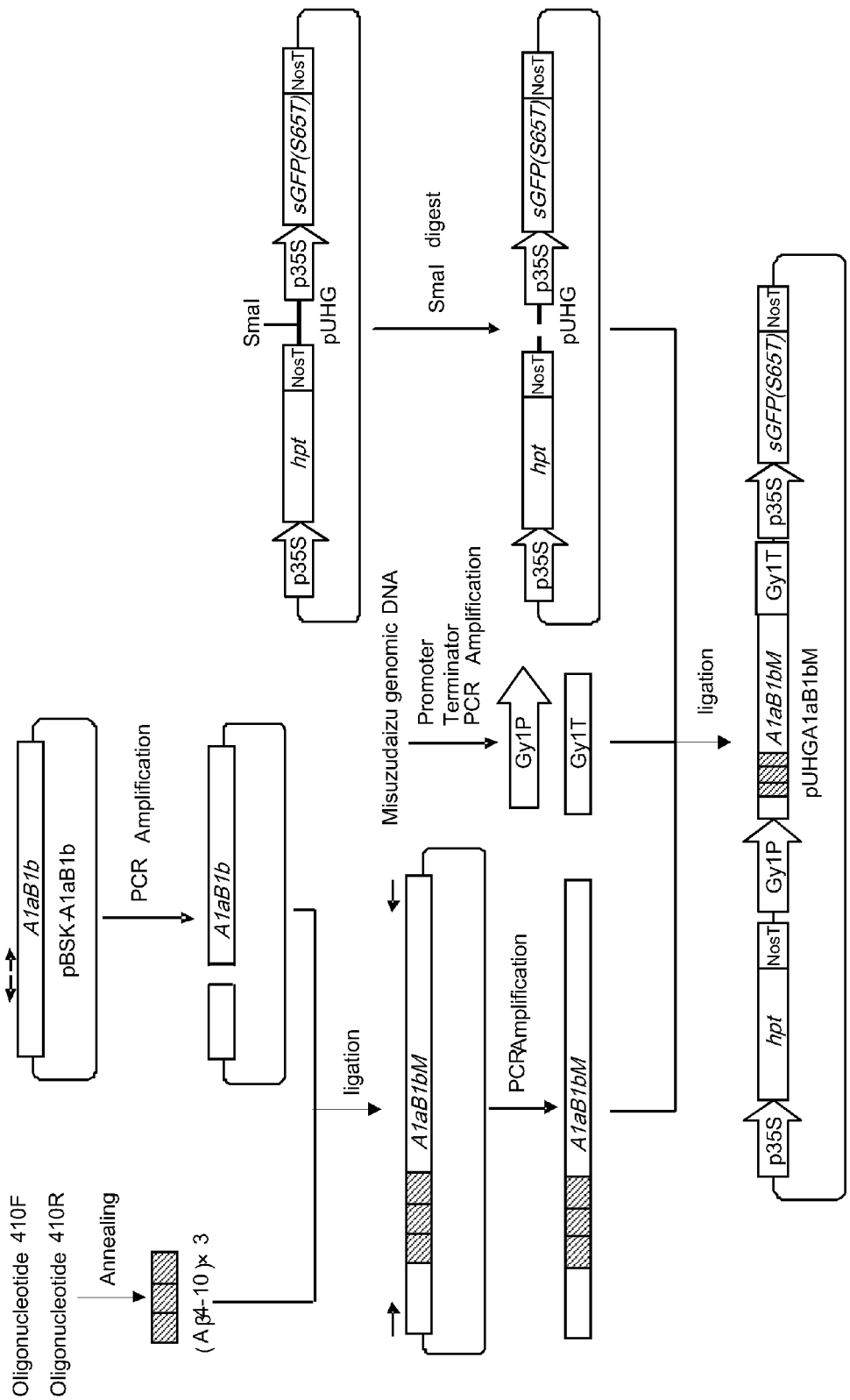

Utsumi, "X-ray Crystallography for Molecular Designing of Soybean Protein Having Enhanced/Given Functionality," The 3$^{rd}$ Result Report, pp. 69-70, 1995.

Youm, et al. "Transgenic Potato Expressing Aβ Reduce Aβ Burden in Alzheimer's Disease Mouse Model," *FEBS Letters*, vol. 579, pp. 6737-6744, 2005.

Youm, et al. "Transgenic Tomatoes Expressing Human Beta-amyloid for Use as a Vaccine Against Alzheimer's Disease," *Biotechnology Letters*, vol. 30, pp. 1839-1845, 2008.

International Search Report issued to international application No. PCT/JP2009/069977 dated Feb. 9, 2010.

Office Action issued in continuation-in-part application, U.S. Appl. No. 13/290,960, mailed on Apr. 25, 2014.

Kokjohn et al., "Amyloid precursor protein transgenic mouse models and Alzheimer's disease: Understanding the paradigms, limitations, and contributions", *Alzheimer's and Dementia*, vol. 5, pp. 340-347 (2009).

Office Action issued in corresponding Japanese Patent Application No. 2009-269231, mailed on May 7, 2014, with partial English translation.

Prak et al., "Design of genetically modified soybean proglycinin A1aB1b with multiple copies of bioactive peptide sequences," *Peptides*, vol. 27(6), pp. 1179-1186 (2006).

* cited by examiner

Fig. 1

MAKLVFSLCFLLFSGCCFAFSSREQPQQNECQIQKLNALKPDNRIESEGGLIETWNPNNK

Region II

PFQCAGVALSRCTLNRNALRRPSYTNGPQEIYIQQGKGIFGMIYPGCPST[FEEPQQPQQR]

[GQSSRPQD]RHQKIYNFREGDLIAVPTGVAWWMYNNEDTPVVAVSIIDTNSLENQLDQMPR

Region III

RFYLAGNQEQEFLKYQQ[EQGGHQSQKGKHQQEEENE]GGSILSGFTLEFLEHAFSVDKQIA

Region IV

KNLQGENEGEDKGAIVTVKGGLSVIKP[PTDEQQQRPQEEEEEEEDEKPQCKGKDKHCQRP]

[RGSQSKSRR]NGIDETICTMRLRHNIGQTSSPDIYNPQAGSVTTATSLDFPALSWLRLSAE

FGSLRKNAMFVPHYNLNANSIIYALNGRALIQVVNCNGERVFDGELQEGRVLIVPQNFVV

AARSQSDNFEYVSFKTNDTPMIGTLAGANSLLNALPEEVIQHTFNLKSQQARQIKNNNPF

Region V

KFLVPPQES[QKRAVA]                                        [Variable Region]

```
                          SEQUENCE LISTING

<160> NUMBER OF SEQ ID NOS: 61

<210> SEQ ID NO 1
<211> LENGTH: 1488
<212> TYPE: DNA
<213> ORGANISM: Glycine max
<220> FEATURE:
<221> NAME/KEY: CDS
<222> LOCATION: (1)..(1485)
<220> FEATURE:
<223> OTHER INFORMATION: A1aB1b

<400> SEQUENCE: 1 atg gcc aag cta gtt ttt tcc ctt tgt ttt ctg ctt ttc agt ggc tgc      48
Met Ala Lys Leu Val Phe Ser Leu Cys Phe Leu Leu Phe Ser Gly Cys
1               5                   10                  15 tgc ttc gct ttc agt tcc aga gag cag cct cag caa aac gag tgc cag      96
Cys Phe Ala Phe Ser Ser Arg Glu Gln Pro Gln Gln Asn Glu Cys Gln
                20                  25                  30 atc caa aaa ctc aat gcc ctc aaa ccg gat aac cgt ata gag tca gaa     144
Ile Gln Lys Leu Asn Ala Leu Lys Pro Asp Asn Arg Ile Glu Ser Glu
            35                  40                  45 gga ggg ctc att gag aca tgg aac cct aac aac aag cca ttc cag tgt     192
Gly Gly Leu Ile Glu Thr Trp Asn Pro Asn Asn Lys Pro Phe Gln Cys
        50                  55                  60 gcc ggt gtt gcc ctc tct cgc tgc acc ctc aac cgc aac gcc ctt cgt     240
Ala Gly Val Ala Leu Ser Arg Cys Thr Leu Asn Arg Asn Ala Leu Arg
65                  70                  75                  80 aga cct tcc tac acc aac ggt ccc cag gaa atc tac atc caa caa ggt     288
Arg Pro Ser Tyr Thr Asn Gly Pro Gln Glu Ile Tyr Ile Gln Gln Gly
                85                  90                  95 aag ggt att ttt ggc atg ata tac ccg ggt tgt cct agc aca ttt gaa     336
Lys Gly Ile Phe Gly Met Ile Tyr Pro Gly Cys Pro Ser Thr Phe Glu
                100                 105                 110 gag cct caa caa cct caa caa aga gga caa agc agc aga cca caa gac     384
Glu Pro Gln Gln Pro Gln Gln Arg Gly Gln Ser Ser Arg Pro Gln Asp
            115                 120                 125 cgt cac cag aag atc tat aac ttc aga gag ggt gat ttg atc gca gtg     432
Arg His Gln Lys Ile Tyr Asn Phe Arg Glu Gly Asp Leu Ile Ala Val
        130                 135                 140 cct act ggt gtt gca tgg tgg atg tac aac aat gaa gac act cct gtt     480
Pro Thr Gly Val Ala Trp Trp Met Tyr Asn Asn Glu Asp Thr Pro Val
145                 150                 155                 160 gtt gcc gtt tct att att gac acc aac agc ttg gag aac cag ctc gac     528
```

```
                Val Ala Val Ser Ile Ile Asp Thr Asn Ser Leu Glu Asn Gln Leu Asp
                                165                 170                 175 cag atg cct agg aga ttc tat ctt gct ggg aac caa gag caa gag ttt         576
Gln Met Pro Arg Arg Phe Tyr Leu Ala Gly Asn Gln Glu Gln Glu Phe
        180                 185                 190 cta aaa tat cag caa gag caa gga ggt cat caa agc cag aaa gga aag         624
Leu Lys Tyr Gln Gln Glu Gln Gly Gly His Gln Ser Gln Lys Gly Lys
            195                 200                 205 cat cag caa gaa gaa gaa aac gaa gga ggc agc ata ttg agt ggc ttc         672
His Gln Gln Glu Glu Glu Asn Glu Gly Gly Ser Ile Leu Ser Gly Phe
    210                 215                 220 acc ctg gaa ttc ttg gaa cat gca ttc agc gtg gac aag cag ata gcg         720
Thr Leu Glu Phe Leu Glu His Ala Phe Ser Val Asp Lys Gln Ile Ala
225                 230                 235                 240 aaa aac cta caa gga gag aac gaa ggg gaa gac aag gga gcc att gtg         768
Lys Asn Leu Gln Gly Glu Asn Glu Gly Glu Asp Lys Gly Ala Ile Val
                245                 250                 255 aca gtg aaa gga ggt ctg agc gtg ata aaa cca ccc acg gac gag cag         816
Thr Val Lys Gly Gly Leu Ser Val Ile Lys Pro Pro Thr Asp Glu Gln
            260                 265                 270 caa caa aga ccc cag gaa gag gaa gaa gaa gag gat gag aag cca             864
Gln Gln Arg Pro Gln Glu Glu Glu Glu Glu Asp Glu Lys Pro
    275                 280                 285 cag tgc aag ggt aaa gac aaa cac tgc caa cgc ccc cga gga agc caa         912
Gln Cys Lys Gly Lys Asp Lys His Cys Gln Arg Pro Arg Gly Ser Gln
290                 295                 300 agc aaa agc aga aga aat ggc att gac gag acc ata tgc acc atg aga         960
Ser Lys Ser Arg Arg Asn Gly Ile Asp Glu Thr Ile Cys Thr Met Arg
305                 310                 315                 320 ctt cgc cac aac att ggc cag act tca tca cct gac atc tac aac cct        1008
Leu Arg His Asn Ile Gly Gln Thr Ser Ser Pro Asp Ile Tyr Asn Pro
                325                 330                 335 caa gcc ggt agc gtc aca acc gcc acc agc ctt gac ttc cca gcc ctc        1056
Gln Ala Gly Ser Val Thr Thr Ala Thr Ser Leu Asp Phe Pro Ala Leu
            340                 345                 350 tcg tgg ctc aga ctc agt gct gag ttt gga tct ctc cgc aag aat gca        1104
Ser Trp Leu Arg Leu Ser Ala Glu Phe Gly Ser Leu Arg Lys Asn Ala
        355                 360                 365 atg ttc gtg cca cac tac aac ctg aac gcg aac agc ata ata tac gca        1152
Met Phe Val Pro His Tyr Asn Leu Asn Ala Asn Ser Ile Ile Tyr Ala
    370                 375                 380 ttg aat gga cgg gca ttg ata caa gtg gtg aat tgc aac ggt gag aga        1200
Leu Asn Gly Arg Ala Leu Ile Gln Val Val Asn Cys Asn Gly Glu Arg
385                 390                 395                 400 gtg ttt gat gga gag ctg caa gag gga cgg gtg ctg atc gtg cca caa        1248
Val Phe Asp Gly Glu Leu Gln Glu Gly Arg Val Leu Ile Val Pro Gln
                405                 410                 415 aac ttt gtg gtg gct gca aga tca cag agt gac aac ttc gag tat gtg        1296
Asn Phe Val Val Ala Ala Arg Ser Gln Ser Asp Asn Phe Glu Tyr Val
            420                 425                 430 tca ttc aag acc aat gat aca ccc atg atc ggc act ctt gca ggg gca        1344
Ser Phe Lys Thr Asn Asp Thr Pro Met Ile Gly Thr Leu Ala Gly Ala
        435                 440                 445 aac tca ttg ttg aac gca tta cca gag gaa gtg att cag cac act ttc        1392
Asn Ser Leu Leu Asn Ala Leu Pro Glu Glu Val Ile Gln His Thr Phe
    450                 455                 460 aac cta aaa agc cag cag gcc agg cag ata aag aac aac aac cct ttc        1440
Asn Leu Lys Ser Gln Gln Ala Arg Gln Ile Lys Asn Asn Asn Pro Phe
465                 470                 475                 480
```

```
aag ttc ctg gtt cca cct cag gag tct cag aag aga gct gtg gct tag    1488
Lys Phe Leu Val Pro Pro Gln Glu Ser Gln Lys Arg Ala Val Ala
                485                 490                 495
```

<210> SEQ ID NO 2
<211> LENGTH: 495
<212> TYPE: PRT
<213> ORGANISM: Glycine max
<220> FEATURE:
<223> OTHER INFORMATION: A1aB1b

<400> SEQUENCE: 2

```
Met Ala Lys Leu Val Phe Ser Leu Cys Phe Leu Leu Phe Ser Gly Cys
1               5                   10                  15

Cys Phe Ala Phe Ser Ser Arg Glu Gln Pro Gln Gln Asn Glu Cys Gln
            20                  25                  30

Ile Gln Lys Leu Asn Ala Leu Lys Pro Asp Asn Arg Ile Glu Ser Glu
        35                  40                  45

Gly Gly Leu Ile Glu Thr Trp Asn Pro Asn Asn Lys Pro Phe Gln Cys
50                  55                  60

Ala Gly Val Ala Leu Ser Arg Cys Thr Leu Asn Arg Asn Ala Leu Arg
65                  70                  75                  80

Arg Pro Ser Tyr Thr Asn Gly Pro Gln Glu Ile Tyr Ile Gln Gln Gly
                85                  90                  95

Lys Gly Ile Phe Gly Met Ile Tyr Pro Gly Cys Pro Ser Thr Phe Glu
            100                 105                 110

Glu Pro Gln Gln Pro Gln Gln Arg Gly Gln Ser Ser Arg Pro Gln Asp
        115                 120                 125

Arg His Gln Lys Ile Tyr Asn Phe Arg Glu Gly Asp Leu Ile Ala Val
130                 135                 140

Pro Thr Gly Val Ala Trp Trp Met Tyr Asn Asn Glu Asp Thr Pro Val
145                 150                 155                 160

Val Ala Val Ser Ile Ile Asp Thr Asn Ser Leu Glu Asn Gln Leu Asp
                165                 170                 175

Gln Met Pro Arg Arg Phe Tyr Leu Ala Gly Asn Gln Glu Gln Glu Phe
            180                 185                 190

Leu Lys Tyr Gln Gln Glu Gln Gly Gly His Gln Ser Gln Lys Gly Lys
        195                 200                 205

His Gln Gln Glu Glu Glu Asn Glu Gly Gly Ser Ile Leu Ser Gly Phe
210                 215                 220

Thr Leu Glu Phe Leu Glu His Ala Phe Ser Val Asp Lys Gln Ile Ala
225                 230                 235                 240

Lys Asn Leu Gln Gly Glu Asn Glu Gly Glu Asp Lys Gly Ala Ile Val
                245                 250                 255

Thr Val Lys Gly Gly Leu Ser Val Ile Lys Pro Pro Thr Asp Glu Gln
            260                 265                 270

Gln Gln Arg Pro Gln Glu Glu Glu Glu Glu Asp Glu Lys Pro
        275                 280                 285

Gln Cys Lys Gly Lys Asp Lys His Cys Gln Arg Pro Arg Gly Ser Gln
290                 295                 300

Ser Lys Ser Arg Arg Asn Gly Ile Asp Glu Thr Ile Cys Thr Met Arg
305                 310                 315                 320

Leu Arg His Asn Ile Gly Gln Thr Ser Ser Pro Asp Ile Tyr Asn Pro
                325                 330                 335

Gln Ala Gly Ser Val Thr Thr Ala Thr Ser Leu Asp Phe Pro Ala Leu
            340                 345                 350
```

```
Ser Trp Leu Arg Leu Ser Ala Glu Phe Gly Ser Leu Arg Lys Asn Ala
        355                 360                 365

Met Phe Val Pro His Tyr Asn Leu Asn Ala Asn Ser Ile Ile Tyr Ala
    370                 375                 380

Leu Asn Gly Arg Ala Leu Ile Gln Val Val Asn Cys Asn Gly Glu Arg
385                 390                 395                 400

Val Phe Asp Gly Glu Leu Gln Glu Gly Arg Val Leu Ile Val Pro Gln
                405                 410                 415

Asn Phe Val Val Ala Ala Arg Ser Gln Ser Asp Asn Phe Glu Tyr Val
            420                 425                 430

Ser Phe Lys Thr Asn Asp Thr Pro Met Ile Gly Thr Leu Ala Gly Ala
        435                 440                 445

Asn Ser Leu Leu Asn Ala Leu Pro Glu Glu Val Ile Gln His Thr Phe
    450                 455                 460

Asn Leu Lys Ser Gln Gln Ala Arg Gln Ile Lys Asn Asn Pro Phe
465                 470                 475                 480

Lys Phe Leu Val Pro Pro Gln Glu Ser Gln Lys Arg Ala Val Ala
                485                 490                 495

<210> SEQ ID NO 3
<211> LENGTH: 7
<212> TYPE: PRT
<213> ORGANISM: Homo sapiens
<220> FEATURE:
<221> NAME/KEY: PEPTIDE
<222> LOCATION: (1)..(7)
<220> FEATURE:
<223> OTHER INFORMATION: Abeta4-10

<400> SEQUENCE: 3

Phe Arg His Asp Ser Gly Tyr
1               5

<210> SEQ ID NO 4
<211> LENGTH: 63
<212> TYPE: DNA
<213> ORGANISM: Artificial Sequence
<220> FEATURE:
<223> OTHER INFORMATION: 410F

<400> SEQUENCE: 4
tttagacatg attctggtta tttcagacac gatagcggct acttcaggca tgactcagga    60
tat                                                                 63

<210> SEQ ID NO 5
<211> LENGTH: 63
<212> TYPE: DNA
<213> ORGANISM: Artificial Sequence
<220> FEATURE:
<223> OTHER INFORMATION: 410R

<400> SEQUENCE: 5
atatcctgag tcatgcctga agtagccgct atcgtgtctg aaataaccag aatcatgtct    60
aaa                                                                 63

<210> SEQ ID NO 6
<211> LENGTH: 27
<212> TYPE: DNA
<213> ORGANISM: Artificial Sequence
<220> FEATURE:
<223> OTHER INFORMATION: Primer
```

```
<400> SEQUENCE: 6
gcacaaagca gcagaccaca agaccgt                                              27

<210> SEQ ID NO 7
<211> LENGTH: 24
<212> TYPE: DNA
<213> ORGANISM: Artificial Sequence
<220> FEATURE:
<223> OTHER INFORMATION: Primer

<400> SEQUENCE: 7
tctttgttga ggttgttgag gctc                                                 24

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
gcccagaaag gaaagcatca g                                                    21

<210> SEQ ID NO 9
<211> LENGTH: 24
<212> TYPE: DNA
<213> ORGANISM: Artificial Sequence
<220> FEATURE:
<223> OTHER INFORMATION: Primer

<400> SEQUENCE: 9
ttgatgacct ccttgctctt gctg                                                 24

<210> SEQ ID NO 10
<211> LENGTH: 27
<212> TYPE: DNA
<213> ORGANISM: Artificial Sequence
<220> FEATURE:
<223> OTHER INFORMATION: Primer

<400> SEQUENCE: 10
gcccaggaag aggaagaaga agaagag                                              27

<210> SEQ ID NO 11
<211> LENGTH: 24
<212> TYPE: DNA
<213> ORGANISM: Artificial Sequence
<220> FEATURE:
<223> OTHER INFORMATION: Primer

<400> SEQUENCE: 11
tctttgttgc tgctcgtccg tggg                                                 24

<210> SEQ ID NO 12
<211> LENGTH: 27
<212> TYPE: DNA
<213> ORGANISM: Artificial Sequence
<220> FEATURE:
<223> OTHER INFORMATION: Primer

<400> SEQUENCE: 12
gcccgaggaa gccaaagcaa aagcaga                                              27

<210> SEQ ID NO 13
```

```
<211> LENGTH: 24
<212> TYPE: DNA
<213> ORGANISM: Artificial Sequence
<220> FEATURE:
<223> OTHER INFORMATION: Primer

<400> SEQUENCE: 13
gcgttggcag tgtttgtctt tacc                                            24

<210> SEQ ID NO 14
<211> LENGTH: 27
<212> TYPE: DNA
<213> ORGANISM: Artificial Sequence
<220> FEATURE:
<223> OTHER INFORMATION: Primer

<400> SEQUENCE: 14 tagggctgc aggaattcga tatcaag                                          27

<210> SEQ ID NO 15
<211> LENGTH: 27
<212> TYPE: DNA
<213> ORGANISM: Artificial Sequence
<220> FEATURE:
<223> OTHER INFORMATION: Primer

<400> SEQUENCE: 15
ttgagccaca gctctcttct gagactc                                         27

<210> SEQ ID NO 16
<211> LENGTH: 19
<212> TYPE: DNA
<213> ORGANISM: Artificial Sequence
<220> FEATURE:
<223> OTHER INFORMATION: Primer

<400> SEQUENCE: 16
ttggtgatat tgatgatgc                                                  19

<210> SEQ ID NO 17
<211> LENGTH: 25
<212> TYPE: DNA
<213> ORGANISM: Artificial Sequence
<220> FEATURE:
<223> OTHER INFORMATION: Primer

<400> SEQUENCE: 17
ggtgatgact gatgagtgtt taagg                                           25

<210> SEQ ID NO 18
<211> LENGTH: 2202
<212> TYPE: DNA
<213> ORGANISM: Glycine max
<220> FEATURE:
<221> NAME/KEY: Promoter
<220> FEATURE:
<223> OTHER INFORMATION: A1aB1b

<400> SEQUENCE: 18
cttggtgata ttgatgatgc attggactct gaaaaaggta acgttcttca cattattaac     60
tgattggagt attatttgtc attttggcct tgttcttatc gtaatattac tgcattgtat    120
ctacaagttg catagcaagt aaatctacaa gttgcatagc aagcaataat ttactttgtg    180
cagctgttgg agaactactc tcacatttta tctgaccaag tacccggct ctgcgagtcc     240 taaatgtaca aaactcagtt gcagggtcca cattagaggt taccttgcaa atgtggatag    300
```

```
taccttcctt cccttagcac gtgctggagt gagtttatca cgtagctagg tttgtcagat      360
tgggcttaga gtgatgaaca ttcaccaatc accagtttct tgattcaagt tgcagagcat      420
ggagtgatga agattgaacc acgcaagggt gactacaagt tatatattct cacttttta      480 aaatttagct cataattagt taacaatata tatagtgcta tatatttctt ctctcaataa      540
acaatgtagt actataatgg aataagaaac ttgaaatatg tagaacaata tatagctcca      600
tcattaagca agaaaagggt ttttgattg gacaaaattt aaatatagtt cttaacatgc       660
tgtttgtcat gttctgttat tagaattgaa atttatctca agatttgtac taaaaaaaaa      720
tatgtagatt aaattaaact ccaatttta ttggagaaca atacaaacaa cacttaaaac       780
ctgtaattaa ttttcttct tttaaaagt ggttcaacaa cacaagcttc aagttttaaa        840
aggaaaaatg tcagccaaaa actttaaata aaatggtaac aaggaaatta ttcaaaaatt      900
acaaacctcg tcaaatagg aaagaaaaaa agtttaggga tttagaaaaa acatcaatct       960
agttccacct tattttatag agaagaaa ctaatatata agaactaaaa aacagaagaa        1020
tagaaaaaaa aagtattgac aggaaagaaa aagtagctgt atgcttataa gtactttgag     1080
gatttgaatt ctctcttata aaacacaaac acaatttta gattttattt aaataatcat      1140
caatccgatt ataattattt atatatttt ctattttcaa agaagtaaat catgagcttt      1200
tccaactcaa catctatttt ttttctctca acctttttca catcttaagt agtctcaccc     1260
tttatatata taacttattt cttaccttt acattatgta acttttatca ccaaaaccaa      1320
caactttaaa attttattaa atagactcca caagtaactt gacactctta cattcatcga     1380
cattaacttt tatctgtttt ataaatatta ttgtgatata atttaatcaa aataaccaca     1440
aactttcata aaaggttctt attaagcatg gcatttaata agcaaaaaca actcaatcac     1500
tttcatatag gaggtagcct aagtacgtac tcaaaatgcc aacaaataaa aaaaaagttg     1560
ctttaataat gccaaaacaa attaataaaa cacttacaac accggatttt ttttaattaa     1620
aatgtgccat ttaggataaa tagttaatat ttttaataat tatttaaaaa gccgtatcta     1680
ctaaaatgat ttttatttgg ttgaaaatat taatatgttt aaatcaacac aatctatcaa     1740
aattaaacta aaaaaaaat aagtgtacgt ggttaacatt agtacagtaa tataagagga     1800
aaatgagaaa ttaagaaatt gaaagcgagt ctaattttta aattatgaac ctgcatatat     1860
aaaaggaaag aaagaatcca ggaagaaaag aaatgaaacc atgcatggtc ccctcgtcat    1920
cacgagtttc tgccatttgc aatagaaaca ctgaaacacc tttctctttg tcacttaatt    1980
gagatgccga agccacctca caccatgaac ttcatgaggt gtagcaccca aggcttccat    2040
agccatgcat actgaagaat gtctcaagct cagcacccta cttctgtgac gtgtccctca    2100
ttcaccttcc tctcttccct ataaataacc acgcctcagg ttctccgctt cacaactcaa    2160
acattctctc cattggtcct taaacactca tcagtcatca cc                        2202
```

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
agcccttttt gtatgtgcta c      21

<210> SEQ ID NO 20

-continued

```
<211> LENGTH: 20
<212> TYPE: DNA
<213> ORGANISM: Artificial Sequence
<220> FEATURE:
<223> OTHER INFORMATION: Primer

<400> SEQUENCE: 20
atacttaatg tttctcacct                                                 20

<210> SEQ ID NO 21
<211> LENGTH: 1052
<212> TYPE: DNA
<213> ORGANISM: Glycine max
<220> FEATURE:
<223> OTHER INFORMATION: Terminator
<220> FEATURE:
<223> OTHER INFORMATION: A1aB1b

<400> SEQUENCE: 21
agcccttttt gtatggatcc agcccttttt gtatgtgcta ccccacttttt gtcttttttgg    60 caatagtgct agcaaccaat aaataataat aataataatg aataagaaaa caaaggcttt    120
agcttgcctt tgttcactg taaaataata atgtaagtac tctctataat gagtcacgaa     180
acttttgcgg gaataaaagg agaaattcca atgagttttc tgtcaaatct tcttttgtct    240
ctctctctct ctcttttttt tttctttctt ctgagcttct tgcaaaacaa aaggcaaaca    300
ataacgattg gtccaatgat agttagcttg atcgatgata tctttaggaa gtgttggcag    360
gacaggacat gatgtagaag actaaaattg aaagtattgc agacccaata gttgaagatt    420
aactttaaga atgaagacgt cttatcaggt tcttcatgac ttggagctca acccaacttg    480
gaaagttcga gagtatttgg accattgtgc tttgtgtctt caaacataaa acatcgctcc    540
aaatttaaca tgggagctaa aaaatgtgtt tttctgggat tttaattttc aacagagtca    600
aggatggtgt tgcatatgat gtcttgatgt ccattgtcca cactaaatag atattggttt    660
caagaaatat taatttcatt ttcatgactt tcaattcata aaccttaaac gaatattaat    720
ttaaaatcta tcctcaaatg ataaatttta aaaaaaatta cccccaatcg gtaatttgac    780
tcacaagtta gttagttgat attttgaagc ttgaaattcg acatggacat cagacacaat    840
atgagcacag acactctcgc atagctaatg tgtaaaacat agaatgacag acatcacat    900 atatttttac acacacaaaa aaagaactct aataaaaaaa tatgtgtagc ttaacaaata    960
tataaattga tggtaaataa tttacttttt aaaattcatc tatgtttttt tatatgataa   1020
caaacataaa aaaggtgaga aacattaagt at                                 1052

<210> SEQ ID NO 22
<211> LENGTH: 1551
<212> TYPE: DNA
<213> ORGANISM: Glycine max
<220> FEATURE:
<221> NAME/KEY: CDS
<222> LOCATION: (1)..(1548)
<220> FEATURE:
<223> OTHER INFORMATION: A1aB1bM2

<400> SEQUENCE: 22 atg gcc aag cta gtt ttt tcc ctt tgt ttt ctg ctt ttc agt ggc tgc       48
Met Ala Lys Leu Val Phe Ser Leu Cys Phe Leu Leu Phe Ser Gly Cys
1               5                   10                  15 tgc ttc gct ttc agt tcc aga gag cag cct cag caa aac gag tgc cag       96
Cys Phe Ala Phe Ser Ser Arg Glu Gln Pro Gln Gln Asn Glu Cys Gln
            20                  25                  30
```

-continued

| | |
|---|---|
| atc caa aaa ctc aat gcc ctc aaa ccg gat aac cgt ata gag tca gaa<br>Ile Gln Lys Leu Asn Ala Leu Lys Pro Asp Asn Arg Ile Glu Ser Glu<br>         35                     40                     45 | 144 |
| gga ggg ctc att gag aca tgg aac cct aac aac aag cca ttc cag tgt<br>Gly Gly Leu Ile Glu Thr Trp Asn Pro Asn Asn Lys Pro Phe Gln Cys<br> 50                      55                       60 | 192 |
| gcc ggt gtt gcc ctc tct cgc tgc acc ctc aac cgc aac gcc ctt cgt<br>Ala Gly Val Ala Leu Ser Arg Cys Thr Leu Asn Arg Asn Ala Leu Arg<br>65                    70                       75                     80 | 240 |
| aga cct tcc tac acc aac ggt ccc cag gaa atc tac atc caa caa ggt<br>Arg Pro Ser Tyr Thr Asn Gly Pro Gln Glu Ile Tyr Ile Gln Gln Gly<br>                  85                       90                     95 | 288 |
| aag ggt att ttt ggc atg ata tac ccg ggt tgt cct agc aca ttt gaa<br>Lys Gly Ile Phe Gly Met Ile Tyr Pro Gly Cys Pro Ser Thr Phe Glu<br>               100                   105                 110 | 336 |
| gag cct caa caa cct caa caa aga ttt aga cat gat tct ggt tat ttc<br>Glu Pro Gln Gln Pro Gln Gln Arg Phe Arg His Asp Ser Gly Tyr Phe<br>           115                   120                 125 | 384 |
| aga cac gat agc ggc tac ttc agg cat gac tca gga tat gca caa agc<br>Arg His Asp Ser Gly Tyr Phe Arg His Asp Ser Gly Tyr Ala Gln Ser<br>130                   135                     140 | 432 |
| agc aga cca caa gac cgt cac cag aag atc tat aac ttc aga gag ggt<br>Ser Arg Pro Gln Asp Arg His Gln Lys Ile Tyr Asn Phe Arg Glu Gly<br>145                   150                     155                 160 | 480 |
| gat ttg atc gca gtg cct act ggt gtt gca tgg tgg atg tac aac aat<br>Asp Leu Ile Ala Val Pro Thr Gly Val Ala Trp Trp Met Tyr Asn Asn<br>               165                   170                 175 | 528 |
| gaa gac act cct gtt gtt gcc gtt tct att att gac acc aac agc ttg<br>Glu Asp Thr Pro Val Val Ala Val Ser Ile Ile Asp Thr Asn Ser Leu<br>             180                   185                 190 | 576 |
| gag aac cag ctc gac cag atg cct agg aga ttc tat ctt gct ggg aac<br>Glu Asn Gln Leu Asp Gln Met Pro Arg Arg Phe Tyr Leu Ala Gly Asn<br>           195                   200                 205 | 624 |
| caa gag caa gag ttt cta aaa tat cag caa gag caa gga ggt cat caa<br>Gln Glu Gln Glu Phe Leu Lys Tyr Gln Gln Glu Gln Gly Gly His Gln<br>210                   215                     220 | 672 |
| agc cag aaa gga aag cat cag caa gaa gaa gaa aac gaa gga ggc agc<br>Ser Gln Lys Gly Lys His Gln Gln Glu Glu Glu Asn Glu Gly Gly Ser<br>225                   230                     235                 240 | 720 |
| ata ttg agt ggc ttc acc ctg gaa ttc ttg gaa cat gca ttc agc gtg<br>Ile Leu Ser Gly Phe Thr Leu Glu Phe Leu Glu His Ala Phe Ser Val<br>             245                   250                 255 | 768 |
| gac aag cag ata gcg aaa aac cta caa gga gag aac gaa ggg gaa gac<br>Asp Lys Gln Ile Ala Lys Asn Leu Gln Gly Glu Asn Glu Gly Glu Asp<br>           260                   265                 270 | 816 |
| aag gga gcc att gtg aca gtg aaa gga ggt ctg agc gtg ata aaa cca<br>Lys Gly Ala Ile Val Thr Val Lys Gly Gly Leu Ser Val Ile Lys Pro<br>275                   280                     285 | 864 |
| ccc acg gac gag cag caa caa aga ccc cag gaa gag gaa gaa gaa<br>Pro Thr Asp Glu Gln Gln Gln Arg Pro Gln Glu Glu Glu Glu Glu<br>           290                   295                 300 | 912 |
| gag gat gag aag cca cag tgc aag ggt aaa gac aaa cac tgc caa cgc<br>Glu Asp Glu Lys Pro Gln Cys Lys Gly Lys Asp Lys His Cys Gln Arg<br>305                   310                     315                 320 | 960 |
| ccc cga gga agc caa agc aaa agc aga aga aat ggc att gac gag acc<br>Pro Arg Gly Ser Gln Ser Lys Ser Arg Arg Asn Gly Ile Asp Glu Thr<br>             325                   330                 335 | 1008 |
| ata tgc acc atg aga ctt cgc cac aac att ggc cag act tca tca cct<br>Ile Cys Thr Met Arg Leu Arg His Asn Ile Gly Gln Thr Ser Ser Pro<br>           340                   345                 350 | 1056 |

-continued

```
gac atc tac aac cct caa gcc ggt agc gtc aca acc gcc acc agc ctt    1104
Asp Ile Tyr Asn Pro Gln Ala Gly Ser Val Thr Thr Ala Thr Ser Leu
            355                 360                 365 gac ttc cca gcc ctc tcg tgg ctc aga ctc agt gct gag ttt gga tct    1152
Asp Phe Pro Ala Leu Ser Trp Leu Arg Leu Ser Ala Glu Phe Gly Ser
370                 375                 380 ctc cgc aag aat gca atg ttc gtg cca cac tac aac ctg aac gcg aac    1200
Leu Arg Lys Asn Ala Met Phe Val Pro His Tyr Asn Leu Asn Ala Asn
385                 390                 395                 400 agc ata ata tac gca ttg aat gga cgg gca ttg ata caa gtg gtg aat    1248
Ser Ile Ile Tyr Ala Leu Asn Gly Arg Ala Leu Ile Gln Val Val Asn
            405                 410                 415 tgc aac ggt gag aga gtg ttt gat gga gag ctg caa gag gga cgg gtg    1296
Cys Asn Gly Glu Arg Val Phe Asp Gly Glu Leu Gln Glu Gly Arg Val
        420                 425                 430 ctg atc gtg cca caa aac ttt gtg gtg gct gca aga tca cag agt gac    1344
Leu Ile Val Pro Gln Asn Phe Val Val Ala Ala Arg Ser Gln Ser Asp
            435                 440                 445 aac ttc gag tat gtg tca ttc aag acc aat gat aca ccc atg atc ggc    1392
Asn Phe Glu Tyr Val Ser Phe Lys Thr Asn Asp Thr Pro Met Ile Gly
450                 455                 460 act ctt gca ggg gca aac tca ttg ttg aac gca tta cca gag gaa gtg    1440
Thr Leu Ala Gly Ala Asn Ser Leu Leu Asn Ala Leu Pro Glu Glu Val
465                 470                 475                 480 att cag cac act ttc aac cta aaa agc cag cag gcc agg cag ata aag    1488
Ile Gln His Thr Phe Asn Leu Lys Ser Gln Gln Ala Arg Gln Ile Lys
            485                 490                 495 aac aac aac cct ttc aag ttc ctg gtt cca cct cag gag tct cag aag    1536
Asn Asn Asn Pro Phe Lys Phe Leu Val Pro Pro Gln Glu Ser Gln Lys
        500                 505                 510 aga gct gtg gct tag                                                 1551
Arg Ala Val Ala
        515

<210> SEQ ID NO 23
<211> LENGTH: 516
<212> TYPE: PRT
<213> ORGANISM: Glycine max
<220> FEATURE:
<223> OTHER INFORMATION: A1aB1bM2

<400> SEQUENCE: 23

Met Ala Lys Leu Val Phe Ser Leu Cys Phe Leu Leu Phe Ser Gly Cys
1               5                   10                  15

Cys Phe Ala Phe Ser Ser Arg Glu Gln Pro Gln Gln Asn Glu Cys Gln
            20                  25                  30

Ile Gln Lys Leu Asn Ala Leu Lys Pro Asp Asn Arg Ile Glu Ser Glu
        35                  40                  45

Gly Gly Leu Ile Glu Thr Trp Asn Pro Asn Asn Lys Pro Phe Gln Cys
    50                  55                  60

Ala Gly Val Ala Leu Ser Arg Cys Thr Leu Asn Arg Asn Ala Leu Arg
65                  70                  75                  80

Arg Pro Ser Tyr Thr Asn Gly Pro Gln Glu Ile Tyr Ile Gln Gln Gly
                85                  90                  95

Lys Gly Ile Phe Gly Met Ile Tyr Pro Gly Cys Pro Ser Thr Phe Glu
            100                 105                 110

Glu Pro Gln Gln Pro Gln Gln Arg Phe Arg His Asp Ser Gly Tyr Phe
        115                 120                 125
```

Arg His Asp Ser Gly Tyr Phe Arg His Asp Ser Gly Tyr Ala Gln Ser
130                     135                 140

Ser Arg Pro Gln Asp Arg His Gln Lys Ile Tyr Asn Phe Arg Glu Gly
145                 150                 155                 160

Asp Leu Ile Ala Val Pro Thr Gly Val Ala Trp Trp Met Tyr Asn Asn
                165                 170                 175

Glu Asp Thr Pro Val Val Ala Val Ser Ile Ile Asp Thr Asn Ser Leu
            180                 185                 190

Glu Asn Gln Leu Asp Gln Met Pro Arg Arg Phe Tyr Leu Ala Gly Asn
        195                 200                 205

Gln Glu Gln Glu Phe Leu Lys Tyr Gln Gln Glu Gln Gly Gly His Gln
210                 215                 220

Ser Gln Lys Gly Lys His Gln Gln Glu Glu Asn Glu Gly Gly Ser
225                 230                 235                 240

Ile Leu Ser Gly Phe Thr Leu Glu Phe Leu Glu His Ala Phe Ser Val
                245                 250                 255

Asp Lys Gln Ile Ala Lys Asn Leu Gln Gly Gly Asn Gly Gly Glu Asp
            260                 265                 270

Lys Gly Ala Ile Val Thr Val Lys Gly Gly Leu Ser Val Ile Lys Pro
        275                 280                 285

Pro Thr Asp Glu Gln Gln Gln Arg Pro Gln Glu Glu Glu Glu Glu
290                 295                 300

Glu Asp Glu Lys Pro Gln Cys Lys Gly Lys Asp Lys His Cys Gln Arg
305                 310                 315                 320

Pro Arg Gly Ser Gln Ser Lys Ser Arg Arg Asn Gly Ile Asp Glu Thr
                325                 330                 335

Ile Cys Thr Met Arg Leu Arg His Asn Ile Gly Gln Thr Ser Ser Pro
            340                 345                 350

Asp Ile Tyr Asn Pro Gln Ala Gly Ser Val Thr Thr Ala Thr Ser Leu
        355                 360                 365

Asp Phe Pro Ala Leu Ser Trp Leu Arg Leu Ser Ala Glu Phe Gly Ser
370                 375                 380

Leu Arg Lys Asn Ala Met Phe Val Pro His Tyr Asn Leu Asn Ala Asn
385                 390                 395                 400

Ser Ile Ile Tyr Ala Leu Asn Gly Arg Ala Leu Ile Gln Val Val Asn
                405                 410                 415

Cys Asn Gly Glu Arg Val Phe Asp Gly Glu Leu Gln Glu Gly Arg Val
            420                 425                 430

Leu Ile Val Pro Gln Asn Phe Val Val Ala Ala Arg Ser Gln Ser Asp
        435                 440                 445

Asn Phe Glu Tyr Val Ser Phe Lys Thr Asn Asp Thr Pro Met Ile Gly
450                 455                 460

Thr Leu Ala Gly Ala Asn Ser Leu Leu Asn Ala Leu Pro Glu Glu Val
465                 470                 475                 480

Ile Gln His Thr Phe Asn Leu Lys Ser Gln Gln Ala Arg Gln Ile Lys
                485                 490                 495

Asn Asn Asn Pro Phe Lys Phe Leu Val Pro Pro Gln Glu Ser Gln Lys
            500                 505                 510

Arg Ala Val Ala
        515

<210> SEQ ID NO 24
<211> LENGTH: 1551
<212> TYPE: DNA

```
<213> ORGANISM: Glycine max
<220> FEATURE:
<221> NAME/KEY: CDS
<222> LOCATION: (1)..(1548)
<220> FEATURE:
<223> OTHER INFORMATION: A1aB1bM3

<400> SEQUENCE: 24
```

| | | | | | | | | | | | | | | | | |
|---|---|---|---|---|---|---|---|---|---|---|---|---|---|---|---|---|
| atg | gcc | aag | cta | gtt | ttt | tcc | ctt | tgt | ttt | ctg | ctt | ttc | agt | ggc | tgc | 48 |
| Met | Ala | Lys | Leu | Val | Phe | Ser | Leu | Cys | Phe | Leu | Leu | Phe | Ser | Gly | Cys | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| tgc | ttc | gct | ttc | agt | tcc | aga | gag | cag | cct | cag | caa | aac | gag | tgc | cag | 96 |
| Cys | Phe | Ala | Phe | Ser | Ser | Arg | Glu | Gln | Pro | Gln | Gln | Asn | Glu | Cys | Gln | |
| | | | 20 | | | | | 25 | | | | | 30 | | | |

| | | | | | | | | | | | | | | | | |
|---|---|---|---|---|---|---|---|---|---|---|---|---|---|---|---|---|
| atc | caa | aaa | ctc | aat | gcc | ctc | aaa | ccg | gat | aac | cgt | ata | gag | tca | gaa | 144 |
| Ile | Gln | Lys | Leu | Asn | Ala | Leu | Lys | Pro | Asp | Asn | Arg | Ile | Glu | Ser | Glu | |
| | | 35 | | | | | 40 | | | | | 45 | | | | |

| | | | | | | | | | | | | | | | | |
|---|---|---|---|---|---|---|---|---|---|---|---|---|---|---|---|---|
| gga | ggg | ctc | att | gag | aca | tgg | aac | cct | aac | aac | aag | cca | ttc | cag | tgt | 192 |
| Gly | Gly | Leu | Ile | Glu | Thr | Trp | Asn | Pro | Asn | Asn | Lys | Pro | Phe | Gln | Cys | |
| 50 | | | | | 55 | | | | | 60 | | | | | | |

| | | | | | | | | | | | | | | | | |
|---|---|---|---|---|---|---|---|---|---|---|---|---|---|---|---|---|
| gcc | ggt | gtt | gcc | ctc | tct | cgc | tgc | acc | ctc | aac | cgc | aac | gcc | ctt | cgt | 240 |
| Ala | Gly | Val | Ala | Leu | Ser | Arg | Cys | Thr | Leu | Asn | Arg | Asn | Ala | Leu | Arg | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| aga | cct | tcc | tac | acc | aac | ggt | ccc | cag | gaa | atc | tac | atc | caa | caa | ggt | 288 |
| Arg | Pro | Ser | Tyr | Thr | Asn | Gly | Pro | Gln | Glu | Ile | Tyr | Ile | Gln | Gln | Gly | |
| | | | | 85 | | | | | 90 | | | | | 95 | | |

| | | | | | | | | | | | | | | | | |
|---|---|---|---|---|---|---|---|---|---|---|---|---|---|---|---|---|
| aag | ggt | att | ttt | ggc | atg | ata | tac | ccg | ggt | tgt | cct | agc | aca | ttt | gaa | 336 |
| Lys | Gly | Ile | Phe | Gly | Met | Ile | Tyr | Pro | Gly | Cys | Pro | Ser | Thr | Phe | Glu | |
| | | | | 100 | | | | | 105 | | | | | 110 | | |

| | | | | | | | | | | | | | | | | |
|---|---|---|---|---|---|---|---|---|---|---|---|---|---|---|---|---|
| gag | cct | caa | caa | cct | caa | caa | aga | gga | caa | agc | agc | aga | cca | caa | gac | 384 |
| Glu | Pro | Gln | Gln | Pro | Gln | Gln | Arg | Gly | Gln | Ser | Ser | Arg | Pro | Gln | Asp | |
| | | | 115 | | | | | 120 | | | | | 125 | | | |

| | | | | | | | | | | | | | | | | |
|---|---|---|---|---|---|---|---|---|---|---|---|---|---|---|---|---|
| cgt | cac | cag | aag | atc | tat | aac | ttc | aga | gag | ggt | gat | ttg | atc | gca | gtg | 432 |
| Arg | His | Gln | Lys | Ile | Tyr | Asn | Phe | Arg | Glu | Gly | Asp | Leu | Ile | Ala | Val | |
| | | 130 | | | | | 135 | | | | | 140 | | | | |

| | | | | | | | | | | | | | | | | |
|---|---|---|---|---|---|---|---|---|---|---|---|---|---|---|---|---|
| cct | act | ggt | gtt | gca | tgg | tgg | atg | tac | aac | aat | gaa | gac | act | cct | gtt | 480 |
| Pro | Thr | Gly | Val | Ala | Trp | Trp | Met | Tyr | Asn | Asn | Glu | Asp | Thr | Pro | Val | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| gtt | gcc | gtt | tct | att | att | gac | acc | aac | agc | ttg | gag | aac | cag | ctc | gac | 528 |
| Val | Ala | Val | Ser | Ile | Ile | Asp | Thr | Asn | Ser | Leu | Glu | Asn | Gln | Leu | Asp | |
| | | | | 165 | | | | | 170 | | | | | 175 | | |

| | | | | | | | | | | | | | | | | |
|---|---|---|---|---|---|---|---|---|---|---|---|---|---|---|---|---|
| cag | atg | cct | agg | aga | ttc | tat | ctt | gct | ggg | aac | caa | gag | caa | gag | ttt | 576 |
| Gln | Met | Pro | Arg | Arg | Phe | Tyr | Leu | Ala | Gly | Asn | Gln | Glu | Gln | Glu | Phe | |
| | | | | 180 | | | | | 185 | | | | | 190 | | |

| | | | | | | | | | | | | | | | | |
|---|---|---|---|---|---|---|---|---|---|---|---|---|---|---|---|---|
| cta | aaa | tat | cag | caa | gag | caa | gga | ggt | cat | caa | ttt | aga | cat | gat | tct | 624 |
| Leu | Lys | Tyr | Gln | Gln | Glu | Gln | Gly | Gly | His | Gln | Phe | Arg | His | Asp | Ser | |
| | | | 195 | | | | | 200 | | | | | 205 | | | |

| | | | | | | | | | | | | | | | | |
|---|---|---|---|---|---|---|---|---|---|---|---|---|---|---|---|---|
| ggt | tat | ttc | aga | cac | gat | agc | ggc | tac | ttc | agg | cat | gac | tca | gga | tat | 672 |
| Gly | Tyr | Phe | Arg | His | Asp | Ser | Gly | Tyr | Phe | Arg | His | Asp | Ser | Gly | Tyr | |
| | | 210 | | | | | 215 | | | | | 220 | | | | |

| | | | | | | | | | | | | | | | | |
|---|---|---|---|---|---|---|---|---|---|---|---|---|---|---|---|---|
| gcc | cag | aaa | gga | aag | cat | cag | caa | gaa | gaa | gaa | aac | gaa | gga | ggc | agc | 720 |
| Ala | Gln | Lys | Gly | Lys | His | Gln | Gln | Glu | Glu | Glu | Asn | Glu | Gly | Gly | Ser | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| ata | ttg | agt | ggc | ttc | acc | ctg | gaa | ttc | ttg | gaa | cat | gca | ttc | agc | gtg | 768 |
| Ile | Leu | Ser | Gly | Phe | Thr | Leu | Glu | Phe | Leu | Glu | His | Ala | Phe | Ser | Val | |
| | | | | 245 | | | | | 250 | | | | | 255 | | |

| | | | | | | | | | | | | | | | | |
|---|---|---|---|---|---|---|---|---|---|---|---|---|---|---|---|---|
| gac | aag | cag | ata | gcg | aaa | aac | cta | caa | gga | gag | aac | gaa | ggg | gaa | gac | 816 |
| Asp | Lys | Gln | Ile | Ala | Lys | Asn | Leu | Gln | Gly | Glu | Asn | Glu | Gly | Glu | Asp | |
| | | | 260 | | | | | 265 | | | | | 270 | | | |

| | | | | | | | | | | | | | | | | |
|---|---|---|---|---|---|---|---|---|---|---|---|---|---|---|---|---|
| aag | gga | gcc | att | gtg | aca | gtg | aaa | gga | ggt | ctg | agc | gtg | ata | aaa | cca | 864 |
| Lys | Gly | Ala | Ile | Val | Thr | Val | Lys | Gly | Gly | Leu | Ser | Val | Ile | Lys | Pro | |

```
                275                 280                 285
ccc acg gac gag cag caa caa aga ccc cag gaa gag gaa gaa gaa           912
Pro Thr Asp Glu Gln Gln Gln Arg Pro Gln Glu Glu Glu Glu Glu
    290                 295                 300 gag gat gag aag cca cag tgc aag ggt aaa gac aaa cac tgc caa cgc       960
Glu Asp Glu Lys Pro Gln Cys Lys Gly Lys Asp Lys His Cys Gln Arg
305                 310                 315                 320 ccc cga gga agc caa agc aaa agc aga aga aat ggc att gac gag acc      1008
Pro Arg Gly Ser Gln Ser Lys Ser Arg Arg Asn Gly Ile Asp Glu Thr
                325                 330                 335 ata tgc acc atg aga ctt cgc cac aac att ggc cag act tca tca cct      1056
Ile Cys Thr Met Arg Leu Arg His Asn Ile Gly Gln Thr Ser Ser Pro
            340                 345                 350 gac atc tac aac cct caa gcc ggt agc gtc aca acc gcc acc agc ctt      1104
Asp Ile Tyr Asn Pro Gln Ala Gly Ser Val Thr Thr Ala Thr Ser Leu
        355                 360                 365 gac ttc cca gcc ctc tcg tgg ctc aga ctc agt gct gag ttt gga tct      1152
Asp Phe Pro Ala Leu Ser Trp Leu Arg Leu Ser Ala Glu Phe Gly Ser
    370                 375                 380 ctc cgc aag aat gca atg ttc gtg cca cac tac aac ctg aac gcg aac      1200
Leu Arg Lys Asn Ala Met Phe Val Pro His Tyr Asn Leu Asn Ala Asn
385                 390                 395                 400 agc ata ata tac gca ttg aat gga cgg gca ttg ata caa gtg gtg aat      1248
Ser Ile Ile Tyr Ala Leu Asn Gly Arg Ala Leu Ile Gln Val Val Asn
                405                 410                 415 tgc aac ggt gag aga gtg ttt gat gga gag ctg caa gag gga cgg gtg      1296
Cys Asn Gly Glu Arg Val Phe Asp Gly Glu Leu Gln Glu Gly Arg Val
            420                 425                 430 ctg atc gtg cca caa aac ttt gtg gtg gct gca aga tca cag agt gac      1344
Leu Ile Val Pro Gln Asn Phe Val Val Ala Ala Arg Ser Gln Ser Asp
        435                 440                 445 aac ttc gag tat gtg tca ttc aag acc aat gat aca ccc atg atc ggc      1392
Asn Phe Glu Tyr Val Ser Phe Lys Thr Asn Asp Thr Pro Met Ile Gly
    450                 455                 460 act ctt gca ggg gca aac tca ttg ttg aac gca tta cca gag gaa gtg      1440
Thr Leu Ala Gly Ala Asn Ser Leu Leu Asn Ala Leu Pro Glu Glu Val
465                 470                 475                 480 att cag cac act ttc aac cta aaa agc cag cag gcc agg cag ata aag      1488
Ile Gln His Thr Phe Asn Leu Lys Ser Gln Gln Ala Arg Gln Ile Lys
                485                 490                 495 aac aac aac cct ttc aag ttc ctg gtt cca cct cag gag tct cag aag      1536
Asn Asn Asn Pro Phe Lys Phe Leu Val Pro Pro Gln Glu Ser Gln Lys
            500                 505                 510 aga gct gtg gct tag                                                  1551
Arg Ala Val Ala
        515

<210> SEQ ID NO 25
<211> LENGTH: 516
<212> TYPE: PRT
<213> ORGANISM: Glycine max
<220> FEATURE:
<223> OTHER INFORMATION: A1aB1bM3

<400> SEQUENCE: 25

Met Ala Lys Leu Val Phe Ser Leu Cys Phe Leu Leu Phe Ser Gly Cys
1               5                   10                  15

Cys Phe Ala Phe Ser Ser Arg Glu Gln Pro Gln Gln Asn Glu Cys Gln
            20                  25                  30

Ile Gln Lys Leu Asn Ala Leu Lys Pro Asp Asn Arg Ile Glu Ser Glu
```

```
                35                  40                  45
Gly Gly Leu Ile Glu Thr Trp Asn Pro Asn Asn Lys Pro Phe Gln Cys
 50                  55                  60

Ala Gly Val Ala Leu Ser Arg Cys Thr Leu Asn Arg Asn Ala Leu Arg
65                   70                  75                   80

Arg Pro Ser Tyr Thr Asn Gly Pro Gln Glu Ile Tyr Ile Gln Gln Gly
                 85                  90                  95

Lys Gly Ile Phe Gly Met Ile Tyr Pro Gly Cys Pro Ser Thr Phe Glu
                100                 105                 110

Glu Pro Gln Gln Pro Gln Gln Arg Gly Gln Ser Ser Arg Pro Gln Asp
            115                 120                 125

Arg His Gln Lys Ile Tyr Asn Phe Arg Glu Gly Asp Leu Ile Ala Val
        130                 135                 140

Pro Thr Gly Val Ala Trp Trp Met Tyr Asn Asn Glu Asp Thr Pro Val
145                 150                 155                 160

Val Ala Val Ser Ile Ile Asp Thr Asn Ser Leu Glu Asn Gln Leu Asp
                165                 170                 175

Gln Met Pro Arg Arg Phe Tyr Leu Ala Gly Asn Gln Glu Gln Glu Phe
            180                 185                 190

Leu Lys Tyr Gln Gln Glu Gln Gly Gly His Gln Phe Arg His Asp Ser
        195                 200                 205

Gly Tyr Phe Arg His Asp Ser Gly Tyr Phe Arg His Asp Ser Gly Tyr
    210                 215                 220

Ala Gln Lys Gly Lys His Gln Gln Glu Glu Asn Glu Gly Gly Ser
225                 230                 235                 240

Ile Leu Ser Gly Phe Thr Leu Glu Phe Leu Glu His Ala Phe Ser Val
                245                 250                 255

Asp Lys Gln Ile Ala Lys Asn Leu Gln Gly Glu Asn Glu Gly Glu Asp
            260                 265                 270

Lys Gly Ala Ile Val Thr Val Lys Gly Gly Leu Ser Val Ile Lys Pro
        275                 280                 285

Pro Thr Asp Glu Gln Gln Gln Arg Pro Gln Glu Glu Glu Glu Glu Glu
290                 295                 300

Glu Asp Glu Lys Pro Gln Cys Lys Gly Lys Asp Lys His Cys Gln Arg
305                 310                 315                 320

Pro Arg Gly Ser Gln Ser Lys Ser Arg Arg Asn Gly Ile Asp Glu Thr
                325                 330                 335

Ile Cys Thr Met Arg Leu Arg His Asn Ile Gly Gln Thr Ser Ser Pro
            340                 345                 350

Asp Ile Tyr Asn Pro Gln Ala Gly Ser Val Thr Thr Ala Thr Ser Leu
        355                 360                 365

Asp Phe Pro Ala Leu Ser Trp Leu Arg Leu Ser Ala Glu Phe Gly Ser
    370                 375                 380

Leu Arg Lys Asn Ala Met Phe Val Pro His Tyr Asn Leu Asn Ala Asn
385                 390                 395                 400

Ser Ile Ile Tyr Ala Leu Asn Gly Arg Ala Leu Ile Gln Val Val Asn
                405                 410                 415

Cys Asn Gly Glu Arg Val Phe Asp Gly Glu Leu Gln Glu Gly Arg Val
            420                 425                 430

Leu Ile Val Pro Gln Asn Phe Val Val Ala Ala Arg Ser Gln Ser Asp
        435                 440                 445

Asn Phe Glu Tyr Val Ser Phe Lys Thr Asn Asp Thr Pro Met Ile Gly
    450                 455                 460
```

| | | | | | | | | | | | | |
|---|---|---|---|---|---|---|---|---|---|---|---|---|
| Thr | Leu | Ala | Gly | Ala | Asn | Ser | Leu | Leu | Asn | Ala | Leu | Pro | Glu | Glu | Val |
| 465 | | | | | 470 | | | | | 475 | | | | | 480 |

Ile Gln His Thr Phe Asn Leu Lys Ser Gln Gln Ala Arg Gln Ile Lys
            485                 490                 495

Asn Asn Asn Pro Phe Lys Phe Leu Val Pro Pro Gln Glu Ser Gln Lys
        500                 505                 510

Arg Ala Val Ala
        515

<210> SEQ ID NO 26
<211> LENGTH: 1551
<212> TYPE: DNA
<213> ORGANISM: Glycine max
<220> FEATURE:
<221> NAME/KEY: CDS
<222> LOCATION: (1)..(1548)
<220> FEATURE:
<223> OTHER INFORMATION: A1aB1bM4-1

<400> SEQUENCE: 26

```
atg gcc aag cta gtt ttt tcc ctt tgt ttt ctg ctt ttc agt ggc tgc        48
Met Ala Lys Leu Val Phe Ser Leu Cys Phe Leu Leu Phe Ser Gly Cys
1               5                   10                  15 tgc ttc gct ttc agt tcc aga gag cag cct cag caa aac gag tgc cag        96
Cys Phe Ala Phe Ser Ser Arg Glu Gln Pro Gln Gln Asn Glu Cys Gln
                20                  25                  30 atc caa aaa ctc aat gcc ctc aaa ccg gat aac cgt ata gag tca gaa       144
Ile Gln Lys Leu Asn Ala Leu Lys Pro Asp Asn Arg Ile Glu Ser Glu
            35                  40                  45 gga ggg ctc att gag aca tgg aac cct aac aac aag cca ttc cag tgt       192
Gly Gly Leu Ile Glu Thr Trp Asn Pro Asn Asn Lys Pro Phe Gln Cys
        50                  55                  60 gcc ggt gtt gcc ctc tct cgc tgc acc ctc aac cgc aac gcc ctt cgt       240
Ala Gly Val Ala Leu Ser Arg Cys Thr Leu Asn Arg Asn Ala Leu Arg
65                  70                  75                  80 aga cct tcc tac acc aac ggt ccc cag gaa atc tac atc caa caa ggt       288
Arg Pro Ser Tyr Thr Asn Gly Pro Gln Glu Ile Tyr Ile Gln Gln Gly
                85                  90                  95 aag ggt att ttt ggc atg ata tac ccg ggt tgt cct agc aca ttt gaa       336
Lys Gly Ile Phe Gly Met Ile Tyr Pro Gly Cys Pro Ser Thr Phe Glu
            100                 105                 110 gag cct caa caa cct caa caa aga gga caa agc agc aga cca caa gac       384
Glu Pro Gln Gln Pro Gln Gln Arg Gly Gln Ser Ser Arg Pro Gln Asp
        115                 120                 125 cgt cac cag aag atc tat aac ttc aga gag ggt gat ttg atc gca gtg       432
Arg His Gln Lys Ile Tyr Asn Phe Arg Glu Gly Asp Leu Ile Ala Val
130                 135                 140 cct act ggt gtt gca tgg tgg atg tac aac aat gaa gac act cct gtt       480
Pro Thr Gly Val Ala Trp Trp Met Tyr Asn Asn Glu Asp Thr Pro Val
145                 150                 155                 160 gtt gcc gtt tct att att gac acc aac agc ttg gag aac cag ctc gac       528
Val Ala Val Ser Ile Ile Asp Thr Asn Ser Leu Glu Asn Gln Leu Asp
                165                 170                 175 cag atg cct agg aga ttc tat ctt gct ggg aac caa gag caa gag ttt       576
Gln Met Pro Arg Arg Phe Tyr Leu Ala Gly Asn Gln Glu Gln Glu Phe
            180                 185                 190 cta aaa tat cag caa gag caa gga ggt cat caa agc cag aaa gga aag       624
Leu Lys Tyr Gln Gln Glu Gln Gly Gly His Gln Ser Gln Lys Gly Lys
        195                 200                 205 cat cag caa gaa gaa gaa aac gaa gga ggc agc ata ttg agt ggc ttc       672
```

```
                His Gln Gln Glu Glu Glu Asn Glu Gly Gly Ser Ile Leu Ser Gly Phe
                    210                 215                 220 acc ctg gaa ttc ttg gaa cat gca ttc agc gtg gac aag cag ata gcg        720
Thr Leu Glu Phe Leu Glu His Ala Phe Ser Val Asp Lys Gln Ile Ala
225                 230                 235                 240 aaa aac cta caa gga gag aac gaa ggg gaa gac aag gga gcc att gtg        768
Lys Asn Leu Gln Gly Glu Asn Glu Gly Glu Asp Lys Gly Ala Ile Val
                245                 250                 255 aca gtg aaa gga ggt ctg agc gtg ata aaa cca ccc acg gac gag cag        816
Thr Val Lys Gly Gly Leu Ser Val Ile Lys Pro Pro Thr Asp Glu Gln
            260                 265                 270 caa caa aga ccc cag gaa gag gaa gaa gaa gag gat gag aag cca            864
Gln Gln Arg Pro Gln Glu Glu Glu Glu Glu Glu Asp Glu Lys Pro
        275                 280                 285 cag tgc aag ggt aaa gac aaa cac tgc caa cgc ttt aga cat gat tct        912
Gln Cys Lys Gly Lys Asp Lys His Cys Gln Arg Phe Arg His Asp Ser
290                 295                 300 ggt tat ttc aga cac gat agc ggc tac ttc agg cat gac tca gga tat        960
Gly Tyr Phe Arg His Asp Ser Gly Tyr Phe Arg His Asp Ser Gly Tyr
305                 310                 315                 320 gcc cga gga agc caa agc aaa agc aga aga aat ggc att gac gag acc       1008
Ala Arg Gly Ser Gln Ser Lys Ser Arg Arg Asn Gly Ile Asp Glu Thr
                325                 330                 335 ata tgc acc atg aga ctt cgc cac aac att ggc cag act tca tca cct       1056
Ile Cys Thr Met Arg Leu Arg His Asn Ile Gly Gln Thr Ser Ser Pro
            340                 345                 350 gac atc tac aac cct caa gcc ggt agc gtc aca acc gcc acc agc ctt       1104
Asp Ile Tyr Asn Pro Gln Ala Gly Ser Val Thr Thr Ala Thr Ser Leu
        355                 360                 365 gac ttc cca gcc ctc tcg tgg ctc aga ctc agt gct gag ttt gga tct       1152
Asp Phe Pro Ala Leu Ser Trp Leu Arg Leu Ser Ala Glu Phe Gly Ser
370                 375                 380 ctc cgc aag aat gca atg ttc gtg cca cac tac aac ctg aac gcg aac       1200
Leu Arg Lys Asn Ala Met Phe Val Pro His Tyr Asn Leu Asn Ala Asn
385                 390                 395                 400 agc ata ata tac gca ttg aat gga cgg gca ttg ata caa gtg gtg aat       1248
Ser Ile Ile Tyr Ala Leu Asn Gly Arg Ala Leu Ile Gln Val Val Asn
                405                 410                 415 tgc aac ggt gag aga gtg ttt gat gga gag ctg caa gag gga cgg gtg       1296
Cys Asn Gly Glu Arg Val Phe Asp Gly Glu Leu Gln Glu Gly Arg Val
            420                 425                 430 ctg atc gtg cca caa aac ttt gtg gtg gct gca aga tca cag agt gac       1344
Leu Ile Val Pro Gln Asn Phe Val Val Ala Ala Arg Ser Gln Ser Asp
        435                 440                 445 aac ttc gag tat gtg tca ttc aag acc aat gat aca ccc atg atc ggc       1392
Asn Phe Glu Tyr Val Ser Phe Lys Thr Asn Asp Thr Pro Met Ile Gly
450                 455                 460 act ctt gca ggg gca aac tca ttg ttg aac gca tta cca gag gaa gtg       1440
Thr Leu Ala Gly Ala Asn Ser Leu Leu Asn Ala Leu Pro Glu Glu Val
465                 470                 475                 480 att cag cac act ttc aac cta aaa agc cag cag gcc agg cag ata aag       1488
Ile Gln His Thr Phe Asn Leu Lys Ser Gln Gln Ala Arg Gln Ile Lys
                485                 490                 495 aac aac aac cct ttc aag ttc ctg gtt cca cct cag gag tct cag aag       1536
Asn Asn Asn Pro Phe Lys Phe Leu Val Pro Pro Gln Glu Ser Gln Lys
            500                 505                 510 aga gct gtg gct tag                                                    1551
Arg Ala Val Ala
        515
```

<210> SEQ ID NO 27
<211> LENGTH: 516
<212> TYPE: PRT
<213> ORGANISM: Glycine max
<220> FEATURE:
<223> OTHER INFORMATION: A1aB1bM4-1

<400> SEQUENCE: 27

```
Met Ala Lys Leu Val Phe Ser Leu Cys Phe Leu Phe Ser Gly Cys
1               5                   10                  15

Cys Phe Ala Phe Ser Ser Arg Glu Gln Pro Gln Gln Asn Glu Cys Gln
                20                  25                  30

Ile Gln Lys Leu Asn Ala Leu Lys Pro Asp Asn Arg Ile Glu Ser Glu
            35                  40                  45

Gly Gly Leu Ile Glu Thr Trp Asn Pro Asn Asn Lys Pro Phe Gln Cys
50                  55                  60

Ala Gly Val Ala Leu Ser Arg Cys Thr Leu Asn Arg Asn Ala Leu Arg
65                  70                  75                  80

Arg Pro Ser Tyr Thr Asn Gly Pro Gln Glu Ile Tyr Ile Gln Gln Gly
                85                  90                  95

Lys Gly Ile Phe Gly Met Ile Tyr Pro Gly Cys Pro Ser Thr Phe Glu
            100                 105                 110

Glu Pro Gln Gln Pro Gln Gln Arg Gly Gln Ser Ser Arg Pro Gln Asp
        115                 120                 125

Arg His Gln Lys Ile Tyr Asn Phe Arg Glu Gly Asp Leu Ile Ala Val
    130                 135                 140

Pro Thr Gly Val Ala Trp Trp Met Tyr Asn Asn Glu Asp Thr Pro Val
145                 150                 155                 160

Val Ala Val Ser Ile Ile Asp Thr Asn Ser Leu Glu Asn Gln Leu Asp
                165                 170                 175

Gln Met Pro Arg Arg Phe Tyr Leu Ala Gly Asn Gln Glu Gln Glu Phe
            180                 185                 190

Leu Lys Tyr Gln Gln Glu Gln Gly Gly His Gln Ser Gln Lys Gly Lys
        195                 200                 205

His Gln Gln Glu Glu Asn Glu Gly Gly Ser Ile Leu Ser Gly Phe
    210                 215                 220

Thr Leu Glu Phe Leu Glu His Ala Phe Ser Val Asp Lys Gln Ile Ala
225                 230                 235                 240

Lys Asn Leu Gln Gly Glu Asn Glu Gly Glu Asp Lys Gly Ala Ile Val
                245                 250                 255

Thr Val Lys Gly Gly Leu Ser Val Ile Lys Pro Pro Thr Asp Glu Gln
            260                 265                 270

Gln Gln Arg Pro Gln Glu Glu Glu Glu Glu Asp Glu Lys Pro
        275                 280                 285

Gln Cys Lys Gly Lys Asp Lys His Cys Gln Arg Phe Arg His Asp Ser
    290                 295                 300

Gly Tyr Phe Arg His Asp Ser Gly Tyr Phe Arg His Asp Ser Gly Tyr
305                 310                 315                 320

Ala Arg Gly Ser Gln Ser Lys Ser Arg Arg Asn Gly Ile Asp Glu Thr
                325                 330                 335

Ile Cys Thr Met Arg Leu Arg His Asn Ile Gly Gln Thr Ser Ser Pro
            340                 345                 350

Asp Ile Tyr Asn Pro Gln Ala Gly Ser Val Thr Thr Ala Thr Ser Leu
        355                 360                 365
```

```
Asp Phe Pro Ala Leu Ser Trp Leu Arg Leu Ser Ala Glu Phe Gly Ser
    370                 375                 380

Leu Arg Lys Asn Ala Met Phe Val Pro His Tyr Asn Leu Asn Ala Asn
385                 390                 395                 400

Ser Ile Ile Tyr Ala Leu Asn Gly Arg Ala Leu Ile Gln Val Val Asn
                405                 410                 415

Cys Asn Gly Glu Arg Val Phe Asp Gly Glu Leu Gln Glu Gly Arg Val
            420                 425                 430

Leu Ile Val Pro Gln Asn Phe Val Ala Ala Arg Ser Gln Ser Asp
            435                 440                 445

Asn Phe Glu Tyr Val Ser Phe Lys Thr Asn Asp Thr Pro Met Ile Gly
    450                 455                 460

Thr Leu Ala Gly Ala Asn Ser Leu Leu Asn Ala Leu Pro Glu Glu Val
465                 470                 475                 480

Ile Gln His Thr Phe Asn Leu Lys Ser Gln Gln Ala Arg Gln Ile Lys
                485                 490                 495

Asn Asn Asn Pro Phe Lys Phe Leu Val Pro Pro Gln Glu Ser Gln Lys
            500                 505                 510

Arg Ala Val Ala
        515

<210> SEQ ID NO 28
<211> LENGTH: 1677
<212> TYPE: DNA
<213> ORGANISM: Glycine max
<220> FEATURE:
<221> NAME/KEY: CDS
<222> LOCATION: (1)..(1674)
<220> FEATURE:
<223> OTHER INFORMATION: A1aB1bM1

<400> SEQUENCE: 28 atg gcc aag cta gtt ttt tcc ctt tgt ttt ctg ctt ttc agt ggc tgc      48
Met Ala Lys Leu Val Phe Ser Leu Cys Phe Leu Leu Phe Ser Gly Cys
1               5                   10                  15 tgc ttc gct ttc agt tcc aga gag cag cct cag caa aac gag tgc cag      96
Cys Phe Ala Phe Ser Ser Arg Glu Gln Pro Gln Gln Asn Glu Cys Gln
                20                  25                  30 atc caa aaa ctc aat gcc ctc aaa ccg gat aac cgt ata gag tca gaa     144
Ile Gln Lys Leu Asn Ala Leu Lys Pro Asp Asn Arg Ile Glu Ser Glu
            35                  40                  45 gga ggg ctc att gag aca tgg aac cct aac aac aag cca ttc cag tgt     192
Gly Gly Leu Ile Glu Thr Trp Asn Pro Asn Asn Lys Pro Phe Gln Cys
        50                  55                  60 gcc ggt gtt gcc ctc tct cgc tgc acc ctc aac cgc aac gcc ctt cgt     240
Ala Gly Val Ala Leu Ser Arg Cys Thr Leu Asn Arg Asn Ala Leu Arg
65                  70                  75                  80 aga cct tcc tac acc aac ggt ccc cag gaa atc tac atc caa caa ggt     288
Arg Pro Ser Tyr Thr Asn Gly Pro Gln Glu Ile Tyr Ile Gln Gln Gly
                85                  90                  95 aag ggt att ttt ggc atg ata tac ccg ggt tgt cct agc aca ttt gaa     336
Lys Gly Ile Phe Gly Met Ile Tyr Pro Gly Cys Pro Ser Thr Phe Glu
            100                 105                 110 gag cct caa caa cct caa caa aga ttt aga cat gat tct ggt tat ttc     384
Glu Pro Gln Gln Pro Gln Gln Arg Phe Arg His Asp Ser Gly Tyr Phe
        115                 120                 125 aga cac gat agc ggc tac ttc agg cat gac tca gga tat gca caa agc     432
Arg His Asp Ser Gly Tyr Phe Arg His Asp Ser Gly Tyr Ala Gln Ser
130                 135                 140
```

```
                                          -continued agc aga cca caa gac cgt cac cag aag atc tat aac ttc aga gag ggt     480
Ser Arg Pro Gln Asp Arg His Gln Lys Ile Tyr Asn Phe Arg Glu Gly
145             150                 155                 160 gat ttg atc gca gtg cct act ggt gtt gca tgg tgg atg tac aac aat     528
Asp Leu Ile Ala Val Pro Thr Gly Val Ala Trp Trp Met Tyr Asn Asn
                165                 170                 175 gaa gac act cct gtt gtt gcc gtt tct att att gac acc aac agc ttg     576
Glu Asp Thr Pro Val Val Ala Val Ser Ile Ile Asp Thr Asn Ser Leu
            180                 185                 190 gag aac cag ctc gac cag atg cct agg aga ttc tat ctt gct ggg aac     624
Glu Asn Gln Leu Asp Gln Met Pro Arg Arg Phe Tyr Leu Ala Gly Asn
        195                 200                 205 caa gag caa gag ttt cta aaa tat cag caa gag caa gga ggt cat caa     672
Gln Glu Gln Glu Phe Leu Lys Tyr Gln Gln Glu Gln Gly Gly His Gln
    210                 215                 220 ttt aga cat gat tct ggt tat ttc aga cac gat agc ggc tac ttc agg     720
Phe Arg His Asp Ser Gly Tyr Phe Arg His Asp Ser Gly Tyr Phe Arg
225                 230                 235                 240 cat gac tca gga tat gcc cag aaa gga aag cat cag caa gaa gaa gaa     768
His Asp Ser Gly Tyr Ala Gln Lys Gly Lys His Gln Gln Glu Glu Glu
                245                 250                 255 aac gaa gga ggc agc ata ttg agt ggc ttc acc ctg gaa ttc ttg gaa     816
Asn Glu Gly Gly Ser Ile Leu Ser Gly Phe Thr Leu Glu Phe Leu Glu
            260                 265                 270 cat gca ttc agc gtg gac aag cag ata gcg aaa aac cta caa gga gag     864
His Ala Phe Ser Val Asp Lys Gln Ile Ala Lys Asn Leu Gln Gly Glu
        275                 280                 285 aac gaa ggg gaa gac aag gga gcc att gtg aca gtg aaa gga ggt ctg     912
Asn Glu Gly Glu Asp Lys Gly Ala Ile Val Thr Val Lys Gly Gly Leu
    290                 295                 300 agc gtg ata aaa cca ccc acg gac gag cag caa caa aga ccc cag gaa     960
Ser Val Ile Lys Pro Pro Thr Asp Glu Gln Gln Gln Arg Pro Gln Glu
305                 310                 315                 320 gag gaa gaa gaa gaa gag gat gag aag cca cag tgc aag ggt aaa gac    1008
Glu Glu Glu Glu Glu Glu Asp Glu Lys Pro Gln Cys Lys Gly Lys Asp
                325                 330                 335 aaa cac tgc caa cgc ttt aga cat gat tct ggt tat ttc aga cac gat    1056
Lys His Cys Gln Arg Phe Arg His Asp Ser Gly Tyr Phe Arg His Asp
            340                 345                 350 agc ggc tac ttc agg cat gac tca gga tat gcc cga gga agc caa agc    1104
Ser Gly Tyr Phe Arg His Asp Ser Gly Tyr Ala Arg Gly Ser Gln Ser
        355                 360                 365 aaa agc aga aga aat ggc att gac gag acc ata tgc acc atg aga ctt    1152
Lys Ser Arg Arg Asn Gly Ile Asp Glu Thr Ile Cys Thr Met Arg Leu
    370                 375                 380 cgc cac aac att ggc cag act tca tca cct gac atc tac aac cct caa    1200
Arg His Asn Ile Gly Gln Thr Ser Ser Pro Asp Ile Tyr Asn Pro Gln
385                 390                 395                 400 gcc ggt agc gtc aca acc gcc acc agc ctt gac ttc cca gcc ctc tcg    1248
Ala Gly Ser Val Thr Thr Ala Thr Ser Leu Asp Phe Pro Ala Leu Ser
                405                 410                 415 tgg ctc aga ctc agt gct gag ttt gga tct ctc cgc aag aat gca atg    1296
Trp Leu Arg Leu Ser Ala Glu Phe Gly Ser Leu Arg Lys Asn Ala Met
            420                 425                 430 ttc gtg cca cac tac aac ctg aac gcg aac agc ata ata tac gca ttg    1344
Phe Val Pro His Tyr Asn Leu Asn Ala Asn Ser Ile Ile Tyr Ala Leu
        435                 440                 445 aat gga cgg gca ttg ata caa gtg gtg aat tgc aac ggt gag aga gtg    1392
Asn Gly Arg Ala Leu Ile Gln Val Val Asn Cys Asn Gly Glu Arg Val
    450                 455                 460
```

```
ttt gat gga gag ctg caa gag gga cgg gtg ctg atc gtg cca caa aac    1440
Phe Asp Gly Glu Leu Gln Glu Gly Arg Val Leu Ile Val Pro Gln Asn
465                 470                 475                 480 ttt gtg gtg gct gca aga tca cag agt gac aac ttc gag tat gtg tca    1488
Phe Val Val Ala Ala Arg Ser Gln Ser Asp Asn Phe Glu Tyr Val Ser
                485                 490                 495 ttc aag acc aat gat aca ccc atg atc ggc act ctt gca ggg gca aac    1536
Phe Lys Thr Asn Asp Thr Pro Met Ile Gly Thr Leu Ala Gly Ala Asn
            500                 505                 510 tca ttg ttg aac gca tta cca gag gaa gtg att cag cac act ttc aac    1584
Ser Leu Leu Asn Ala Leu Pro Glu Glu Val Ile Gln His Thr Phe Asn
        515                 520                 525 cta aaa agc cag cag gcc agg cag ata aag aac aac aac cct ttc aag    1632
Leu Lys Ser Gln Gln Ala Arg Gln Ile Lys Asn Asn Asn Pro Phe Lys
    530                 535                 540 ttc ctg gtt cca cct cag gag tct cag aag aga gct gtg gct tag        1677
Phe Leu Val Pro Pro Gln Glu Ser Gln Lys Arg Ala Val Ala
545                 550                 555

<210> SEQ ID NO 29
<211> LENGTH: 558
<212> TYPE: PRT
<213> ORGANISM: Glycine max
<220> FEATURE:
<223> OTHER INFORMATION: A1aB1bM1

<400> SEQUENCE: 29

Met Ala Lys Leu Val Phe Ser Leu Cys Phe Leu Leu Phe Ser Gly Cys
1               5                   10                  15

Cys Phe Ala Phe Ser Ser Arg Glu Gln Pro Gln Gln Asn Glu Cys Gln
            20                  25                  30

Ile Gln Lys Leu Asn Ala Leu Lys Pro Asp Asn Arg Ile Glu Ser Glu
        35                  40                  45

Gly Gly Leu Ile Glu Thr Trp Asn Pro Asn Asn Lys Pro Phe Gln Cys
    50                  55                  60

Ala Gly Val Ala Leu Ser Arg Cys Thr Leu Asn Arg Asn Ala Leu Arg
65                  70                  75                  80

Arg Pro Ser Tyr Thr Asn Gly Pro Gln Glu Ile Tyr Ile Gln Gln Gly
                85                  90                  95

Lys Gly Ile Phe Gly Met Ile Tyr Pro Gly Cys Pro Ser Thr Phe Glu
            100                 105                 110

Glu Pro Gln Gln Pro Gln Gln Arg Phe Arg His Asp Ser Gly Tyr Phe
        115                 120                 125

Arg His Asp Ser Gly Tyr Phe Arg His Asp Ser Gly Tyr Ala Gln Ser
    130                 135                 140

Ser Arg Pro Gln Asp Arg His Gln Lys Ile Tyr Asn Phe Arg Glu Gly
145                 150                 155                 160

Asp Leu Ile Ala Val Pro Thr Gly Val Ala Trp Trp Met Tyr Asn Asn
                165                 170                 175

Glu Asp Thr Pro Val Val Ala Val Ser Ile Ile Asp Thr Asn Ser Leu
            180                 185                 190

Glu Asn Gln Leu Asp Gln Met Pro Arg Arg Phe Tyr Leu Ala Gly Asn
        195                 200                 205

Gln Glu Gln Glu Phe Leu Lys Tyr Gln Gln Glu Gln Gly Gly His Gln
    210                 215                 220

Phe Arg His Asp Ser Gly Tyr Phe Arg His Asp Ser Gly Tyr Phe Arg
225                 230                 235                 240
```

His Asp Ser Gly Tyr Ala Gln Lys Gly Lys His Gln Gln Glu Glu Glu
                245                 250                 255

Asn Glu Gly Gly Ser Ile Leu Ser Gly Phe Thr Leu Glu Phe Leu Glu
            260                 265                 270

His Ala Phe Ser Val Asp Lys Gln Ile Ala Lys Asn Leu Gln Gly Glu
        275                 280                 285

Asn Glu Gly Glu Asp Lys Gly Ala Ile Val Thr Val Lys Gly Gly Leu
    290                 295                 300

Ser Val Ile Lys Pro Pro Thr Asp Glu Gln Gln Arg Pro Gln Glu
305                 310                 315                 320

Glu Glu Glu Glu Glu Asp Glu Lys Pro Gln Cys Lys Gly Lys Asp
                325                 330                 335

Lys His Cys Gln Arg Phe Arg His Asp Ser Gly Tyr Phe Arg His Asp
                340                 345                 350

Ser Gly Tyr Phe Arg His Asp Ser Gly Tyr Ala Arg Gly Ser Gln Ser
            355                 360                 365

Lys Ser Arg Arg Asn Gly Ile Asp Glu Thr Ile Cys Thr Met Arg Leu
        370                 375                 380

Arg His Asn Ile Gly Gln Thr Ser Ser Pro Asp Ile Tyr Asn Pro Gln
385                 390                 395                 400

Ala Gly Ser Val Thr Thr Ala Thr Ser Leu Asp Phe Pro Ala Leu Ser
                405                 410                 415

Trp Leu Arg Leu Ser Ala Glu Phe Gly Ser Leu Arg Lys Asn Ala Met
                420                 425                 430

Phe Val Pro His Tyr Asn Leu Asn Ala Asn Ser Ile Ile Tyr Ala Leu
            435                 440                 445

Asn Gly Arg Ala Leu Ile Gln Val Val Asn Cys Asn Gly Glu Arg Val
        450                 455                 460

Phe Asp Gly Glu Leu Gln Glu Gly Arg Val Leu Ile Val Pro Gln Asn
465                 470                 475                 480

Phe Val Val Ala Ala Arg Ser Gln Ser Asp Asn Phe Glu Tyr Val Ser
                485                 490                 495

Phe Lys Thr Asn Asp Thr Pro Met Ile Gly Thr Leu Ala Gly Ala Asn
            500                 505                 510

Ser Leu Leu Asn Ala Leu Pro Glu Glu Val Ile Gln His Thr Phe Asn
        515                 520                 525

Leu Lys Ser Gln Gln Ala Arg Gln Ile Lys Asn Asn Asn Pro Phe Lys
    530                 535                 540

Phe Leu Val Pro Pro Gln Glu Ser Gln Lys Arg Ala Val Ala
545                 550                 555

<210> SEQ ID NO 30
<211> LENGTH: 1806
<212> TYPE: DNA
<213> ORGANISM: Glycine max
<220> FEATURE:
<221> NAME/KEY: CDS
<222> LOCATION: (1)..(1803)
<220> FEATURE:
<223> OTHER INFORMATION: A1aB1bM5

<400> SEQUENCE: 30

```
atg gcc aag cta gtt ttt tcc ctt tgt ttt ctg ctt ttc agt ggc tgc        48
Met Ala Lys Leu Val Phe Ser Leu Cys Phe Leu Leu Phe Ser Gly Cys
1               5                   10                  15 tgc ttc gct ttc agt tcc aga gag cag cct cag caa aac gag tgc cag        96
```

```
Cys Phe Ala Phe Ser Ser Arg Glu Gln Pro Gln Gln Asn Glu Cys Gln
                20                  25                  30 atc caa aaa ctc aat gcc ctc aaa ccg gat aac cgt ata gag tca gaa      144
Ile Gln Lys Leu Asn Ala Leu Lys Pro Asp Asn Arg Ile Glu Ser Glu
            35                  40                  45 gga ggg ctc att gag aca tgg aac cct aac aac aag cca ttc cag tgt      192
Gly Gly Leu Ile Glu Thr Trp Asn Pro Asn Asn Lys Pro Phe Gln Cys
50                  55                  60 gcc ggt gtt gcc ctc tct cgc tgc acc ctc aac cgc aac gcc ctt cgt      240
Ala Gly Val Ala Leu Ser Arg Cys Thr Leu Asn Arg Asn Ala Leu Arg
 65                  70                  75                  80 aga cct tcc tac acc aac ggt ccc cag gaa atc tac atc caa caa ggt      288
Arg Pro Ser Tyr Thr Asn Gly Pro Gln Glu Ile Tyr Ile Gln Gln Gly
                 85                  90                  95 aag ggt att ttt ggc atg ata tac ccg ggt tgt cct agc aca ttt gaa      336
Lys Gly Ile Phe Gly Met Ile Tyr Pro Gly Cys Pro Ser Thr Phe Glu
            100                 105                 110 gag cct caa caa cct caa caa aga ttt aga cat gat tct ggt tat ttc      384
Glu Pro Gln Gln Pro Gln Gln Arg Phe Arg His Asp Ser Gly Tyr Phe
        115                 120                 125 aga cac gat agc ggc tac ttc agg cat gac tca gga tat gca caa agc      432
Arg His Asp Ser Gly Tyr Phe Arg His Asp Ser Gly Tyr Ala Gln Ser
130                 135                 140 agc aga cca caa gac cgt cac cag aag atc tat aac ttc aga gag ggt      480
Ser Arg Pro Gln Asp Arg His Gln Lys Ile Tyr Asn Phe Arg Glu Gly
145                 150                 155                 160 gat ttg atc gca gtg cct act ggt gtt gca tgg tgg atg tac aac aat      528
Asp Leu Ile Ala Val Pro Thr Gly Val Ala Trp Trp Met Tyr Asn Asn
                165                 170                 175 gaa gac act cct gtt gtt gcc gtt tct att att gac acc aac agc ttg      576
Glu Asp Thr Pro Val Val Ala Val Ser Ile Ile Asp Thr Asn Ser Leu
            180                 185                 190 gag aac cag ctc gac cag atg cct agg aga ttc tat ctt gct ggg aac      624
Glu Asn Gln Leu Asp Gln Met Pro Arg Arg Phe Tyr Leu Ala Gly Asn
        195                 200                 205 caa gag caa gag ttt cta aaa tat cag caa gag caa gga ggt cat caa      672
Gln Glu Gln Glu Phe Leu Lys Tyr Gln Gln Glu Gln Gly Gly His Gln
    210                 215                 220 ttt aga cat gat tct ggt tat ttc aga cac gat agc ggc tac ttc agg      720
Phe Arg His Asp Ser Gly Tyr Phe Arg His Asp Ser Gly Tyr Phe Arg
225                 230                 235                 240 cat gac tca gga tat gcc cag aaa gga aag cat cag caa gaa gaa gaa      768
His Asp Ser Gly Tyr Ala Gln Lys Gly Lys His Gln Gln Glu Glu Glu
                245                 250                 255 aac gaa gga ggc agc ata ttg agt ggc ttc acc ctg gaa ttc ttg gaa      816
Asn Glu Gly Gly Ser Ile Leu Ser Gly Phe Thr Leu Glu Phe Leu Glu
            260                 265                 270 cat gca ttc agc gtg gac aag cag ata gcg aaa aac cta caa gga gag      864
His Ala Phe Ser Val Asp Lys Gln Ile Ala Lys Asn Leu Gln Gly Glu
        275                 280                 285 aac gaa ggg gaa gac aag gga gcc att gtg aca gtg aaa gga ggt ctg      912
Asn Glu Gly Glu Asp Lys Gly Ala Ile Val Thr Val Lys Gly Gly Leu
    290                 295                 300 agc gtg ata aaa cca ccc acg gac gag cag caa caa aga ttt aga cat      960
Ser Val Ile Lys Pro Pro Thr Asp Glu Gln Gln Gln Arg Phe Arg His
305                 310                 315                 320 gat tct ggt tat ttc aga cac gat agc ggc tac ttc agg cat gac tca     1008
Asp Ser Gly Tyr Phe Arg His Asp Ser Gly Tyr Phe Arg His Asp Ser
                325                 330                 335
```

```
gga tat gcc cag gaa gag gaa gaa gaa gag gat gag aag cca cag     1056
Gly Tyr Ala Gln Glu Glu Glu Glu Glu Glu Asp Glu Lys Pro Gln
            340                 345                 350 tgc aag ggt aaa gac aaa cac tgc caa cgc ttt aga cat gat tct ggt  1104
Cys Lys Gly Lys Asp Lys His Cys Gln Arg Phe Arg His Asp Ser Gly
        355                 360                 365 tat ttc aga cac gat agc ggc tac ttc agg cat gac tca gga tat gcc  1152
Tyr Phe Arg His Asp Ser Gly Tyr Phe Arg His Asp Ser Gly Tyr Ala
    370                 375                 380 cga gga agc caa agc aaa agc aga aga aat ggc att gac gag acc ata  1200
Arg Gly Ser Gln Ser Lys Ser Arg Arg Asn Gly Ile Asp Glu Thr Ile
385                 390                 395                 400 tgc acc atg aga ctt cgc cac aac att ggc cag act tca tca cct gac  1248
Cys Thr Met Arg Leu Arg His Asn Ile Gly Gln Thr Ser Ser Pro Asp
                405                 410                 415 atc tac aac cct caa gcc ggt agc gtc aca acc gcc acc agc ctt gac  1296
Ile Tyr Asn Pro Gln Ala Gly Ser Val Thr Thr Ala Thr Ser Leu Asp
            420                 425                 430 ttc cca gcc ctc tcg tgg ctc aga ctc agt gct gag ttt gga tct ctc  1344
Phe Pro Ala Leu Ser Trp Leu Arg Leu Ser Ala Glu Phe Gly Ser Leu
        435                 440                 445 cgc aag aat gca atg ttc gtg cca cac tac aac ctg aac gcg aac agc  1392
Arg Lys Asn Ala Met Phe Val Pro His Tyr Asn Leu Asn Ala Asn Ser
    450                 455                 460 ata ata tac gca ttg aat gga cgg gca ttg ata caa gtg gtg aat tgc  1440
Ile Ile Tyr Ala Leu Asn Gly Arg Ala Leu Ile Gln Val Val Asn Cys
465                 470                 475                 480 aac ggt gag aga gtg ttt gat gga gag ctg caa gag gga cgg gtg ctg  1488
Asn Gly Glu Arg Val Phe Asp Gly Glu Leu Gln Glu Gly Arg Val Leu
                485                 490                 495 atc gtg cca caa aac ttt gtg gtg gct gca aga tca cag agt gac aac  1536
Ile Val Pro Gln Asn Phe Val Val Ala Ala Arg Ser Gln Ser Asp Asn
            500                 505                 510 ttc gag tat gtg tca ttc aag acc aat gat aca ccc atg atc ggc act  1584
Phe Glu Tyr Val Ser Phe Lys Thr Asn Asp Thr Pro Met Ile Gly Thr
        515                 520                 525 ctt gca ggg gca aac tca ttg ttg aac gca tta cca gag gaa gtg att  1632
Leu Ala Gly Ala Asn Ser Leu Leu Asn Ala Leu Pro Glu Glu Val Ile
    530                 535                 540 cag cac act ttc aac cta aaa agc cag cag gcc agg cag ata aag aac  1680
Gln His Thr Phe Asn Leu Lys Ser Gln Gln Ala Arg Gln Ile Lys Asn
545                 550                 555                 560 aac aac cct ttc aag ttc ctg gtt cca cct cag gag tct cag aag aga  1728
Asn Asn Pro Phe Lys Phe Leu Val Pro Pro Gln Glu Ser Gln Lys Arg
                565                 570                 575 gct gtg gct caa ttt aga cat gat tct ggt tat ttc aga cac gat agc  1776
Ala Val Ala Gln Phe Arg His Asp Ser Gly Tyr Phe Arg His Asp Ser
            580                 585                 590 ggc tac ttc agg cat gac tca gga tat tag                          1806
Gly Tyr Phe Arg His Asp Ser Gly Tyr
        595                 600
```

<210> SEQ ID NO 31
<211> LENGTH: 601
<212> TYPE: PRT
<213> ORGANISM: Glycine max
<220> FEATURE:
<223> OTHER INFORMATION: A1aB1bM5

<400> SEQUENCE: 31

Met Ala Lys Leu Val Phe Ser Leu Cys Phe Leu Leu Phe Ser Gly Cys

```
1               5                   10                  15

Cys Phe Ala Phe Ser Ser Arg Glu Gln Pro Gln Gln Asn Glu Cys Gln
                20                  25                  30

Ile Gln Lys Leu Asn Ala Leu Lys Pro Asp Asn Arg Ile Glu Ser Glu
                35                  40                  45

Gly Gly Leu Ile Glu Thr Trp Asn Pro Asn Asn Lys Pro Phe Gln Cys
            50                  55                  60

Ala Gly Val Ala Leu Ser Arg Cys Thr Leu Asn Arg Asn Ala Leu Arg
65                  70                  75                  80

Arg Pro Ser Tyr Thr Asn Gly Pro Gln Glu Ile Tyr Ile Gln Gln Gly
                85                  90                  95

Lys Gly Ile Phe Gly Met Ile Tyr Pro Gly Cys Pro Ser Thr Phe Glu
                100                 105                 110

Glu Pro Gln Gln Pro Gln Gln Arg Phe Arg His Asp Ser Gly Tyr Phe
                115                 120                 125

Arg His Asp Ser Gly Tyr Phe Arg His Asp Ser Gly Tyr Ala Gln Ser
            130                 135                 140

Ser Arg Pro Gln Asp Arg His Gln Lys Ile Tyr Asn Phe Arg Glu Gly
145                 150                 155                 160

Asp Leu Ile Ala Val Pro Thr Gly Val Ala Trp Trp Met Tyr Asn Asn
                165                 170                 175

Glu Asp Thr Pro Val Val Ala Val Ser Ile Ile Asp Thr Asn Ser Leu
                180                 185                 190

Glu Asn Gln Leu Asp Gln Met Pro Arg Arg Phe Tyr Leu Ala Gly Asn
                195                 200                 205

Gln Glu Gln Glu Phe Leu Lys Tyr Gln Gln Glu Gln Gly Gly His Gln
            210                 215                 220

Phe Arg His Asp Ser Gly Tyr Phe Arg His Asp Ser Gly Tyr Phe Arg
225                 230                 235                 240

His Asp Ser Gly Tyr Ala Gln Lys Gly Lys His Gln Gln Glu Glu Glu
                245                 250                 255

Asn Glu Gly Gly Ser Ile Leu Ser Gly Phe Thr Leu Glu Phe Leu Glu
                260                 265                 270

His Ala Phe Ser Val Asp Lys Gln Ile Ala Lys Asn Leu Gln Gly Glu
                275                 280                 285

Asn Glu Gly Glu Asp Lys Gly Ala Ile Val Thr Val Lys Gly Gly Leu
            290                 295                 300

Ser Val Ile Lys Pro Pro Thr Asp Glu Gln Gln Gln Arg Phe Arg His
305                 310                 315                 320

Asp Ser Gly Tyr Phe Arg His Asp Ser Gly Tyr Phe Arg His Asp Ser
                325                 330                 335

Gly Tyr Ala Gln Glu Glu Glu Glu Glu Asp Glu Lys Pro Gln
                340                 345                 350

Cys Lys Gly Lys Asp Lys His Cys Gln Arg Phe Arg His Asp Ser Gly
                355                 360                 365

Tyr Phe Arg His Asp Ser Gly Tyr Phe Arg His Asp Ser Gly Tyr Ala
            370                 375                 380

Arg Gly Ser Gln Ser Lys Ser Arg Asn Gly Ile Asp Glu Thr Ile
385                 390                 395                 400

Cys Thr Met Arg Leu Arg His Asn Ile Gly Gln Thr Ser Ser Pro Asp
                405                 410                 415

Ile Tyr Asn Pro Gln Ala Gly Ser Val Thr Thr Ala Thr Ser Leu Asp
                420                 425                 430
```

```
Phe Pro Ala Leu Ser Trp Leu Arg Leu Ser Ala Glu Phe Gly Ser Leu
        435                 440                 445

Arg Lys Asn Ala Met Phe Val Pro His Tyr Asn Leu Asn Ala Asn Ser
    450                 455                 460

Ile Ile Tyr Ala Leu Asn Gly Arg Ala Leu Ile Gln Val Val Asn Cys
465                 470                 475                 480

Asn Gly Glu Arg Val Phe Asp Gly Leu Gln Glu Gly Arg Val Leu
                485                 490                 495

Ile Val Pro Gln Asn Phe Val Val Ala Arg Ser Gln Ser Asp Asn
            500                 505                 510

Phe Glu Tyr Val Ser Phe Lys Thr Asn Asp Thr Pro Met Ile Gly Thr
        515                 520                 525

Leu Ala Gly Ala Asn Ser Leu Leu Asn Ala Leu Pro Glu Glu Val Ile
    530                 535                 540

Gln His Thr Phe Asn Leu Lys Ser Gln Gln Ala Arg Gln Ile Lys Asn
545                 550                 555                 560

Asn Asn Pro Phe Lys Phe Leu Val Pro Pro Gln Glu Ser Gln Lys Arg
                565                 570                 575

Ala Val Ala Gln Phe Arg His Asp Ser Gly Tyr Phe Arg His Asp Ser
            580                 585                 590

Gly Tyr Phe Arg His Asp Ser Gly Tyr
        595                 600

<210> SEQ ID NO 32
<211> LENGTH: 26
<212> TYPE: DNA
<213> ORGANISM: Artificial Sequence
<220> FEATURE:
<223> OTHER INFORMATION: Primer

<400> SEQUENCE: 32
atggccaagc tagttttttc cctttg                                          26

<210> SEQ ID NO 33
<211> LENGTH: 24
<212> TYPE: DNA
<213> ORGANISM: Artificial Sequence
<220> FEATURE:
<223> OTHER INFORMATION: Primer

<400> SEQUENCE: 33
cttgatatcg aattcctgca gccc                                            24

<210> SEQ ID NO 34
<211> LENGTH: 42
<212> TYPE: DNA
<213> ORGANISM: Artificial Sequence
<220> FEATURE:
<223> OTHER INFORMATION: 420F

<400> SEQUENCE: 34
tttagacatg attctggtta tttcagacac gatagcggct ac                        42

<210> SEQ ID NO 35
<211> LENGTH: 42
<212> TYPE: DNA
<213> ORGANISM: Artificial Sequence
<220> FEATURE:
<223> OTHER INFORMATION: 420R

<400> SEQUENCE: 35
```
gtagccgcta tcgtgtctga ataaccaga atcatgtcta aa                    42

<210> SEQ ID NO 36
<211> LENGTH: 786
<212> TYPE: DNA
<213> ORGANISM: Phaseolus vulgaris
<220> FEATURE:
<221> NAME/KEY: CDS
<222> LOCATION: (1)..(783)
<220> FEATURE:
<223> OTHER INFORMATION: Arcelin

<400> SEQUENCE: 36

```
atg gct tcc tcc aag tta ctc tcc cta gcc ctc ttc ctt gtg ctt ctc       48
Met Ala Ser Ser Lys Leu Leu Ser Leu Ala Leu Phe Leu Val Leu Leu
1               5                   10                  15 aca cac gca aac tca gcc acc gaa acc tcc ttc aat ttc cct aac ttc       96
Thr His Ala Asn Ser Ala Thr Glu Thr Ser Phe Asn Phe Pro Asn Phe
            20                  25                  30 cac aca gac gat aaa ctt atc ctc caa ggc aat gcc acc atc tca tcc      144
His Thr Asp Asp Lys Leu Ile Leu Gln Gly Asn Ala Thr Ile Ser Ser
        35                  40                  45 aaa ggc cag tta caa cta act ggt gtt gga agc aac gaa ctt ccc agg      192
Lys Gly Gln Leu Gln Leu Thr Gly Val Gly Ser Asn Glu Leu Pro Arg
    50                  55                  60 gtg gac tct ctg ggc cgc gcc ttc tac tcc gac ccc atc caa atc aag      240
Val Asp Ser Leu Gly Arg Ala Phe Tyr Ser Asp Pro Ile Gln Ile Lys
65                  70                  75                  80 gac agc aac aac gtc gcc agc ttc aac acc aac ttc aca ttc att atc      288
Asp Ser Asn Asn Val Ala Ser Phe Asn Thr Asn Phe Thr Phe Ile Ile
                85                  90                  95 cgc gct aaa aac caa agc att tcc gcc tat ggc ctt gcc ttt gct ctc      336
Arg Ala Lys Asn Gln Ser Ile Ser Ala Tyr Gly Leu Ala Phe Ala Leu
            100                 105                 110 gtc ccc gtc aac tct ccg ccc caa aaa aaa caa gaa ttt cta ggt att      384
Val Pro Val Asn Ser Pro Pro Gln Lys Lys Gln Glu Phe Leu Gly Ile
        115                 120                 125 ttc aac aca aac aac ccc gaa ccc aac gcc cgt act gtt gct gtg gtg      432
Phe Asn Thr Asn Asn Pro Glu Pro Asn Ala Arg Thr Val Ala Val Val
    130                 135                 140 ttc aac acc ttc aaa aac cgt att gat ttc gat aag aac ttc atc aag      480
Phe Asn Thr Phe Lys Asn Arg Ile Asp Phe Asp Lys Asn Phe Ile Lys
145                 150                 155                 160 cct tac gta aat gag aat tgt gat ttc cac aaa tac aac gga gaa aag      528
Pro Tyr Val Asn Glu Asn Cys Asp Phe His Lys Tyr Asn Gly Glu Lys
                165                 170                 175 acc gac gtt caa atc acc tat gac tcc tcc aac aac gac ttg agg gtt      576
Thr Asp Val Gln Ile Thr Tyr Asp Ser Ser Asn Asn Asp Leu Arg Val
            180                 185                 190 ttt ttg cat ttc act gtt tcg caa gta aag tgc agc gtc tct gcc aca      624
Phe Leu His Phe Thr Val Ser Gln Val Lys Cys Ser Val Ser Ala Thr
        195                 200                 205 gtg cac ctg gag aaa gaa gtt gac gaa tgg gtg agc gtt ggg ttc tct      672
Val His Leu Glu Lys Glu Val Asp Glu Trp Val Ser Val Gly Phe Ser
    210                 215                 220 gcc acc tca ggg ttg acg gaa gat acc act gaa acg cac gac gtg ctc      720
Ala Thr Ser Gly Leu Thr Glu Asp Thr Thr Glu Thr His Asp Val Leu
225                 230                 235                 240 tct tgg tca ttt tct tcc aag ttc cga aac aaa ctt tcc aac atc ctc      768
Ser Trp Ser Phe Ser Ser Lys Phe Arg Asn Lys Leu Ser Asn Ile Leu
                245                 250                 255
```

```
ctc aac aat atc ctc tag                                          786
Leu Asn Asn Ile Leu
        260

<210> SEQ ID NO 37
<211> LENGTH: 261
<212> TYPE: PRT
<213> ORGANISM: Phaseolus vulgaris
<220> FEATURE:
<223> OTHER INFORMATION: Arcelin

<400> SEQUENCE: 37

Met Ala Ser Ser Lys Leu Leu Ser Leu Ala Leu Phe Leu Val Leu Leu
1               5                   10                  15

Thr His Ala Asn Ser Ala Thr Glu Thr Ser Phe Asn Phe Pro Asn Phe
            20                  25                  30

His Thr Asp Asp Lys Leu Ile Leu Gln Gly Asn Ala Thr Ile Ser Ser
        35                  40                  45

Lys Gly Gln Leu Gln Leu Thr Gly Val Gly Ser Asn Glu Leu Pro Arg
    50                  55                  60

Val Asp Ser Leu Gly Arg Ala Phe Tyr Ser Asp Pro Ile Gln Ile Lys
65                  70                  75                  80

Asp Ser Asn Asn Val Ala Ser Phe Asn Thr Asn Phe Thr Phe Ile Ile
                85                  90                  95

Arg Ala Lys Asn Gln Ser Ile Ser Ala Tyr Gly Leu Ala Phe Ala Leu
            100                 105                 110

Val Pro Val Asn Ser Pro Pro Gln Lys Lys Gln Glu Phe Leu Gly Ile
        115                 120                 125

Phe Asn Thr Asn Asn Pro Glu Pro Asn Ala Arg Thr Val Ala Val Val
130                 135                 140

Phe Asn Thr Phe Lys Asn Arg Ile Asp Phe Asp Lys Asn Phe Ile Lys
145                 150                 155                 160

Pro Tyr Val Asn Glu Asn Cys Asp Phe His Lys Tyr Asn Gly Glu Lys
                165                 170                 175

Thr Asp Val Gln Ile Thr Tyr Asp Ser Ser Asn Asn Asp Leu Arg Val
            180                 185                 190

Phe Leu His Phe Thr Val Ser Gln Val Lys Cys Ser Val Ser Ala Thr
        195                 200                 205

Val His Leu Glu Lys Glu Val Asp Glu Trp Val Ser Val Gly Phe Ser
    210                 215                 220

Ala Thr Ser Gly Leu Thr Glu Asp Thr Thr Glu Thr His Asp Val Leu
225                 230                 235                 240

Ser Trp Ser Phe Ser Ser Lys Phe Arg Asn Lys Leu Ser Asn Ile Leu
                245                 250                 255

Leu Asn Asn Ile Leu
        260

<210> SEQ ID NO 38
<211> LENGTH: 27
<212> TYPE: DNA
<213> ORGANISM: Artificial Sequence
<220> FEATURE:
<223> OTHER INFORMATION: Primer

<400> SEQUENCE: 38
aaccgtattg atttcgataa gaacttc                                    27
```

```
<210> SEQ ID NO 39
<211> LENGTH: 27
<212> TYPE: DNA
<213> ORGANISM: Artificial Sequence
<220> FEATURE:
<223> OTHER INFORMATION: Primer

<400> SEQUENCE: 39
tttgaaggtg ttgaacacca cagcaac                                         27

<210> SEQ ID NO 40
<211> LENGTH: 24
<212> TYPE: DNA
<213> ORGANISM: Artificial Sequence
<220> FEATURE:
<223> OTHER INFORMATION: Primer

<400> SEQUENCE: 40
aaactttcca acatcctcct caac                                            24

<210> SEQ ID NO 41
<211> LENGTH: 25
<212> TYPE: DNA
<213> ORGANISM: Artificial Sequence
<220> FEATURE:
<223> OTHER INFORMATION: Primer

<400> SEQUENCE: 41
gtttcggaac ttggaagaaa atgac                                           25

<210> SEQ ID NO 42
<211> LENGTH: 23
<212> TYPE: DNA
<213> ORGANISM: Artificial Sequence
<220> FEATURE:
<223> OTHER INFORMATION: Primer

<400> SEQUENCE: 42
atggcttcct ccaagttact ctc                                             23

<210> SEQ ID NO 43
<211> LENGTH: 23
<212> TYPE: DNA
<213> ORGANISM: Artificial Sequence
<220> FEATURE:
<223> OTHER INFORMATION: Primer

<400> SEQUENCE: 43
tctagaggat attgttgagg agg                                             23

<210> SEQ ID NO 44
<211> LENGTH: 405
<212> TYPE: DNA
<213> ORGANISM: Oriza sativa
<220> FEATURE:
<221> NAME/KEY: CDS
<222> LOCATION: (1)..(402)
<220> FEATURE:
<223> OTHER INFORMATION: Prolamin

<400> SEQUENCE: 44 atg gca gca tac acc agc aag atc ttt gcc ctg ttt gcc tta att gct     48
Met Ala Ala Tyr Thr Ser Lys Ile Phe Ala Leu Phe Ala Leu Ile Ala
1               5                   10                  15 ctt tct gca agt gcc act act gca atc acc act atg cag tat ttc cca     96
Leu Ser Ala Ser Ala Thr Thr Ala Ile Thr Thr Met Gln Tyr Phe Pro
            20                  25                  30
```

```
cca aca tta gcc atg ggc acc atg gat ccg tgt agg cag tac atg atg        144
Pro Thr Leu Ala Met Gly Thr Met Asp Pro Cys Arg Gln Tyr Met Met
        35                  40                  45 caa acg ttg ggc atg ggt agc tcc aca gcc atg ttc atg tcg cag cca        192
Gln Thr Leu Gly Met Gly Ser Ser Thr Ala Met Phe Met Ser Gln Pro
 50                  55                  60 atg gcg ctc ctg cag cag caa tgt tgc atg cag cta caa ggc atg atg        240
Met Ala Leu Leu Gln Gln Gln Cys Cys Met Gln Leu Gln Gly Met Met
 65                  70                  75                  80 cct cag tgc cac tgt ggc acc agt tgc cag atg atg cag agc atg caa        288
Pro Gln Cys His Cys Gly Thr Ser Cys Gln Met Met Gln Ser Met Gln
                 85                  90                  95 caa gtt att tgt gct gga ctc ggg cag cag cag atg atg aag atg gcg        336
Gln Val Ile Cys Ala Gly Leu Gly Gln Gln Gln Met Met Lys Met Ala
            100                 105                 110 atg cag atg cca tac atg tgc aac atg gcc cct gtc aac ttc caa ctc        384
Met Gln Met Pro Tyr Met Cys Asn Met Ala Pro Val Asn Phe Gln Leu
        115                 120                 125 tct tcc tgt ggt tgt tgt tga                                            405
Ser Ser Cys Gly Cys Cys
        130
```

<210> SEQ ID NO 45
<211> LENGTH: 134
<212> TYPE: PRT
<213> ORGANISM: Oriza sativa
<220> FEATURE:
<223> OTHER INFORMATION: Prolamin

<400> SEQUENCE: 45

```
Met Ala Ala Tyr Thr Ser Lys Ile Phe Ala Leu Phe Ala Leu Ile Ala
1               5                   10                  15

Leu Ser Ala Ser Ala Thr Thr Ala Ile Thr Thr Met Gln Tyr Phe Pro
            20                  25                  30

Pro Thr Leu Ala Met Gly Thr Met Asp Pro Cys Arg Gln Tyr Met Met
        35                  40                  45

Gln Thr Leu Gly Met Gly Ser Ser Thr Ala Met Phe Met Ser Gln Pro
 50                  55                  60

Met Ala Leu Leu Gln Gln Gln Cys Cys Met Gln Leu Gln Gly Met Met
 65                  70                  75                  80

Pro Gln Cys His Cys Gly Thr Ser Cys Gln Met Met Gln Ser Met Gln
                 85                  90                  95

Gln Val Ile Cys Ala Gly Leu Gly Gln Gln Gln Met Met Lys Met Ala
            100                 105                 110

Met Gln Met Pro Tyr Met Cys Asn Met Ala Pro Val Asn Phe Gln Leu
        115                 120                 125

Ser Ser Cys Gly Cys Cys
        130
```

<210> SEQ ID NO 46
<211> LENGTH: 24
<212> TYPE: DNA
<213> ORGANISM: Artificial Sequence
<220> FEATURE:
<223> OTHER INFORMATION: Primer

<400> SEQUENCE: 46
atggcgatgc agatgccata catg                                              24

<210> SEQ ID NO 47
<211> LENGTH: 27
<212> TYPE: DNA
<213> ORGANISM: Artificial Sequence
<220> FEATURE:
<223> OTHER INFORMATION: Primer

<400> SEQUENCE: 47
cttcatcatc tgctgctgcc cgagtcc                                        27

<210> SEQ ID NO 48
<211> LENGTH: 24
<212> TYPE: DNA
<213> ORGANISM: Artificial Sequence
<220> FEATURE:
<223> OTHER INFORMATION: Primer

<400> SEQUENCE: 48
atggcagcat acaccagcaa gatc                                           24

<210> SEQ ID NO 49
<211> LENGTH: 22
<212> TYPE: DNA
<213> ORGANISM: Artificial Sequence
<220> FEATURE:
<223> OTHER INFORMATION: Primer

<400> SEQUENCE: 49 tcaacaacaac cacaggaaga g                                             22

<210> SEQ ID NO 50
<211> LENGTH: 23
<212> TYPE: DNA
<213> ORGANISM: Artificial Sequence
<220> FEATURE:
<223> OTHER INFORMATION: primer SP1

<400> SEQUENCE: 50
ttggttttgt tgaacgtctc gac                                            23

<210> SEQ ID NO 51
<211> LENGTH: 22
<212> TYPE: DNA
<213> ORGANISM: Artificial Sequence
<220> FEATURE:
<223> OTHER INFORMATION: primer SP2

<400> SEQUENCE: 51
ggtgagaagc acaaggaaga gg                                             22

<210> SEQ ID NO 52
<211> LENGTH: 26
<212> TYPE: DNA
<213> ORGANISM: Artificial Sequence
<220> FEATURE:
<223> OTHER INFORMATION: primer second SP1

<400> SEQUENCE: 52 cagattttt gccctcaaaa ttgatg                                          26

<210> SEQ ID NO 53
<211> LENGTH: 22
<212> TYPE: DNA
<213> ORGANISM: Artificial Sequence
<220> FEATURE:
<223> OTHER INFORMATION: primer second SP2

<400> SEQUENCE: 53
cggatgtgcg tggactacaa gg                                       22

<210> SEQ ID NO 54
<211> LENGTH: 25
<212> TYPE: DNA
<213> ORGANISM: Artificial Sequence
<220> FEATURE:
<223> OTHER INFORMATION: primer third SP1

<400> SEQUENCE: 54
cgacctgaag aacgcagcgg cgacc                                    25

<210> SEQ ID NO 55
<211> LENGTH: 24
<212> TYPE: DNA
<213> ORGANISM: Artificial Sequence
<220> FEATURE:
<223> OTHER INFORMATION: primer third SP2

<400> SEQUENCE: 55
taccagcagt tgatggacaa gatc                                     24

<210> SEQ ID NO 56
<211> LENGTH: 3860
<212> TYPE: DNA
<213> ORGANISM: Phaseolus vulgaris

<400> SEQUENCE: 56
tctagacatc agcagcagaa ttataaacat tcaagaaaat agagtttggc agagtttaag      60
aacaacacaa aaacaaaata atctccccat atttgtcttc acaaatagac tttaggaaga     120
gagaaaacat aattgttcca gataaaacaa aatatagaaa gaaagagcaa caaagcattg     180
acagattgac aaaacaattg gttgtttcga gagatcaacc agttgttttt cttcagtctt     240
cctttccata ctgtagctca aaaatatgat tcttaacggc ttcaatctgt tcatcaaggg     300
tctaaaagtg agtgtccata ctctggaata tgttgtcaaa gttcttaaag tttgagacac     360
aaagatcatg aagattcctt tgattttccg caaagtcatc aagcctatcc accatgtatc     420
tttcaaagga agacattgag ggagtcccat ctccttgatg tcaaacactt gtcccagcac     480
caaagtcaat tgcaggttgt tctacatctt gaacattcat atcagcacct tcttgatctt     540
tgtcatcatt ttcagcttga gcagcacttg aggaaccacc atgttcacca tccttgctta     600
cgcatcttcc attgatcttg gtaaaaccca tcttgcttag tgcaccattg ttcacttcaa     660
gagttgattt caccaactca gatgtttcat cctcaagatt cacttcaaaa tagagtaaaa     720
acttagaaat caagacaaca taaggataat ggtaatcact taacctcatt gaattttgca     780
tatgctcctt gatgatatga atccaattga tcttgacttt gttcatgatg caatagatat     840
agacaaggtc ttcctcagtt aaaacaggat ctagctgtta aaatccatgt aacaatgaga     900
gctaacaacc tttgatctaa cttcaaacct ccaacagaac aaattcttat ttgagtttga     960 ggattttta aacagcttct atagtactga actttgttaa acttttccac cacaccaatt    1020
tttcctttat tgattctcag cccaacatat ttcaaacaag ttacagcagc ccatacatca    1080
tgggtaatct ccatatctac ccccttaaca tgagaaacaa gattgttacc ttcaaacttc    1140
aaatttgtgt agaaaacccg aattagatat ggatatatgt tccccttcat ctccaagaac    1200
ctcttcaaca attgttcctt gagaatcctc ctcacattgt ccagttttttg gttttttcaac    1260 taatcaaagg agacaacttt agggttgttt atcacttttc tacttgtttc aaagcgatac    1320

```
ttctcaatca gttcattatc tcccaaaaac cagccctcaa gacgtgctcc tgatctcaca    1380 acctaattt taatcctttt tgatgtaggt ggagtggaat ccatggaagc aaaatgagaa     1440
aagggcacac acacaaggag agaaagagat gtagcaagag atgagccaat gagttgtttt    1500
tgtgaaggaa aatagcttca acagatttta taggaaagca aaatccctct tcgatccttt    1560
ggtggtagtg gatttcagtc ttcaaggtag aaaactggtc caagccttgc acaaaaaacg    1620
ttaacataga gcagaaaaac acatgtgact tttgactaga cataaaggct cttgaatttc    1680
caagatatgg aatatattcc tttatgacaa catgtaactt ccttcagaac caaatcaggc    1740
tttcaagact gctttattga cttaaagact cattaagatt tgaatctgca aaagatagaa    1800
tgcatgaaga aattaaatca attcttcaca gtgttgtcag agaagaaaca atcggttgtt    1860
tcgaggaaac aatcaattgt ttttctgcag caacaacagt atttgtattt taaacagaat    1920
ctgaaaagag tttaaaatat atgttatttc tcttatgtag atgaagaatt tgatatgaat    1980
ttataaattg aaaaacagag atatggaagg tcttatcctt ttatgaagtt ccttcaatga    2040
gtcattgttt gtgatccaga atgctctttt ttttcctttc aagacatctt ggactggtac    2100
acaaccttaa ttcagttcca ttcacacttc ttttcttcca aggacttgat aggataactc    2160
aggacttcat gtttctctag tatccttgca tcaaaatgaa ttcaagcaac aagatttggt    2220
ccccttacaa atgtgggtcc ttttgattta tctttatcct ttgaaacctc acaacttttg    2280
ggaatccatt gtaaaatacc tttaggaact gaatatttcc tgattttaca gaattctatt    2340
aggattttca agaaacaat tggtagaaac cacgaaacaa ccgattgttt ggtttgacag     2400
ttaagtcaac caaacttaaa cagttttcaa ccttttcaaa aactcctaag agtaaaaaat    2460
cggttgatta gacaaaacaa caggttgttt ttcacttagt ttcaaaacac tttgtttcaa    2520
aaaagattta aaacacatca gctttagatt caacaaagga gtggattaca tataaaacta    2580
ctcagatccc tcccaaaaca caacagcaac acaaccttgc atcaagcacg aagggtttgg    2640
attcttcaaa gcacaatttg aattcttcaa agcacttgat cactcttgat caacatgttg    2700
gtcctcctca aaccataaaa gacttcttgc aagtctttga tgtgttggcc gcactagcca    2760
gatttgacca caatgtcgtc cgcgtagacc tccacgcttc gaccgatcat cccttgaag    2820 atcttgtcca tcaactgctg gtaggtcgcc gctgcgttct tcaggtcgaa caacattacc    2880
tcatagaagt agtttgcacc gtcggtcgtg aaaatcgttt tctccttgtc cctgggatgc    2940
atgcttatct ggttgtagcc agagtaagcg tccaggaagc tcaatatctt gtacccggcc    3000
gcaccatcaa cgatttgatc aatgttaggc aaggggtagg agtcctttgg acacgccttg    3060
gtttaagtcc ttgtagtcca cgcacatccg ccatatatca ttggacttgg tgaccatgac    3120
cacattagcc aaccaggttg tgtaccaggc ttctcgaatg aacccggctt ttaggagctt    3180
attggcctct tcctggccgc gagccttttg tcttccccat gatttctctt cttctgaacg    3240
accgagcgcg cctctttgta gactaagagt ctatgggtta tgacctcagg ttaacacct    3300 gacacctcag cggccgacca aacgaagata tcgatatttt tattcaaagc ctggtgtata    3360
agctcggcgt caacggctgc cataaataat ttttttaatt tcaatatttt ataaattttt    3420
taatttaaat tttcatgtgc cttcctctca ctttccagta catctttcac tatgacccaa    3480
atgccatgca cgctgccacc tcagctcctt cctcttccta tgatgacacc actgggcatg    3540
catgctgcca cctcagctcc cacctcttct cattatgaga ctactggcca tgcacactgc    3600
cacgtgagct ccctcctctt cacatgtggc ttcctctcac ttcccactac taggtgccaa    3660
```

```
<210> SEQ ID NO 57
<211> LENGTH: 26
<212> TYPE: DNA
<213> ORGANISM: Artificial Sequence
<220> FEATURE:
<223> OTHER INFORMATION: primer SP3

<400> SEQUENCE: 57
catcaatttt gagggcaaaa aatctg                                              26

<210> SEQ ID NO 58
<211> LENGTH: 27
<212> TYPE: DNA
<213> ORGANISM: Artificial Sequence
<220> FEATURE:
<223> OTHER INFORMATION: primer SP4

<400> SEQUENCE: 58
cgttccaaca tcctcctcaa caagatc                                             27

<210> SEQ ID NO 59
<211> LENGTH: 795
<212> TYPE: DNA
<213> ORGANISM: Phaseolus vulgaris

<400> SEQUENCE: 59
actcccaaag ccagcttcac tgtgacagta aaaccttcct tatacgctaa taatgttcat          60
ctgtcacaca aactacaata aataaaatgg gagcaataaa taaaatggga gctcatatat         120
ttacacaatt tacactgcct attattcacc atgccaatta ttactgcata atttcaaaat         180
tgtcattttt taaaagttta taataattaa gaaatattac tataagttaa agtataacat         240
agaaaaaaaa aaacattaaa tcttaagaaa tattactata atttacccct ttttatctga         300
agagtctaat aattgagaga ttgacacaaa atatttatac cagcccctc tttaccaaga          360
gctacattca gtcttcgaac ccactaagaa ttcattaact aatcaacctt gattactaac         420
aattcaccat gccatttatt actgcataat ccttttatct caaagaacaa gaaaaacttt         480
aattcctctt accttattct tctttcaagt cttgtaatca aaatctcaaa aaatattcaa         540
atcattattt atttcaactt tgtgattttt taaattaact ttttatttat tgttcttgaa         600
cgaagttggg gcctatagaa ctattaagat cactcttcct tcgtcggtcg gtcgaattgt         660
acttcagctt ccctcctcgc aagctctctc cccctcctta ctcgtctcac ctcttggtct         720
tctcgtagtc tagactcgga tggtacctgc agaaggcact ccgacgctca agtcagtaaa         780
ggtattcagt gctag                                                          795

<210> SEQ ID NO 60
<211> LENGTH: 14
<212> TYPE: PRT
<213> ORGANISM: Artificial Sequence
<220> FEATURE:
<223> OTHER INFORMATION: Abeta4-10X2

<400> SEQUENCE: 60

Phe Arg His Asp Ser Gly Tyr Phe Arg His Asp Ser Gly Tyr
```

-continued 1 5 10

<210> SEQ ID NO 61
<211> LENGTH: 21
<212> TYPE: PRT
<213> ORGANISM: Artificial Sequence
<220> FEATURE:
<223> OTHER INFORMATION: Abeta4-10X3

<400> SEQUENCE: 61

Phe Arg His Asp Ser Gly Tyr Phe Arg His Asp Ser Gly Tyr Phe Arg
1 5 10 15

His Asp Ser Gly Tyr
20

TRANSFORMED SOYBEAN PLANT WHICH ACCUMULATES VACCINE, AND USE THEREOF

CROSS-REFERENCE TO RELATED APPLICATIONS

This application is the U.S. National Phase under 35 U.S.C. §371 of International Application PCT/JP2009/069977, filed Nov. 26, 2009, which was published in a non-English language, which claims priority to JP Patent Application No. 2008-304006, filed Nov. 28, 2008.

TECHNICAL FIELD

The present invention relates to a transformed soybean plant which accumulates an Alzheimer's disease vaccine in its seeds, and use thereof.

BACKGROUND ART

Alzheimer's disease is a neurodegenerative disease caused by accumulation of a causative substance such as β-amyloid in brain, causing damage to nerve cells. Although the number of patients suffering from Alzheimer's disease is expected to increase upon the advent of an aging society, prophylactic agents and therapeutic agents for the disease are hardly available, and development of new prophylactic agents, therapeutic agents, vaccines and the like has been demanded. Vaccines against Alzheimer's disease have been developed using β-amyloid, which is a causative substance of the disease, as an antigen, but development of the vaccines was difficult because of problems such as side effects. Therefore, development of a vaccine using a β-amyloid antigenic determinant (epitope) which does not cause side effects, and establishment of mass production techniques for the vaccine are required.

Soybean is an exalbuminous seed, which does not have albumen and accumulates its nutrition in the germ corresponding to the cotyledon. About 40% of the whole volume of a seed, which corresponds to the germ, is occupied by storage proteins. Therefore, soybean has characteristics as a storage tissue different from those of other crops such as rice and maize that accumulate starch in albumen as a major reserve substance, so that it is a crop suitable for being made to produce and accumulate an exogenous protein. The major seed storage proteins in soybean are 11S globulin (glycinin) and 7S globulin (β-conglycinin). The spatial structures of these seed storage proteins and the mechanisms of their accumulation in the cell have been elucidated, and it is known that the genes encoding them have portions called variable regions. It is thought that the spatial structures of the proteins can be maintained even after insertion of an exogenous gene into the variable regions and that the properties of the storage proteins are not affected by such insertion.

In general, a β-amyloid antigenic determinant is a protein (peptide) having a relatively low molecular weight composed of several amino acids, and it has been difficult to make the peptide highly accumulated in seeds of a transformed soybean for the purpose of mass production of the peptide by introducing a gene encoding the peptide to the soybean, since the peptide was degraded by enzymes such as proteases in the cells.

On the other hand, as transformed crops that accumulate biologically active peptides and vaccines in their seeds, a transformed soybean that accumulates a hypotensive peptide (Patent Document 1), a transformed rice that accumulates a vaccine against allergy to cedar pollen (Patent Document 2), a potato that produces β-amyloid (Non-patent Document 1) and a tomato that produces β-amyloid (Non-patent Document 2) are known.

However, a transformed soybean that highly accumulates an Alzheimer's disease vaccine composed of a β-amyloid antigenic determinant (epitope), and mass production techniques for the vaccine using the soybean have not been known so far.

Common bean is a plant belonging to Leguminosae, to which soybean also belongs, and the content of protein in a seed of common bean is 20%. It is known that arcelin, which is one of the major seed storage proteins in common bean, can be divided into plural types, that is, arcelin 1 to 7, and that the homologies among the nucleotide sequences of the part encoding their structural proteins are high. The structures of the arcelin proteins in common bean have been less analyzed compared to those in soybean, and only the spatial structures of arcelin 1 and 5 have been revealed.

Further, it is known that prolamin, which is one of the major seed storage proteins in rice, is an indigestible protein which can be divided into several types (e.g., 10K, 13K and 16K) having different molecular weights. The spatial structure of prolamin has not been revealed.

PRIOR ART DOCUMENTS

Patent Documents

Patent Document 1: JP 2006-238821 A
Patent Document 2: JP 2004-321079 A

Non-Patent Documents

Non-patent Document 1: Federation of European Biochemical Societies (2005) vol. 579, pp. 6737-6744.
Non-patent Document 2: Biotechnology Letters (2008) vol. 30, pp. 1839-1845.

DISCLOSURE OF THE INVENTION

The present invention aims to provide a transformed soybean plant which can be made to produce and accumulate an Alzheimer's disease vaccine in its seeds. Further, the present invention aims to provide a method for producing an Alzheimer's disease vaccine using the transformed soybean.

The present inventors intensively studied to solve the above problems.

As a result, the present inventors succeeded in preparation of a transformed soybean plant having a gene encoding a modified seed storage protein introduced therein, which gene has been obtained by inserting a gene encoding an Alzheimer's disease vaccine to a variable region(s) of a gene encoding a wild-type seed storage protein, and also succeeded in production and accumulation of the Alzheimer's disease vaccine in seeds of the transformed soybean plant.

Further, the present inventors discovered that a transformed soybean plant produced by introducing the gene encoding a modified seed storage protein to soybean in which an endogenous seed storage protein(s) is/are deficient can efficiently produce and accumulate the Alzheimer's disease vaccine in its seeds.

That is, the present invention provides:
[1] A transformed soybean plant having an introduced gene encoding a modified seed storage protein, which gene encoding a modified seed storage protein was produced by inserting a gene encoding an Alzheimer's disease vaccine to a variable region(s) of a gene encoding a wild-type seed storage protein such that frameshift does not occur, which modified seed storage protein is expressed in a seed and accumulates therein.

[2] The transformed soybean plant according to [1], wherein the Alzheimer's disease vaccine is a β-amyloid antigenic determinant.

[3] The transformed soybean plant according to [2], wherein the β-amyloid antigenic determinant has a sequence having one to three copies of the peptide having the sequence shown in SEQ ID NO:3 which are linked to each other.

[4] The transformed soybean plant according to any one of [1] to [3], wherein endogenous soybean 11S globulin and/or soybean 7S globulin is/are deficient.

[5] The transformed soybean plant according to any one of [1] to [4], wherein the wild-type seed storage protein is the A1aB1b subunit of soybean 11S globulin, arcelin of common bean, or prolamin of rice.

[6] The transformed soybean plant according to [5], wherein the wild-type seed storage protein contains the amino acid sequence shown in SEQ ID NO:2 or an amino acid sequence having an identity of not less than 90% to the amino acid sequence shown in SEQ ID NO:2, and the variable region(s) to which the gene encoding an Alzheimer's disease vaccine was inserted is/are the region(s) encoding one or more amino acid sequence(s) selected from the group consisting of the amino acid sequences corresponding to amino acid positions 111-128, amino acid positions 198-216, amino acid positions 268-315 and amino acid positions 490-495 in SEQ ID NO:2.

[7] The transformed soybean plant according to [5], wherein the wild-type seed storage protein contains the amino acid sequence shown in SEQ ID NO:37 or an amino acid sequence having an identity of not less than 90% to the amino acid sequence shown in SEQ ID NO:37, and the variable region(s) to which the gene encoding an Alzheimer's disease vaccine was inserted is/are the region(s) encoding the amino acid sequence(s) corresponding to amino acid positions 149-150 and/or amino acid positions 250-251 in SEQ ID NO:37.

[8] The transformed soybean plant according to [5], wherein the wild-type seed storage protein contains the amino acid sequence shown in SEQ ID NO:45 or an amino acid sequence having an identity of not less than 90% to the amino acid sequence shown in SEQ ID NO:45, and the variable region to which the gene encoding an Alzheimer's disease vaccine was inserted is the region encoding the amino acid sequence corresponding to amino acid positions 110-111 in SEQ ID NO:45.

[9] The transformed soybean plant according to any one of [1] to [8], wherein expression of the gene encoding a modified seed storage protein is regulated by the promoter of common bean arcelin 2 or the promoter of the A1aB1b subunit of soybean 11S globulin.

[10] A cell of the transformed soybean plant according to any one of [1] to [9].

[11] A seed of the transformed soybean plant according to any one of [1] to [9].

[12] A processed soybean seed produced by processing the seed according to [11].

[13] A method for producing an Alzheimer's disease vaccine using the transformed soybean plant according to any one of [1] to [9], which Alzheimer's disease vaccine is produced in a seed of the transformed soybean plant.

[14] A vector comprising:
- a promoter which induces soybean seed-specific expression; and
- a gene encoding a modified seed storage protein produced by inserting a gene encoding an Alzheimer's disease vaccine to a variable region(s) of a gene encoding a wild-type seed storage protein such that frameshift does not occur, which gene encoding a modified seed storage protein is linked to the downstream of the promoter.

[15] The vector according to [14], wherein the promoter is the promoter of common bean arcelin 2 or the promoter of the A1aB1b subunit of soybean 11S globulin.

Since the transformed soybean plant of the present invention can highly accumulate an Alzheimer's disease vaccine in its seeds, the Alzheimer's disease vaccine can be efficiently produced using the transformed soybean plant.

BRIEF DESCRIPTION OF THE DRAWINGS

FIG. 1 is a schematic diagram showing the amino acid sequences encoded by the variable regions in the amino acid sequence of the A1aB 1b subunit of soybean glycinin (SEQ ID NO: 2).

FIG. 2 is a diagram showing the construction procedure for a plasmid pUHGA1aB1bM.

FIG. 3 is a schematic diagram showing the structure of the plasmid pUHG which was used for incorporation of a gene encoding a modified seed storage protein. The gene of an arbitrary modified seed storage protein is inserted into the SmaI site.

FIG. 4 shows photographs showing detection of accumulation of a β-amyloid antigenic determinant in seeds of a transformed soybean to which a gene encoding a modified A1aB1M1 was introduced, which detection was carried out by Western blotting. The samples in the respective lanes are as follows. 1: Transformed soybean 10-2 No. 1 produced by introducing A1aB1M1 to variety Jack; 2: transformed soybean 10-2 No. 2 produced by introducing A1aB1M1 to variety Jack; 3: transformed soybean 10-2 No. 3 produced by introducing A1aB1M1 to variety Jack; 4: variety Jack (control); 5: transformed soybean 16-2 No. 1 produced by introducing A1aB1M1 to a storage protein-deficient line; 6: transformed soybean 16-2 No. 2 produced by introducing A1aB1M1 to a storage protein-deficient line; 7: transformed soybean 16-2 No. 3 produced by introducing A1aB1M1 to a storage protein-deficient line; and 8: a storage protein-deficient line (control).

FIG. 5 shows photographs showing detection of accumulation of β-amyloid antigenic determinant in seeds of a transformed soybean to which a gene encoding modified arcelin (Arc5M1) was introduced, which detection was carried out by Western blotting. The samples in the respective lanes are as follows. 1: Transformed soybean 2-1 No. 1 produced by introducing Arc5M1 to variety Jack; 2: transformed soybean 2-1 No. 2 produced by introducing Arc5M1 to variety Jack; 3: transformed soybean 2-2 No. 1 produced by introducing Arc5M1 to variety Jack; and 4: transformed soybean 2-2 No. 2 produced by introducing Arc5M1 to variety Jack.

FIG. 6 shows a photograph showing detection of accumulation of a β-amyloid antigenic determinant in seeds of a transformed soybean to which a gene encoding modified prolamin (PR10M1) was introduced, which detection was carried out by Western blotting. The samples in the respective lanes are as follows. 1: Transformed soybean 1-1 No. 1 produced by introducing PR10M1 to variety Jack; 2: transformed soybean 1-1 No. 2 produced by introducing PR10M1 to variety Jack; 3: transformed soybean 4-2 No. 1 produced by introducing PR10M1 to variety Jack; and 4: transformed soybean 4-2 No. 2 produced by introducing PR10M1 to variety Jack.

Figure 7:
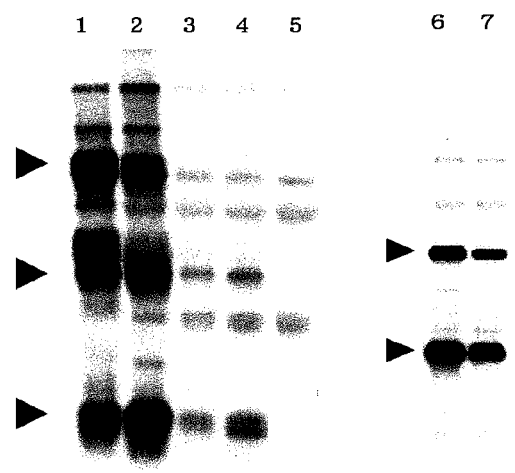

FIG. 7 shows photographs showing detection of accumulation of a β-amyloid antigenic determinant in seeds of a transformed soybean to which a gene encoding modified A1aB1M1 or A2PA1aB1bM3 was introduced, which detection was carried out by Western blotting. The samples in the respective lanes are as follows. 1: transformed soybean line 4-6 produced by introducing A2PA1aB1bM1 to a storage protein-deficient line; 2: transformed soybean line 7-1 produced by introducing A1aB1bM1 to a storage protein-deficient line; 3: transformed soybean line 8-1 No. 1 produced by introducing A1aB1bM1 to variety Jack; 4: transformed soybean line 8-1 No. 2 produced by introducing A1aB1bM1 to variety Jack; 5: storage protein-deficient line; 6: transformed soybean line 3-1 No. 1 produced by introducing A2PA1aB1bM3 to a storage protein-deficient line; and 7: transformed soybean line 3-1 No. 2 produced by introducing A2PA1aB1bM3 to a storage protein-deficient line.

Figure 8:

FIG. 8 shows a diagram (photographs) showing the results of a stability assay of Aβ4-10 (the peptide having the amino acid sequence shown in SEQ ID NO:3) in seeds of the transformed soybean A1aB1bM3. The samples in the respective lanes are as follows. A-1, A-2: heat-untreated group; B-1, B-2: roasted group; C-1, C-2: water-boiled group; D-1, D-2: heat-treated extract group.

Figure 9:
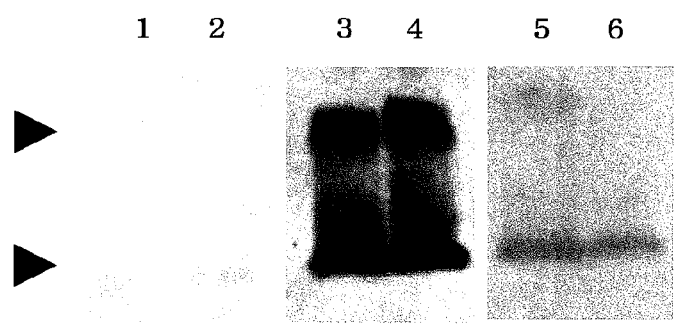

FIG. 9 shows a diagram (photographs) showing evaluation of the relationship between the repeat number o f Aβ4-10 and the antibody titer. The samples in the respective lanes are as follows. 1: Reaction group in which purified antibody key-limpet-hemocyanin (KLH)-P1 was allowed to react with substrate Aβ2 (400 picomoles); 2: reaction group in which purified antibody KLH-P1 was allowed to react with substrate Aβ42 (1000 picomoles); 3: reaction group in which purified antibody KLH-P2 was allowed to react with substrate Aβ42 (400 picomoles); 4: reaction group in which purified antibody KLH-P2 was allowed to react with substrate Aβ42 (1000 picomoles); 5: reaction group in which purified antibody KLH-P3 was allowed to react with substrate Aβ42 (400 picomoles); and 6: reaction group in which purified antibody KLH-P3 was allowed to react with substrate Aβ42 (1000 picomoles).

MODES FOR CARRYING OUT THE INVENTION

The present invention will now be described in detail.
1. Gene Encoding Wild-Type Seed Storage Protein Examples of the wild-type seed storage protein in the present invention include the respective subunits constituting soybean 11S globulin, the respective subunits constituting soybean 7S globulin, arcelin in common bean, prolamin in rice, globulin in rice, and further, seed storage proteins in other crops. Preferred examples of the wild-type seed storage protein include the A1aB1b subunit of 11S globulin and the α subunit and β subunit of 7S globulin in soybean, among which the A1aB1b subunit of 11S globulin in soybean is more preferred.

Further, examples of the wild-type seed storage protein in the present invention include proteins containing the amino acid sequences shown in SEQ ID NO:2, SEQ ID NO:37 and SEQ ID NO:45, and proteins containing amino acid sequences having identities of not less than 80%, preferably not less than 90%, more preferably not less than 95% to these amino acid sequences.

Here, the identity (%) between amino acid sequences means the maximum identity (%) between the amino acid sequences which is obtained by aligning the two amino acid sequences to be compared while introducing, as required, gaps thereto (alignment). The alignment for the purpose of determining the identity between amino acid sequences can be carried out using various methods which are well-known to those skilled in the art. For example, publicly available computer software such as BLAST, BLAST-2, ALIGN and Megalign (DNASTAR) software and commercially available software such as Gene Works 2.5.1 software (Teijin System Technology, Inc.) and GENETIX-WIN (Software Development Co., Ltd) may be used.

Examples of the gene encoding a wild-type seed storage protein in the present invention include genes encoding the respective subunits constituting soybean 11S globulin, genes encoding the respective subunits constituting soybean 7S globulin, a gene encoding arcelin in common bean, a gene encoding prolamin in rice, a gene encoding globulin in rice, and further, genes encoding seed storage proteins in other crops. Preferred examples of the gene include a gene encoding the A1aB1b subunit of 11S globulin and genes encoding the α subunit and β subunit of 7S globulin in soybean, among which a gene encoding the A1aB1b subunit of 11S globulin in soybean is more preferred.

Further, examples of the gene encoding a wild-type seed storage protein in the present invention include genes containing the nucleotide sequences shown in SEQ ID NO:1, SEQ ID NO:36 and SEQ ID NO:44, and genes containing nucleotide sequences having identities of not less than 80%, preferably not less than 90%, more preferably not less than 95% to these nucleotide sequences.

Here, the identity (%) between nucleotide sequences means the maximum identity (%) between the nucleotide sequences which is obtained by aligning the two nucleotide sequences to be compared while introducing, as required, gaps thereto (alignment). The alignment for the purpose of determining the identity between nucleotide sequences can be carried out using various methods which are well-known to those skilled in the art. For example, publicly available computer software such as BLAST, BLAST-2, ALIGN and Megalign (DNASTAR) software and commercially available software such as Gene Works 2.5.1 software (Teijin System Technology, Inc.) and GENETIX-WIN (Software Development Co., Ltd) may be used.

2. Gene Encoding Modified Seed Storage Protein

The gene encoding a modified seed storage protein in the present invention means a gene produced by inserting a gene encoding an Alzheimer's disease vaccine to a variable region(s) of a gene encoding a wild-type seed storage protein such that frameshift does not occur.

Here, "inserting a gene encoding an Alzheimer's disease vaccine such that frameshift does not occur" means that the gene encoding an Alzheimer's disease vaccine has been inserted to a variable region(s) of a gene encoding a wild-type seed storage protein such that the amino acid sequence of the modified seed storage protein excluding the amino acid sequence of the Alzheimer's disease vaccine is identical to the amino acid sequence of the corresponding wild-type seed storage protein.

Further, "inserting a gene encoding an Alzheimer's disease vaccine" means that the gene encoding an Alzheimer's disease vaccine has been inserted without causing deletion of a nucleotide sequence encoding the variable region(s), as well as that all or a part of the nucleotide sequence encoding the variable region(s) was substituted with the gene encoding an Alzheimer's disease vaccine.

In the present invention, a variable region of a gene encoding a wild-type seed storage protein means a region which allows, even when an exogenous gene has been inserted thereto such that frameshift does not occur, the protein expressed from the resulting gene to maintain a stable spatial structure equivalent to that of the wild-type seed storage protein, thereby allowing maintenance of the properties of the wild-type seed storage protein.

For example, when the gene encoding a wild-type seed storage protein is the gene encoding the A1aB1b subunit of soybean 11S globulin containing the amino acid sequence of SEQ ID NO:2, five portions including the region encoding amino acid positions 20-28 (variable region I), the region encoding amino acid positions 111-128 (variable region II), the region encoding amino acid positions 198-216 (variable region III), the region encoding amino acid positions 268-315 (variable region IV) and the region encoding amino acid positions 490-495 (variable region V) in SEQ ID NO:2 are known as variable regions (FIG. 1).

Further, when the gene encoding a wild-type seed storage protein is a gene containing a nucleotide sequence encoding an amino acid sequence which has a certain identity to the amino acid sequence shown in SEQ ID NO:2, that is, the amino acid sequence shown in SEQ ID NO:2 except that one or more amino acids are substituted, inserted, added and/or deleted, the variable regions are the region encoding the amino acid sequence corresponding to amino acid positions 20-28, the region encoding the amino acid sequence corresponding to amino acid positions 111-128, the region encoding the amino acid sequence corresponding to amino acid positions 198-216, the region encoding the amino acid sequence corresponding to amino acid positions 268-315 and the region encoding the amino acid sequence corresponding to amino acid positions 490-495.

Here, when two amino acid sequences to be compared are aligned with each other to attain the maximum identity (%) between the amino acid sequences while introducing gaps as required, the "amino acid sequence corresponding to" a particular amino acid sequence means a partial amino acid sequence that corresponds to the other particular partial amino acid sequence. Such an amino acid sequence can be easily specified by those skilled in the art.

When plural variable regions exist in the gene encoding a wild-type seed storage protein, the gene encoding a modified seed storage protein can be prepared by inserting a gene encoding an Alzheimer's disease vaccine to one or more of the variable regions.

For example, when a gene encoding the A1aB1b subunit of soybean 11S globulin containing the amino acid sequence of SEQ ID NO:2 is used as the gene encoding a wild-type seed storage protein, any one of the variable regions II, III, IV and V may be selected as the variable region to which the gene encoding an Alzheimer's disease vaccine is to be inserted, and the gene encoding an Alzheimer's disease vaccine is more preferably inserted to the variable region III. Further, as the variable regions to which the gene encoding an Alzheimer's disease vaccine is to be inserted, two or more regions among the variable regions II, III, IV and V may be selected, and, for example, insertion into the three regions II, III and IV at the same time, insertion into the four regions II, III, IV and V at the same time, and the like can be carried out. Here, introduction of the gene encoding an Alzheimer's disease vaccine needs to be carried out such that frameshift does not occur in the nucleotide sequence encoding the wild-type seed storage protein.

Further, when a gene encoding common bean arcelin 5 containing the amino acid sequence shown in SEQ ID NO:37 is used as the gene encoding a wild-type seed storage protein, since the variable region(s) of the gene is/are not known, it is necessary to compare its DNA sequence with that of the A1aB1b subunit to confirm disordered regions, and to compare its amino acid sequence and spatial structure with those of other similar storage proteins to confirm the differences in the gaps of the sequence and the structural differences, thereby assuming the variable region(s). It is preferred to insert the gene encoding an Alzheimer's disease vaccine into the region encoding amino acid positions 149-150 (variable region A) and/or the region encoding amino acid positions 250-251 (variable region B) in SEQ ID NO:37, which regions can be specified by such assumption.

Further, when the gene encoding the wild-type seed storage protein contains a nucleotide sequence encoding an amino acid which has a certain identity to the amino acid sequence shown in SEQ ID NO:37, that is, the amino acid sequence shown in SEQ ID NO:37 except that one or more amino acids are substituted, inserted, added and/or deleted, the gene encoding an Alzheimer's disease vaccine is preferably inserted into the region encoding the amino acid sequence corresponding to amino acid positions 149-150, the region encoding the amino acid sequence corresponding to amino acid positions 250-251 in SEQ ID NO:37.

Further, when a gene encoding rice prolamin containing the amino acid sequence shown in SEQ ID NO:45 is used as the gene encoding a wild-type seed storage protein, since the spatial structure and the variable region(s) of the gene are not known, it is necessary to compare its amino acid sequence with those of other similar storage proteins to confirm the gap structure, thereby assuming the variable region(s). It is preferred to insert the gene encoding an Alzheimer's disease vaccine into the region encoding amino acid positions 110-111 (variable region a) in SEQ ID NO:45, which region can be specified by such assumption.

Further, when the gene encoding the wild-type seed storage protein contains a nucleotide sequence encoding an amino acid which has a certain identity to the amino acid sequence shown in SEQ ID NO:45, that is, the amino acid sequence shown in SEQ ID NO:45 except that one or more amino acids are substituted, inserted, added and/or deleted, the gene encoding an Alzheimer's disease vaccine is preferably inserted into the region encoding the amino acid sequence corresponding to amino acid positions 110-111 in SEQ ID NO:45.

3. Gene Encoding Alzheimer's Disease Vaccine

The gene encoding an Alzheimer's disease vaccine in the present invention is not restricted as long as it is a DNA encoding a protein or a peptide having a function as a vaccine against Alzheimer's disease, and is preferably a DNA encoding a β-amyloid antigenic determinant composed of a peptide of about 5 to 25 amino acids constituting a part of β-amyloid. Examples of the DNA include DNAs encoding the amino acid sequence of SEQ ID NO:3.

Since a nucleotide sequence encoding β-amyloid is known (GenBank accession No. AB113349), it is possible to isolate a DNA encoding β-amyloid or a β-amyloid antigenic determinant from a cDNA library, by a screening operation based on this nucleotide sequence information. A DNA encoding a β-amyloid antigenic determinant can be prepared also by chemical synthesis.

Further, in the present invention, the Alzheimer's disease vaccine can also be inserted to a variable region(s) of a gene encoding a seed storage protein in such a manner that plural genes encoding the vaccine are tandemly linked to each other, thereby allowing expression of the vaccine. For example, the gene encoding a β-amyloid antigenic determinant may be inserted, such that frameshift does not occur, to a variable region(s) in such a manner that an integer number of 1 to 20, preferably an integer number of 1 to 5, more preferably an integer number of 1 to 3, especially preferably 2 copies of the gene are linked to each other.

Further, when the gene encoding an Alzheimer's disease vaccine is inserted into the gene encoding a wild-type seed storage protein, a nucleotide sequence(s) which encode(s) a sequence recognized by a protease may also be added to the 5'-end and/or the 3'-end of the gene encoding an Alzheimer's disease vaccine. By this, the Alzheimer's disease vaccine can be cleaved out with the protease from the modified seed storage protein produced in seeds. Examples of such a protease include thermolysin.

4. Vector for Gene Transfer

The vector for gene transfer of the present invention may have a structure wherein a promoter that induces soybean seed-specific expression is linked to the upstream of the gene. Further, a terminator may also be linked to the downstream of the gene.

Examples of the promoter that induces soybean seed-specific expression include the soybean 11S globulin promoter and the common bean arcelin promoter, and examples of the terminator include the soybean 11S globulin terminator, the common bean arcelin 2 terminator, the 35S terminator and the NOS terminator of cauliflower mosaic virus.

Examples of the soybean 11S globulin promoter include the promoter of the soybean 11S globulin A1aB1b subunit having the sequence shown in SEQ ID NO:18, and the soybean 11S globulin promoter may be one having an identity of not less than 95% to this sequence as long as it has a seed-specific promoter activity. Examples of the soybean 11S globulin terminator include the terminator of the soybean 11S globulin A1aB1b subunit having the sequence shown in SEQ ID NO:21, and the soybean 11S globulin terminator may be one having an identity of not less than 95% to this sequence as long as it has a seed-specific terminator activity.

Examples of the common bean arcelin promoter include the promoter of common bean arcelin 2 having the sequence of nucleotide positions 1399-3860 in SEQ ID NO:56, and the common bean arcelin promoter may be one having an identity of not less than 95% to this sequence as long as it has a seed-specific promoter activity. Examples of the common bean arcelin terminator include the common bean arcelin 2 terminator having the sequence shown in SEQ ID NO:59, and the common bean arcelin terminator may be one having an identity of not less than 95% to this sequence as long as it has a seed-specific terminator activity.

To the vector of the present invention, a selection marker gene for selecting recombinants, and a reporter gene for confirming expression of the introduced gene may be inserted. Examples of the selection marker gene include the hygromycin resistance gene, the phosphinothricin resistance gene or the like, and examples of the reporter gene include the β-glucuronidase (GUS) gene, chloramphenicol acetyltransferase (CAT) gene, luciferase (LUC) gene and GFP gene or the like.

The vector of the present invention may be obtained also by inserting a DNA fragment, which contains a promoter for induction of seed-specific expression, a gene encoding a modified storage protein linked to the downstream of the promoter, and a terminator linked to the further downstream, to a vector comprising the above-described selection marker gene and/or reporter gene.

5. Soybean Plant which can be Transformed

Examples of the soybean which can be transformed in the present invention include varieties which are generally used for food, for feed or for producing oil. The soybean to be transformed is preferably partially or totally deficient for the endogenous seed storage proteins, and examples of the soybean include those which are partially or totally deficient for soybean 11S globulin and/or soybean 7S globulin. Here, "partially deficient" means cases where the expression level is lower than in the wild type, as well as cases where only a part of the subunits are completely deficient, and cases where the expression levels of only a part of the subunits are lower than those in the wild type. Particular examples of the soybean include the mutant line EnB1, which is deficient for soybean 11S globulin, the mutant line QY2, which is deficient for soybean 7S globulin, and the mutant line QF2, which is deficient for both 11S globulin and 7S globulin. Further examples of the soybean include progeny lines derived by hybridization between such defective lines and common varieties (e.g., Jack or the like).

Confirmation of the fact that the soybean is partially or totally deficient for endogenous soybean 11S globulin and/or soybean 7S globulin can be carried out by electrophoresis of the storage proteins prepared from seeds.

6. Preparation of Transformed Soybean Plant

Examples of the material which may be used for preparation of the transformed soybean plant include plant tissues such as roots, stems, leaves, seeds, embryos, ovules, ovaries, shoot apices, anther and pollens, and sections thereof; and plant cultured cells such as undifferentiated calluses, adventive embryos and protoplasts or the like.

The introduction of the gene encoding a modified seed storage protein to the above material may be carried out by various methods which have already been reported and established, and it is preferred to introduce the above-mentioned vector for gene transfer using the *Agrobacterium* method, PEG method, electroporation method, particle gun method, whisker ultrasonic method or the like.

Using the resistance effect given by the selection marker gene as an index, cells of the transformed soybean plant can be selected from the material to which the gene encoding a modified seed storage protein has been introduced. From the selected cells, a transformed soybean plant body can be obtained through the step of regenerating a plant body, which step has been reported for each plant species.

By cultivating the thus obtained transformed soybean plant body to allow seed ripening, seeds of the transformed soybean of the present invention can be obtained, and the Alzheimer's disease vaccine of interest can be obtained in the transformed seeds.

Whether or not the gene encoding the Alzheimer's disease vaccine has been introduced into the plant body can be confirmed by the PCR method, Southern hybridization method, Northern hybridization method, Western blotting method or the like. For example, by extracting protein from seeds of the transformed soybean plant body and carrying out Western blotting by immunostaining using a primary antibody specific to the Alzheimer's disease vaccine and a secondary antibody labeled with horseradish peroxidase (HRP) or the like, it is possible to confirm appropriate introduction of the gene encoding the Alzheimer's disease vaccine, accumulation of the Alzheimer's disease vaccine in the seeds, and the amount of the vaccine accumulated.

The performance of the Alzheimer's disease vaccine contained in the modified seed storage protein accumulated in the seeds of the transformed soybean plant can be evaluated by, for example, using a disease-model mouse that develops Alzheimer's disease. More particularly, the modified seed storage protein containing the Alzheimer's disease vaccine, or the Alzheimer's disease vaccine cleaved out from the modified seed storage protein with a protease followed by purification, is administered to the above model mouse by subcutaneous injection or oral administration. The performance of the Alzheimer's disease vaccine can be evaluated by investigating production of antibodies against the Alzheimer's disease vaccine, the amount of β-amyloid, brain tissue, and/or behavior disorder in the mouse. The modified seed storage protein containing the Alzheimer's disease vaccine, or the Alzheimer's disease vaccine cleaved out from the modified seed storage protein with a protease followed by purification, may be administered as a mixture with an adjuvant.

The Alzheimer's disease vaccine can be produced in a large amount by cultivating and then collecting seeds of the transformed soybean that accumulates a modified seed storage protein containing the vaccine, in the outdoor field, or closed facilities for cultivation where the environment is artificially controlled.

The seeds wherein the modified seed storage protein containing the Alzheimer's disease vaccine is accumulated can be used for prophylaxis and/or therapy of Alzheimer's disease, as a composition containing the Alzheimer's disease vaccine. For example, the seeds processed by pulverization or the like may be made into the form of a tablet, granule, powder, capsule, beverage or the like.

Further, the above composition may contain the modified seed storage protein accumulated in the seeds, which protein has been extracted and purified. For example, after a ground product of the seeds subjected to defatting and heat treatment, the modified seed storage protein containing the Alzheimer's disease vaccine of interest may be purified by an apparatus such as liquid chromatography. Further, the above-described composition may contain the Alzheimer's disease vaccine which has been prepared by treating the modified seed storage protein with a protease and purifying the resulting product, thereby partially or totally removing the part of the wild-type seed storage protein from the modified seed storage protein.

The present invention will now be described more concretely by way of Examples, but the present invention is not restricted to these Examples.

The procedures of the experimental methods carried out in the Examples below are those according to "Molecular Cloning" 2nd Ed. (J. Sambrook et al., Cold Spring Harbor Laboratory press, published in 1989) unless otherwise specified.

EXAMPLES

Example 1

Construction of Expression Plasmids for Modified Soybean 11S Globulin A1aB1b

Expression plasmids for expression of genes encoding modified A1aB1b containing the peptide having the amino acid sequence shown in SEQ ID NO:3 (hereinafter abbreviated as Aβ4-10), which is known as a β-amyloid antigenic determinant, in soybean seeds were constructed. The procedure for the construction is shown in FIG. 2.

An oligonucleotide having three copies of a nucleotide sequence encoding Aβ4-10 which are tandemly linked to each other (the sense strand, SEQ ID NO:4) and the oligonucleotide having its complementary sequence (the antisense strand, SEQ ID NO:5) were synthesized using the custom DNA synthesis service by FASMAC Co., Ltd. (the sense strand and the antisense strand are hereinafter referred to as 410F and 410R, respectively). Unless otherwise specified, the hereinafter-mentioned oligonucleotides were those synthesized using the custom DNA synthesis service by the above manufacturer. In the presence of ATP at a final concentration of 1 mM, 100 pmol each of 410F and 410R was subjected to phosphorylation reaction with T4 Polynucleotide Kinase (manufactured by TAKARA BIO INC.), and the reaction solutions after the reaction were mixed together, followed by heating the resulting mixture at 94° C. for 10 minutes and then allowing the mixture to cool gradually to 37° C. for 1 hour, thereby carrying out annealing. By this process, a double-stranded DNA fragment encoding a peptide wherein three copies of Aβ4-10 are tandemly linked to each other ((Aβ4-10)×3) was obtained.

Using, as a template, the plasmid pBSK-A1aB1b (obtained from Kyoto University) wherein cDNA of the known A1aB1b gene (GenBank accession No. AB113349) is cloned at the SmaI site of pBluescript II SK(–) (manufactured by Stratagene), PCR was carried out to amplify a fragment containing the vector portion such that the 5'-end and the 3'-end of the fragment are positioned at a specific variable region of the gene encoding A1aB1b. The obtained DNA fragment was ligated with the double-stranded DNA fragment encoding (Aβ4-10)×3, to prepare the gene encoding a modified A1aB1b. The method is more concretely described below.

A total of five primer sets, that is, the primer set (PS-1) composed of the primer pair of SEQ ID NOs:6 and 7 for insertion into the variable region II, the primer set (PS-2) composed of the primer pair of SEQ ID NOs:8 and 9 for insertion into the variable region III, the primer set (PS-3) composed of the primer pair of SEQ ID NOs:10 and 11 and the primer set (PS-4) composed of the primer pair of SEQ ID NOs:12 and 13 for insertion into the variable region IV, and the primer set (PS-5) composed of the primer pair of SEQ ID NOs:14 and 15 for insertion into the variable region V, of the gene encoding A1aB1b having the sequence shown in SEQ ID NO:1 were prepared. The primers were synthesized such that nucleotide substitutions for introducing amino acid substitutions in the immediate downstream of the insertion regions were introduced in order to allow cleaving out of (Aβ4-10)×3 from the modified A1aB1b proteins using a protease thermolysin.

The regions in the nucleotide sequence shown in SEQ ID NO:1, into which the DNA encoding (Aβ4-10)×3 was inserted using the respective primer sets are hereinafter referred to as the PS-1 region, PS-2 region, PS-3 region, PS-4 region and PS-5 region, respectively.

PCR was performed using 10 ng of pBSK-A1aB1b as a template and 50 μL/reaction of a reaction solution, by carrying out 1 cycle of 2 minutes of denaturation at 94° C. and then 25 cycles of 30 seconds of denaturation at 94° C., 30 seconds of annealing at 57° C. and 5 minutes of extension at 68° C. The reaction solution contained 200 μM dNTP mixture, 1.5 mM $MgSO_4$ solution, each of the above primers at a concentration of 1 μM, and KOD-Plus-Ver.2 buffer containing 1 unit of KOD-Plus-(manufactured by Toyobo Co. Ltd.). The hereinafter-mentioned PCRs were carried out using the same composition except for the primers, unless otherwise specified.

Using DNA Ligation Kit (manufactured by TAKARA BIO), 50 fmol of each of the thus obtained DNA fragments and 150 fmol of the double-stranded DNA fragment encoding the above-described (Aβ4-10)×3 were subjected to ligation reaction at 16° C. for 40 minutes. The reaction product was used for transformation of *E. coli* DH5α competent cells (manufactured by TAKARA BIO) to obtain plural transformed *E. coli* cells. From the obtained *E. coli* cells, plasmid DNAs were extracted and purified, followed by analyzing their nucleotide sequences using the DNA sequencing service by FASMAC Co., Ltd. In the case where PS-1 was used, the result of the nucleotide sequence analysis of 12 clones of the transformed *E. coli* showed that one clone had one molecule of the double-stranded DNA fragment encoding (Aβ4-10)×3 in a state where the fragment was correctly inserted in the forward direction. Further, 24 clones, 54 clones, 30 clones and 12 clones were analyzed in the cases where PS-2, PS-3, PS-4 and PS-5 were used, respectively, and one each clone having one molecule of the double-stranded DNA fragment encoding (Aβ4-10)×3 in a state where the fragment was correctly inserted in the forward direction was obtained. The probability with which a modified A1aB1b gene wherein the fragment was correctly inserted can be obtained varied among the insertion sites, and insertion of the fragment was especially difficult in the case where PS-3 was used.

All of the thus prepared genes encoding modified A1aB1b were subjected to confirmation of their nucleotide sequences. Unless otherwise specified, the hereinafter-mentioned determination of nucleotide sequences was carried out using the DNA sequencing service by FASMAC Co., Ltd.

Subsequently, in order to prepare the modified A1aB1b genes wherein DNAs encoding (Aβ4-10)×3 are inserted in plural variable regions, PCR was carried out using the above-prepared genes encoding modified A1aB1b as templates and the primer sets that were the same as described above. Ligation reaction of the obtained DNA fragment and the double-stranded DNA fragment encoding the above-described (Aβ4-10)×3 peptide was repeated, to prepare the genes encoding modified A1aB1b. By this process, plasmids containing the genes encoding modified A1aB1b, in which DNAs encoding (Aβ4-10)×3 are inserted in plural variable regions of the A1aB1b gene, were prepared. The particular insertion regions, and the names of the genes encoding modified A1aB1b corresponding thereto are shown in Table 1.

TABLE 1

| Name | Region of insertion of DNA encoding (Aβ4-10) × 3, and number of inserted DNA |
|---|---|
| A1aB1bM1 | one each in PS-1 region, PS-2 region and PS-4 region |
| A1aB1bM2 | one in PS-1 region |
| A1aB1bM3 | one in PS-2 region |
| A1aB1bM4-1 | one in PS-3 region |
| A1aB1bM4-2 | one in PS-4 region |
| A1aB1bM5 | one each in PS-1 region, PS-2 region, PS-3 region, PS-4 region and PS-5 region |

To allow soybean seed-specific expression of the genes encoding modified A1aB1b prepared as described above, the promoter region and the terminator region of the wild-type A1aB1b gene were isolated.

Using, as a probe, the promoter region of the known partial genome sequence of the A1aB1b gene (GenBank accession No. X15121) containing a partial promoter sequence of the A1aB1b gene of 639 bp, a Misuzudaizu TAC library (www.kazusa.or.jp/ja/plant/PG2HP Transformation competent bacterial artificial chromosome) kept in National Agricultural Research Center for Hokkaido Region, National Agriculture and Food Research Organization was screened. As a result of analysis of the nucleotide sequence of the obtained clone, it was revealed that the promoter region located 2202 bp upstream of the translation initiation site of the A1aB1b gene was contained in the clone. Based on the obtained nucleotide sequence, a primer set composed of the oligonucleotide pair of SEQ ID NOs:16 and 17 was prepared, which primer set was then used for carrying out PCR in order to isolate the promoter region.

The above PCR was performed using the genomic DNA of Misuzudaizu as a template and 50 μL/reaction of a reaction solution, by carrying out 1 cycle of 2 minutes of denaturation at 94° C. and then 25 cycles of 30 seconds of denaturation at 94° C., 30 seconds of annealing at 57° C. and 2 minutes 30 seconds of extension at 68° C. By this process, a promoter fragment of the A1aB1b gene having a length of 2202 bp (Gy1P) (SEQ ID NO:18) was obtained.

Subsequently, in order to isolate the terminator region of the A1aB1b gene, a primer set composed of SEQ ID NOs:19 and 20 was prepared based on the known partial genomic sequence of the wild-type A1aB1b gene (GenBank accession No.X53404), which primer set was then used for carrying out PCR.

The above PCR was performed using the genomic DNA of Misuzudaizu as a template and 50 μL/reaction of a reaction solution, by carrying out 1 cycle of 2 minutes of denaturation at 94° C. and then 25 cycles of 30 seconds of denaturation at 94° C., 30 seconds of annealing at 57° C. and 1 minute of extension at 68° C. By this process, a terminator fragment of the wild-type A1aB1b gene having a length of 1052 bp (Gy1T) (SEQ ID NO:21) was obtained.

To allow seed-specific expression of the genes encoding modified A1aB1b, each of the genes encoding modified A1aB1b, and Gy1P and Gy1T, which were obtained as described above, were ligated with the known pUHG vector (Y. Kita, K. Nishizawa, M Takahashi, M. Kitayama, M. Ishimoto. (2007) Genetic improvement of somatic embryogenesis and regeneration in soybean and transformation of the improved breeding lines. Plant Cell Reports 26:439-447) (FIG. 3) to construct an expression plasmid.

In order to obtain DNA fragments encoding 5 types of modified A1aB1b among those described above, PCR was carried out using the above-described A1aB1bM2 (SEQ ID NO:22), A1aB1bM3 (SEQ ID NO:24), A1aB1bM4-1 (SEQ ID NO:26), A1aB1bM1 (SEQ ID NO:28) and A1aB1bM5 (SEQ ID NO:30) as templates, and the primer set composed of the oligonucleotide pair of SEQ ID NOs:32 and 33.

The above PCR was performed using 50 μL/reaction of a reaction solution, by carrying out 1 cycle of 2 minutes of denaturation at 94° C. and then 25 cycles of 30 seconds of denaturation at 94° C., 30 seconds of annealing at 57° C. and 2 minutes of extension at 68° C. By this process, a DNA fragment of each modified A1aB1b gene was obtained.

The DNA fragment of the modified A1aB1b gene, the promoter DNA fragment and the terminator DNA fragment were subjected to phosphorylation reaction, and then ligated into pUHG vector which had been preliminarily digested with SmaI and dephosphorylated with CIAP (manufactured by TAKARA BIO INC.). By analyzing the nucleotide sequences of the obtained clones, clones in which the Gy1P promoter, the gene encoding modified A1aB1b and the Gy1T terminator are correctly linked in this order were selected.

By this process, the following five types of plant transformation vectors (pUHG A1aB1bM1, pUHGA1aB1bM2, pUHGA1aB1bM3, pUHGA1aB1bM4-1 and pUHGA1aB1bM5) that express the genes encoding modified A1aB1b in a seed-specific manner were constructed.

Example 2

Construction of Expression Plasmid for Modified Common Bean Arcelin

Expression plasmids for expression, in soybean seeds, of genes encoding modified arcelin in which two copies of Aβ4-10 tandemly linked to each other (hereinafter abbreviated as (Aβ4-10)×2) are inserted were constructed.

Since the variable region(s) of the gene encoding the known common bean arcelin 5-1 (GenBank accession No. Z50202) (SEQ ID NO:36) has/have not been revealed, assumption of the variable region(s) was carried out. Based on assumption of the variable region(s) by comparison of the DNA sequence with that of A1aB1b, it was revealed that the disorder region is restricted to the C terminus. Therefore, it was thought that the peptide sequence may be inserted into the C terminus. In order to further specify the variable region, the DNA sequence of the gene was compared with that of phytohemagglutinin, which belongs to 2S albumin as arcelin does, and it was revealed that the loop structure of 8 to 10 residues found in phytohemagglutinin is absent in the downstream of the lysine (amino acid position 149 in SEQ ID NO:37), which is the corresponding portion in Arc5-1. Therefore, the nucleotide sequence region in SEQ ID NO:36 that encodes this portion (amino acid positions 149-150) was assumed to be the variable region A. Subsequently, arcelin 1 was compared with one of the storage proteins of common bean, phaseolin. As a result, a gap of 7 residues was found in the downstream of asparagine corresponding to amino acid position 250 of SEQ ID NO:37. Therefore, the nucleotide sequence region encoding this portion (amino acid positions 250-251) was assumed to be the variable region B.

In order to incorporate the DNA encoding (Aβ4-10)×2 into the assumed variable regions of the gene encoding Arc5-1, the oligonucleotide encoding (Aβ4-10)×2 (420F, SEQ ID NO:34) and the oligonucleotide complementary thereto (420R, SEQ ID NO:35) were synthesized.

In the presence of ATP at a final concentration of 1 mM, 100 pmol each of 420F and 420R was subjected to phosphorylation reaction with T4 Polynucleotide Kinase (manufactured by TAKARA BIO INC.), and the reaction solutions after the reaction were mixed together, followed by heating the resulting mixture at 94° C. for 10 minutes and then allowing the mixture to cool gradually to 37° C. for 1 hour, thereby carrying out annealing. By this process, a double-stranded DNA fragment encoding (Aβ4-10)×2 was obtained.

Using, as a template, the plasmid pBSK-Arc5-1 (kept in National Agricultural Research Center for Hokkaido Region, National Agriculture and Food Research Organization) obtained by inserting cDNA encoding Arc5-1 into the SmaI site of pBluescript II SK(−) (manufactured by Stratagene), PCR was carried out to obtain a DNA fragment containing the vector portion, such that the amino acid portion of a particular variable region of the gene encoding Arc5-1 is positioned at the ends. This DNA fragment was ligated with the double-stranded DNA fragment encoding (Aβ4-10)×2 synthesized as described above, to prepare a plasmid containing the gene encoding modified Arc5-1.

The method is more concretely described below.

A total of two primer sets, that is, the primer set (PS-A) composed of the primer pair of SEQ ID NOs:38 and 39 for insertion into the variable region A, and the primer set (PS-B) composed of the primer pair of SEQ ID NOs:40 and 41 for insertion into the variable region B, in the gene encoding Arc5-1 were prepared. The primers were synthesized such that nucleotide substitutions for introducing amino acid substitutions in the immediate upstream and downstream of the insertion regions were introduced in order to allow cleaving out of Aβ4-10 from the modified Arc5-1 proteins using a protease thermolysin.

The regions in the nucleotide sequence of SEQ ID NO:36, into which the DNA encoding (Aβ4-10)×2 was inserted using the respective primer sets are hereinafter referred to as the PS-A region and PS-B region, respectively.

PCR was carried out using 10 ng of pBSK-Arc5-1 as a template. This PCR was performed using 50 μL/reaction of a reaction solution, by carrying out 1 cycle of 2 minutes of denaturation at 94° C. and then 25 cycles of 30 seconds of denaturation at 94° C., 30 seconds of annealing at 57° C. and 4 minutes of extension at 68° C. The thus obtained DNA fragment and the double-stranded DNA fragment encoding the above-described (Aβ4-10)×2 were subjected to ligation reaction.

By this process, 2 types of plasmids containing a gene encoding modified Arc5-1, wherein the DNA encoding (Aβ4-10)×2 is inserted in a variable region of the gene encoding Arc5-1, were prepared. The particular insertion regions of the DNAs encoding (Aβ4-10)×2, and the names of the genes encoding modified Arc5-1 corresponding thereto are shown in Table 2.

TABLE 2

| Name | Region of insertion of DNA encoding (Aβ4-10) × 2, and number of inserted DNA |
|---|---|
| Arc5M1 | one in PS-A region |
| Arc5M2 | one in PS-B region |

In order to allow soybean seed-specific expression of modified Arc5-1, each of the above obtained Arc5M1 and Arc5M2, and Gy1P and Gy1T derived from the A1aB1b gene in the above Example 1, were ligated with the pUHG vector to construct an expression plasmid. In order to obtain DNA fragments encoding modified Arc5-1, PCR was carried out using the above-described Arc5M1 and Arc5M2 as templates, and the primer set composed of the oligonucleotide pair of SEQ ID NOs:42 and 43.

The above PCR was performed using 50 μL/reaction of a reaction solution, by carrying out 1 cycle of 2 minutes of denaturation at 94° C. and then 25 cycles of 30 seconds of denaturation at 94° C., 30 seconds of annealing at 57° C. and 1 minute of extension at 68° C. By this process, a DNA fragment of each modified Arc5-1 gene was obtained.

The DNA fragment of the modified Arc5-1 gene, Gy1P and Gy1T were subjected to phosphorylation reaction, and then ligated into the pUHG vector which had been preliminarily digested with SmaI and dephosphorylated.

By this process, plant transformation vectors pUHG Arc5M1 and pUHG Arc5M2 that express the modified Arc5-1 genes in a seed-specific manner were constructed.

Example 3

Construction of Expression Plasmid for Modified Rice Prolamin

An expression plasmid for expression, in soybean seeds, of a gene encoding modified prolamin in which DNA encoding (Aβ4-10)×2 is inserted was constructed.

Since the variable region(s) of the gene encoding the known rice prolamin 10K, RP10 (GenBank accession No. E09782) (SEQ ID NO:44), has/have not been revealed, assumption of the variable region(s) was carried out. The amino acid sequence of RP10 was compared with that of zein delta, which is one of the major storage proteins in maize. As a result, a gap of 11 residues was found in the downstream of lysine corresponding to amino acid position 110 of SEQ ID NO:45. Therefore, the nucleotide sequence region encoding this portion (amino acid positions 110-111) was assumed to be the variable region a.

Subsequently, using, as a template, the plasmid pBSK-RP10 (kept in National Agricultural Research Center for Hokkaido Region, National Agriculture and Food Research Organization) obtained by cloning the cDNA encoding the rice prolamin 10K, RP10, into the SmaI site of pBluescript II SK(−) (manufactured by Stratagene), PCR was carried out to obtain a DNA fragment containing the vector portion, such that the amino acid portion of the particular variable region a of the gene encoding RP10 is positioned at the ends. This DNA fragment was ligated with the double-stranded DNA fragment encoding (Aβ4-10)×2 synthesized in Example 2, to prepare a plasmid containing a gene encoding modified RP10.

The method is more concretely described below.

A primer set composed of the primer pair of SEQ ID NOs:46 and 47 for insertion into the variable region a in the gene encoding RP10 was prepared. The primers were synthesized such that nucleotide substitutions for introducing amino acid substitutions in the immediate upstream and downstream of the insertion region were introduced in order to allow cleaving out of the Aβ4-10 peptide from the modified RP10 protein using a protease thermolysin.

PCR was carried out using 10 ng of pBSK-RP10 as a template. This PCR was performed using 50 μL/reaction of a reaction solution, by carrying out 1 cycle of 2 minutes of denaturation at 94° C. and then 25 cycles of 30 seconds of denaturation at 94° C., 30 seconds of annealing at 57° C. and 4 minutes of extension at 68° C. The obtained DNA fragments and the double-stranded DNA fragment encoding the above-described (A(β4−10)×2 were subjected to ligation reaction.

By this process, a plasmid (RP10M1) containing a gene encoding modified RP10, wherein the DNA encoding (Aβ4-10)×2 is inserted in the variable region of the gene encoding RP10, was prepared.

In order to allow seed-specific expression of the gene encoding modified RP10, the gene encoding modified RP10, and Gy1P and Gy1T obtained in the above Example 1 were ligated with the pUHG vector to construct an expression plasmid. In order to obtain a DNA fragment encoding modified RP10, PCR was carried out using the above-described RP10M1 as a template, and the primer set composed of SEQ ID NOs:48 and 49.

The above PCR was performed using 50 μL /reaction of a reaction solution, by carrying out 1 cycle of 2 minutes of denaturation at 94° C. and then 25 cycles of 30 seconds of denaturation at 94° C., 30 seconds of annealing at 57° C. and 1 minute of extension at 68° C. By this process, a DNA fragment encoding modified RP10 was obtained.

The DNA fragment encoding modified RP10, and the promoter DNA fragment and the terminator DNA fragment were subjected to phosphorylation reaction, and then ligated into the pUHG vector which had been preliminarily digested with SmaI and dephosphorylated.

By this process, a plant transformation vector pUHG RP10M1 that expresses the gene encoding modified RP10 in a seed-specific manner was constructed.

Example 4

Construction of Expression Plasmids for Respective Modified Types Using Arcelin 2 Promoter Expression plasmids for expressing, in soybean seeds, the genes encoding modified A1aB1b prepared in Example 1 with a common bean-derived arcelin 2 promoter were constructed.

(1) Isolation of Common Bean-Derived Arcelin 2 Promoter

From 1 g of fresh leaves of the wild species of common bean (line number: G12866), 50 μg of genomic DNA was extracted using DNeasy Plant Maxi kit (manufactured by QIAGEN).

After digesting 280 ng of the genomic DNA with the restriction enzyme SauIIIAI, dGTP was added to the resulting digestion product, followed by carrying out single-nucleotide extension reaction (the first extension reaction) using klenow enzyme (manufactured by Promega KK). Thereafter, the reaction product was ligated with the RWA-1 adapter included in RightWalk Kit™ using Ligation high (manufactured by Toyobo Co., Ltd.), and the resulting ligation product was used as a template for PCR to isolate the DNA in the upstream region of the arcelin 2 gene.

Subsequently, based on the nucleotide sequence of cDNA of the known common bean arcelin 2 gene (GenBank accession No. M28470), oligonucleotides having the nucleotide sequences shown in SEQ ID NOs: 50 and 51 (which were designated the primer SP1 and the primer SP2, respectively) were prepared using the custom synthesis service by FAS-MAC Co., Ltd.

```
                                       SEQ ID NO: 50
     (primer SP1) TTGGTTTTGT TGAACGTCTC GAC SEQ ID NO: 51
     (primer SP2) GGTGAGAAGC ACAAGGAAGA GG
```

Thereafter, PCR was carried out using, as a template, 2.8 ng of the above-constructed genomic DNA to which the adapter was ligated, the primer WP-1 included in RightWalk Kit™ and the primer SP1. The above PCR was performed using 50 μL/reaction of a reaction solution, by carrying out 1 cycle of 2 minutes of denaturation at 94° C. and then 35 cycles of 30 seconds of denaturation at 94° C., 30 seconds of annealing at 65° C. and 5 minutes of extension at 68° C. The reaction solution contained 200 μM dNTP mixture, 1.5 mM MgSO$_4$ solution, each of the above primers at a concentration of 1 μM, and KOD-Plus-Ver.2 buffer containing 1 unit of KOD-Plus-(manufactured by Toyobo Co. Ltd.).

Thereafter, the reaction solution was 100-fold diluted, and the second PCR was carried out using 1 μL of the resulting dilution as a template, the primer WP-2 included in Right-Walk Kit™ and the primer SP2. The composition of the solution and the temperature conditions in the second PCR were the same as those in the first PCR except for the template and the primers.

The amplified DNA fragment was subjected to phosphorylation reaction with T4 Polynucleotide Kinase (manufactured by TAKARA BIO INC.) in the presence of ATP at a final concentration of 1 mM, and then ligated with pBluescriptII SK(−) (manufactured by Stratagene) that had been preliminarily treated with SmaI.

This reaction product was designated Arc2P(i), and its nucleotide sequence was determined using the DNA sequencing service by FASMAC Co., Ltd. As a result, it was confirmed that the product contains a novel region having a length of 844 bp in the upstream of the initiation codon of the arcelin 2 gene.

Thereafter, in order to isolate the region located further upstream, new primers were prepared to carry out the second elongation reaction.

After digesting 280 ng of the genomic DNA with the restriction enzyme BglII, dGTP was added to the resulting digestion product, followed by carrying out single-nucleotide extension reaction using klenow enzyme (manufactured by Promega KK). Thereafter, the reaction product was ligated with the RWA-1 adapter included in RightWalk Kit™, and the resulting ligation product was used as a template for PCR to isolate the promoter.

Subsequently, based on the nucleotide sequence of cDNA of the known common bean arcelin 2 gene (GenBank accession No. M28470), an oligonucleotide having the nucleotide sequence shown in SEQ ID NO:52 (which was designated the primer secondSP1) was prepared, and, based on the nucleotide sequence located in a region of 844 bp upstream of the initiation codon, which was obtained in the first extension reaction, an oligonucleotide having the nucleotide sequence shown in SEQ ID NO:53 (which was designated the primer secondSP2) was prepared.

```
                                             SEQ ID NO: 52
(primer secondSP1) CAGATTTTTT GCCCTCAAAA TTGATG SEQ ID NO: 53
(primer secondSP2) CGGATGTGCG TGGACTACAA GG
```

Thereafter, PCR was carried out using, as a template, 2.8 ng of the above-constructed genomic DNA to which the adapter was ligated, the primer WP-1 included in RightWalk Kit™ and the primer secondSP1. The composition of the solution and the temperature conditions in the PCR were the same as those in the above-described first extension reaction except for the template and the primers.

Thereafter, the above PCR solution was 100-fold diluted, and the second PCR was carried out using 1 µL of the resulting dilution as a template, the primer WP-2 included in RightWalk Kit™ and the primer secondSP2. The composition of the solution and the temperature conditions in the second PCR were the same as those in the first PCR except for the template and the primers.

The amplified DNA fragment was subjected to phosphorylation reaction with T4 Polynucleotide Kinase (manufactured by TAKARA BIO INC.) in the presence of ATP at a final concentration of 1 mM, and then ligated with pBluescriptII SK(−) (manufactured by Stratagene) that had been preliminarily treated with SmaI.

This reaction product was designated Arc2P(ii), and its nucleotide sequence was determined. Thereafter, in order to isolate the region located further upstream, new primers were prepared to carry out the third elongation reaction.

After digesting 280 ng of the genomic DNA with the restriction enzyme XbaI, dCTP was added to the resulting digestion product, followed by carrying out single-nucleotide extension reaction using klenow enzyme (manufactured by Promega KK). Thereafter, the reaction product was ligated with the RWA-2 adapter included in RightWalk Kit™, and the resulting ligation product was used as a template for PCR to isolate the promoter.

Subsequently, based on the nucleotide sequence of 197 bp obtained in the second extension reaction, oligonucleotides having the nucleotide sequences shown in SEQ ID NOs: 54 and 55 (which were designated the primer thirdSP1 and the primer thirdSP2, respectively) were prepared.

```
                                             SEQ ID NO: 54
(primer thirdSP1) CGACCTGAAG AACGCAGCGG CGACC SEQ ID NO: 55
(primer thirdSP2) TACCAGCAGT TGATGGACAA GATC
```

Thereafter, PCR was carried out using, as a template, 2.8 ng of the above-constructed genomic DNA to which the adapter was ligated, the primer WP-1 included in RightWalk Kit™ and the primer thirdSP1. The composition of the solution and the temperature conditions in the PCR were the same as those in the above-described first extension reaction except for the template and the primers.

Thereafter, the above PCR solution was 100-fold diluted, and the second PCR was carried out using 1 µL of the resulting dilution as a template, the primer WP-2 included in RightWalk Kit™ and the primer thirdSP2. The composition of the solution and the temperature conditions in the second PCR were the same as those in the first PCR except for the template and the primers.

The amplified DNA fragment was subjected to phosphorylation reaction with T4 Polynucleotide Kinase (manufactured by TAKARA BIO INC.) in the presence of ATP at a final concentration of 1 mM, and then ligated with pBluescriptII SK(−) (manufactured by Stratagene) that had been preliminarily treated with SmaI.

This reaction product was designated Arc2P(iii), and its nucleotide sequence was determined. As a result it was confirmed that the product contains a novel region having a length of 2819 bp in the upstream of Arc2P(ii) (3860 bp in total). Thus, by the three times of extension reaction, DNA (Arc2P) having a length of 3860 bp which contains the 5'-untranslated region in the upstream of the initiation codon of the arcelin 2 gene, wherein the novel promoter sequence is included, was obtained (SEQ ID NO:56, in which the promoter region corresponds to nucleotide positions 1399-3860).

(2) Isolation of Common Bean-Derived Arcelin 2 Terminator

After digesting 280 ng of the genomic DNA extracted in the above (1) with the restriction enzyme NheI, dCTP was added to the resulting digestion product, followed by carrying out single-nucleotide extension reaction using klenow enzyme (manufactured by Promega KK). Thereafter, the reaction product was ligated with the RWA-2 adapter included in RightWalk Kit™ using Ligation high (manufactured by Toyobo Co., Ltd.), and the resulting ligation product was used as a template for PCR to isolate the terminator gene.

Subsequently, based on the nucleotide sequence of cDNA of the known common bean arcelin 2 gene (GenBank accession No. M28470), oligonucleotides having the nucleotide sequences shown in SEQ ID NOs:57 and 58 (which were designated the primer SP3 and the primer SP4, respectively) were prepared.

```
                                             SEQ ID NO: 57
(primer SP3) CATCAATTTT GAGGGCAAAA AATCTG SEQ ID NO: 58
(primer SP4) CGTTCCAACA TCCTCCTCAA CAAGATC
```

Thereafter, PCR was carried out using, as a template, 2.8 ng of the above-constructed genomic DNA to which the adapter was ligated, the primer WP-1 included in RightWalk Kit™ and the primer SP3. The above PCR was performed using 50 gL/reaction of a reaction solution, by carrying out 1 cycle of 2 minutes of denaturation at 94° C. and then 35 cycles of 30 seconds of denaturation at 94° C., 30 seconds of annealing at 65° C. and 5 minutes of extension at 68° C. The reaction solution contained 200 µM dNTP mixture, 1.5 mM MgSO₄ solution, each of the above primers at a concentration of 1 µM, and KOD-Plus-Ver.2 buffer containing 1 unit of KOD-Plus- (manufactured by Toyobo Co. Ltd.).

Thereafter, the reaction solution was 100-fold diluted, and the second PCR was carried out using 1 µL of the resulting dilution as a template, the primer WP-2 included in RightWalk Kit™ and the primer SP4. The composition of the solution and the temperature conditions in the second PCR were the same as those in the first PCR except for the template and the primers.

The amplified DNA fragment was subjected to phosphorylation reaction with T4 Polynucleotide Kinase (manufactured by TAKARA BIO INC.) in the presence of ATP at a final concentration of 1 mM, and then ligated with pBluescriptII SK(−) (manufactured by Stratagene) that had been preliminarily treated with SmaI.

This reaction product was designated Arc2T, and its nucleotide sequence was determined. As a result, it was confirmed that the product contains a novel region having a length of 795 bp in the downstream of the stop codon of the arcelin 2 gene wherein the 3′-untranslated region is included (SEQ ID NO:59).

(3) Construction of Various Modified Expression Plasmids

Figure 3:
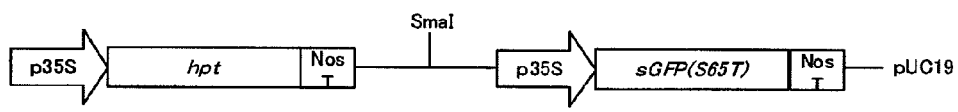

In order to express the genes encoding modified A1aB1b in seeds, the genes encoding various modified A1aB1b obtained in Example 1, and Arc2P and Arc2T were ligated with the known pUHG vector (mentioned above, FIG. 3), to construct expression plasmids.

The DNA fragment of each modified A1aB1b gene, the promoter DNA fragment and the terminator DNA fragment were subjected to phosphorylation reaction, and then ligated with the pUHG vector that had been preliminarily digested with SmaI and dephosphorylated with CIAP (manufactured by TAKARA BIO INC.). By analyzing the nucleotide sequences of the obtained clones, clones in which the Arc2P promoter, the gene encoding modified A1aB1b and the Arc2T promoter are correctly linked in this order were selected.

By this process, the following three types of plant transformation vectors (pUHGA2PA1aB1bM1, pUHGA2PA1aB1bM3 and pUHGA2PA1aB1bM5) that express the genes encoding modified A1aB1b under the control of the arcelin 2 promoter in a seed-specific manner were constructed.

In the same manner, a plant transformation vector pUHGA2PRP10M1 that expresses the gene encoding the above-mentioned RP10M1 in a seed-specific manner was constructed.

Example 5

Introduction of Gene Encoding Modified Seed Storage Protein to Soybean

By the known method (K. Nishizawa, Y. Kita, M. Kitayama, M. Ishimoto. (2006) A red fluorescent protein, DsRed2, as a visual reporter for transient expression and stable transformation in soybean. Plant Cell Reports 25:1355-1361), 30 adventitious embryonic masses (with diameters of not more than 3 mm) were induced from immature seeds of the soybean variety Jack and a mutant line deficient for 11S globulin and 7S globulin that are major seed storage proteins (kept in National Agricultural Research Center for Hokkaido Region, National Agriculture and Food Research Organization) (Y. Kita, K. Nishizawa, M Takahashi, M. Kitayama, M. Ishimoto. (2007) Genetic improvement of somatic embryogenesis and regeneration in soybean and transformation of the improved breeding lines. Plant Cell Reports 26:439-447), and these adventitious embryonic masses were placed in 1.5 ml tubes, followed by carrying out the gene transfer operation by the whisker ultrasonic method (JP 3312867 B).

In a 1.5 ml tube, 5 mg of whiskers made of potassium titanate LS20 (manufactured by Titan Kogyo, Ltd.) were placed, and the tube was left to stand for 1 hour, followed by removing and completely distilling ethanol to obtain sterile whiskers. Into the tube containing the whiskers, 1 ml of sterile water was added, and the resulting mixture was stirred well. The mixture of whiskers and sterile water was subjected to centrifugation, and water as the supernatant was discarded. In such a manner, the whiskers were washed. This washing operation for the whiskers was repeated 3 times. Thereafter, 0.5 ml of the known MS liquid medium was added to the tube to obtain a whisker suspension.

To the tube containing the whisker suspension obtained as described above, the above-described 30 adventitious embryonic masses (with diameters of not more than 3 mm) were added, and the resulting mixture was stirred, followed by centrifuging the mixture at 1000 rpm for 10 seconds to precipitate the adventitious embryonic masses and the whiskers. The supernatant was discarded to obtain a mixture of the adventitious embryonic masses and the whiskers.

Into the tube containing the above mixture, 20 μl (20 μg) each of the expression vectors for the modified seed storage proteins prepared in Examples 1 to 4 was added, and the resulting mixture was sufficiently mixed by shaking to obtain a uniform mixture.

Subsequently, this tube containing the uniform mixture was subjected to centrifugation at 18000×g for 5 minutes. The mixture after the centrifugation was mixed by shaking again. This operation was repeated 3 times.

The thus obtained tube containing the adventitious embryonic masses, the whiskers and the vector was placed in the bath of an ultrasonic generator such that the tube was sufficiently soaked therein. An ultrasonic wave with a frequency of 40 kHz was radiated to the tube at an intensity of 0.25 W/cm$^2$ for 1 minute. Thereafter, this mixture was left to stand for 10 minutes at 4° C. The mixture processed with ultrasonication in such a manner was washed with the above-described MS liquid medium.

The processed adventitious embryonic masses were cultured in the known liquid medium for growing adventitious embryos for 1 week by rotary shaking culture (100 rpm), and then cultured in a fresh liquid medium for growing adventitious embryos containing hygromycin B (15 mg/l) (Roche Diagnostics, Mannheim, Germany) for 1 week. Further, the adventitious embryonic masses were cultured in a liquid medium for growing adventitious embryos containing 30 mg/l hygromycin B for 4 weeks (while exchanging the medium every week), and then subjected to selection culture in a liquid medium for growing adventitious embryos containing 45 mg/l hygromycin B for 1 week. The gene transfer was carried out for 12 microtubes per vector.

Hygromycin-resistant adventitious embryonic masses were transferred to a liquid medium for maturation of adventitious embryos, and the culture was continued with shaking (100 rpm) for 4 weeks to allow maturation of the adventitious embryos. The mature adventitious embryos were dried by being left to stand in a sterile Petri dish for 3 to 5 days, and then transferred to the known solid medium for germination. After carrying out germination culture for 7 to 10 days, the embryos were transferred to the known rooting medium, thereby allowing the germinated seedlings to grow. After the growth of roots and buds, the plants were transferred to a pot containing soil, and high humidity was maintained until acclimation.

Example 6

Preparation of Transformed Soybean Plant to which Modified Seed Storage Protein Gene was Introduced By such a process, 6 individuals of transformed soybean plants produced by introducing A1aB1bM1, 6 individuals of transformants produced by introducing A1aB1bM2, 5 individuals of transformants produced by introducing A1aB1bM3, 5 individuals of transformants produced by introducing A1aB1bM4-1, and 9 individuals of transformants produced by introducing A1aB1bM5, to the Jack variety were prepared. Further, 3 individuals of transformed soybean plants to which Arc5M1 was introduced, 3 individuals of transformants to which Arc5M2 was introduced, and 2 individuals of transformed soybean plants to which RP10M1 was introduced were prepared.

Further, 12 individuals of transformed soybean plants produced by introducing A1aB1bM1, and 6 individuals of transformed soybean plants produced by introducing RP10M1, to the above-described mutant line deficient for 11S globulin and 7S globulin (hereinafter referred to as the seed storage protein-deficient variety) were prepared.

Further, 5 individuals of transformed soybean plants produced by introducing A1aB1bM3 to the seed storage protein-deficient variety were prepared.

Further, 8 individuals of transformants produced by introducing A2PA1aB1bM 1, 33 individuals of transformants produced by introducing A2PA1aB1bM3, 32 individuals of transformants produced by introducing A2PA1aB1bM5, and 9 individuals of transformants produced by introducing A2PRP10M1, to the seed storage protein-deficient variety were prepared.

These plant bodies of transformed soybean were acclimatized to ambient humidity, and the cultivation was continued under the conditions of 10000 1× and illumination for 16 hours per day, after which seeds were harvested from all the individuals. By such a process, seeds of the transformed soybean plants of the $T_1$ generation were obtained.

Example 7

Evaluation of Amount of Aβ4-10 Accumulated in Seeds of Transformed Soybean

Total protein was extracted from the seeds of the transformed soybeans obtained in the above Example 6, and the accumulated amount of Aβ4-10 was evaluated by Western blotting using an antibody specific to Aβ4-10. For lines having large accumulated amounts, quantitative analysis was carried out.

1) Amount of Accumulation of Aβ4-10 Expressed as Modified A1aB1b

20 μg of total protein extracted from seeds of each transformed soybean was separated by SDS-PAGE, and allowed to react with an antibody specific to Aβ4-10, followed by detection using ECL Advance Western Blotting Detection Kit (manufactured by GE Healthcare Bio-Science KK). A chemiluminescence image was captured by LAS4000miniPR (manufactured by FUJIFILM Corporation), and quantitative analysis was carried out using MultiGage, which is an analysis software included in the apparatus. As a standard sample for quantification, a His-Tag-linked recombinant protein A1aB1bM1 prepared by the *E. coli* expression system was used.

As a result, the signal band corresponding to Aβ4-10 was confirmed for each line of the transformed soybean seeds obtained in the above Example 6, so that accumulation of Aβ4-10 was confirmed. Among the lines, the transformed soybean seeds prepared by introducing A1aB1bM1, A1aB1bM3 and A1aB1bM5 to the Jack variety (lines No. 10-2, No. a-2 and No. 6-6) and the transformed soybean seeds prepared by introducing A1aB1bM1 to the seed storage protein-deficient variety (line No. 16-2), in which Aβ4-10 was highly accumulated, were subjected to measurement of the amounts of accumulation of Aβ4-10. The results are shown in Table 3.

TABLE 3

| Modified gene | Variety | Line No. | Amount of accumulated Aβ4-10 (μg/1 g seed weight) |
|---|---|---|---|
| A1aB1bM1 | Jack | 10-2 | 35 |
| A1aB1bM1 | Deficient variety | 16-2 | 870 |
| A1aB1bM3 | Jack | a-2 | 42 |
| A1aB1bM5 | Jack | 6-6 | 108 |

Figure 4:
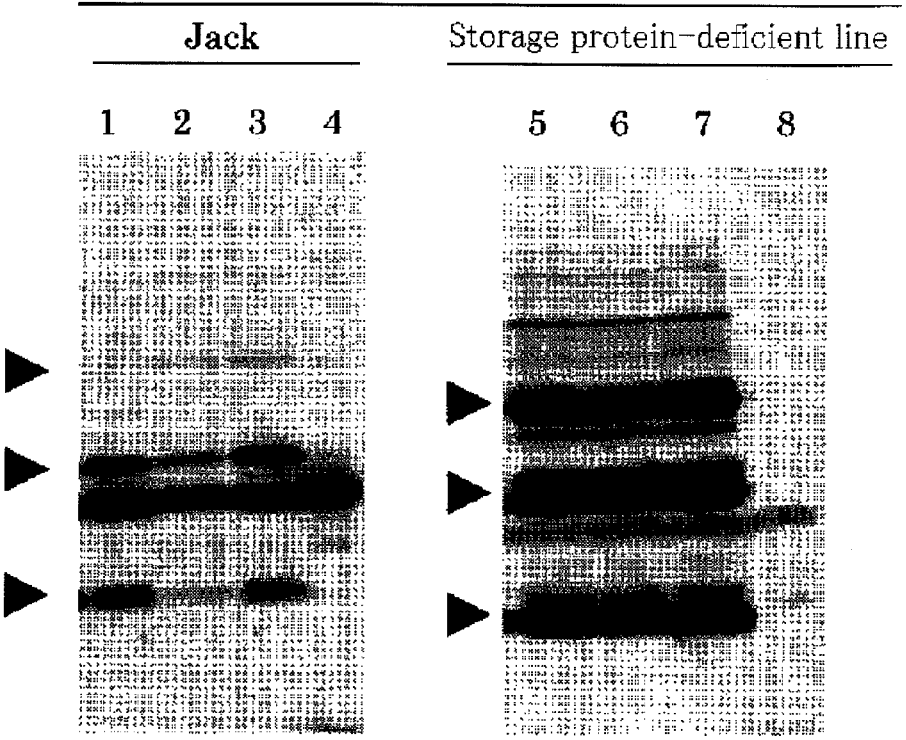

Further, comparison of the accumulated amounts of the modified seed storage protein in the transformed soybeans prepared by introducing A1aB1bM1 (the gene in which three copies of Aβ4-10 are inserted) to the Jack variety and to the seed storage protein-deficient variety was carried out by Western blot analysis. The results are shown in FIG. 4 (wherein the arrowheads indicate the bands corresponding to the modified seed storage proteins). As a result, it was confirmed that the amounts of accumulation of the modified seed storage protein in the transformant line 10-2 prepared by introducing A1aB1bM1 to the Jack variety (seed Nos. 1 to 3) were about 0.1 to 0.2% with respect to the total protein in the seeds, while the amounts of accumulation of the modified seed storage protein in the transformant line 16-2 prepared by introducing A1aB1bM1 to the seed storage protein-deficient line (seed Nos. 1 to 3) were about 1 to 2% with respect to the total protein in the seeds, which values were about 10 times higher than those in the above case.

Further, the accumulated amount of the modified seed storage protein in the transformed soybeans prepared by introducing A1aB1bM3 (the gene in which a single copy of Aβ4-10 is inserted) to the seed storage protein-deficient variety was measured by Western blot analysis. The results are shown in Table 4.

TABLE 4

| Modified gene | Variety | Line No. | Amount of accumulated Aβ4-10 (μg/1 g seed weight) |
|---|---|---|---|
| A1aB1bM3 | Deficient variety | 5-2 | 1568 |
|  |  | 5-6 | 2504 |
|  |  | 7-3 | 2348 |

2) Amount of Accumulation of Aβ4-10 Expressed as Modified Arcelin

Figure 5:
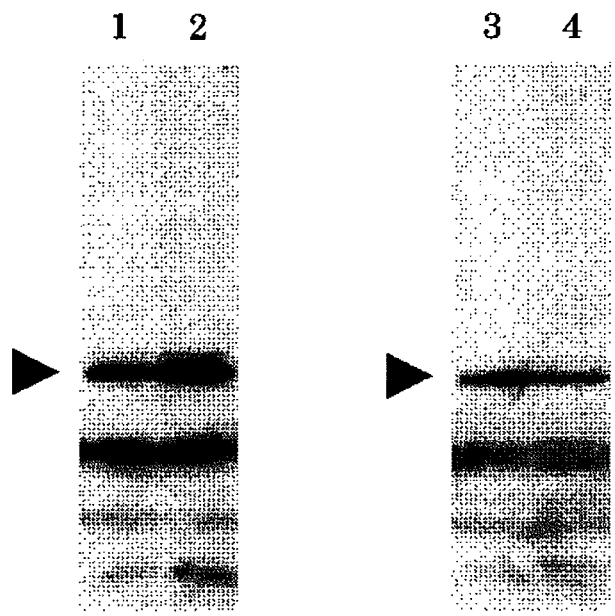

20 μg of total protein extracted from seeds of each transformed soybean was separated by SDS-PAGE, and allowed to react with an antibody specific to Aβ4-10, followed by Western blot detection of Aβ4-10 using ECL Advance Western Blotting Detection Kit (manufactured by GE Healthcare Bio-Science KK). As a result, the signal bands corresponding to the Aβ4-10 peptide was confirmed for the transformed soybean seeds to which Arc5M1 was introduced (line 2-1) and the transformed soybean seeds to which Arc5M2 was introduced (line 2-2), so that accumulation of Aβ4-10 was confirmed (FIG. 5).

3) Amount of Accumulation of Aβ4-10 Expressed as Modified Prolamin

Figure 6:
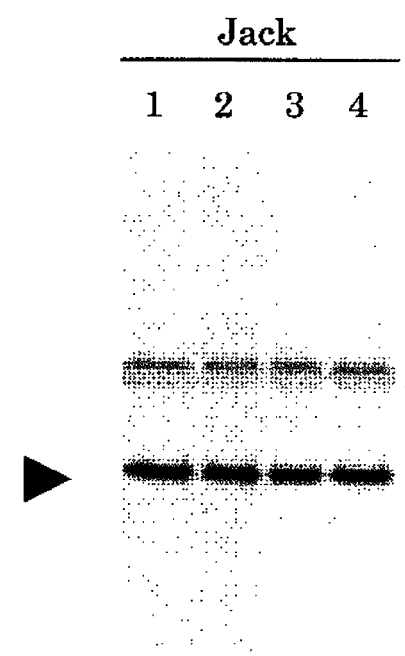

20 μg of total protein extracted from seeds of the RP10M1-transformed soybean (lines 1-1 and 4-2) was separated by SDS-PAGE, and allowed to react with an antibody against Aβ4-10, followed by Western blot detection using ECL Advance Western Blotting Detection Kit (manufactured by GE Healthcare Bio-Science KK). As a result, the signal bands corresponding to the Aβ4-10 peptide was confirmed for the transformed soybean seeds of the respective lines to which PR10M1 was introduced, so that accumulation of the Aβ4-10 peptide was confirmed (FIG. 6).

Similarly, the signal bands corresponding to the Aβ4-10 peptide was confirmed for the seeds of the RP10M1-transformed soybean, so that accumulation of Aβ4-10 was confirmed. The accumulated amount in this case was about 380 μg/g seed for the No. 1-1 line.

4) Amount of Accumulation of Aβ4-10 Expressed as Modified A1aB1b by Arcelin 2 Promoter 20 μg of total protein extracted from seeds of each transformed soybean was separated by SDS-PAGE, and subjected to the detection in the same manner as in 1) in Example 7.

As a result, the signal bands corresponding to Aβ4-10 was confirmed for the respective lines of transformed soybean seeds obtained in the above Example 6, so that accumulation of Aβ4-10 was confirmed (FIG. 7).

Further, it was confirmed that the amount of accumulation of Aβ4-10 in the transformed soybean seeds prepared by introduction of the gene into the seed storage protein-deficient variety, which amount of accumulation was assumed based on the intensity of the signal band, for A2PA1aB1bM1 (line 4-6) was almost equivalent to that for A1aB1bM1 (line 7-1), and that these amounts of accumulation were clearly larger than those for A1aB1bM1 (line 8-1) prepared by introduction of the gene into the Jack variety (FIG. 7).

Example 8

Assay of Effect of Modified Seed Storage Protein

A1aB1bM1 prepared in the above Example 1 was expressed in *E. coli* by the known method, to produce the protein.

In order to obtain the recombinant protein encoded by A1aB1bM1, the *E. coli* expression plasmid pETA1aB1bM1 was prepared by ligating A1aB1bM1 with the pET21-d vector (manufactured by Novagen).

The above-described pETA1aB1bM1 was introduced to *E. coli* AD494 (manufactured by Novagen) by a conventional method, and the recombinant *E. coli* was cultured in 50 ml of the known TB medium (supplemented with kanamycin at a final concentration of 15 mg/l and carbenicillin at a final concentration of 50 mg/l) at 37° C. for 18 hours, followed by adding 10 ml of the culture to 1000 ml of the known LB medium (supplemented with kanamycin at a final concentration of 15 mg/l, carbenicillin at a final concentration of 50 mg/l and sodium chloride at a final concentration of 500 mM) as a production medium and carrying out culture at 37° C. for 2 hours. Thereafter, IPTG was added to a final concentration of 1 mM, and the recombinant *E. coli* was then cultured at 20° C. for 48 hours. The cells of *E. coli* after the culture were collected by centrifugation at 8000 rpm for 15 minutes. From the bacterial cells after the collection, the fraction of soluble protein was extracted using BugBuster Protein Extraction Reagent (manufactured by Novagen). From the obtained fraction of soluble protein, the recombinant protein encoded by A1aB1bM1 (A1aB1bM1 protein) was purified using Ni-NTA His-Bind Resins (manufactured by Novagen).

In physiological saline, 50 μg of A1aB1bM1 having the β-amyloid antigenic determinant (Aβ4-10) was dissolved, and the resulting solution was administered to Alzheimer's disease model mice (TgCRND8) of 4-weeks old five times at intervals of 1 week by subcutaneous injection (3 individuals/group). A control group was prepared by expressing the unmodified gene encoding the wild-type A1aB1b in *E. coli* in the same manner as described above, and administering the obtained wild-type A1aB1b to the mice. Nine weeks after the administration, blood was collected from the mice, and production of antibodies against Aβ4-10 was confirmed by the known sandwich method by ELISA. The antibody titer was evidently higher in the group to which the A1aB1bM1 protein was administered compared to the group to which the A1aB1b protein was administered, so that the vaccine effect of the recombinant protein encoded by A1aB1bM1 was confirmed.

Example 9

Thermal Stability of Modified Seed Storage Protein in Soybean Seeds

The transformed soybean seeds obtained in the above Example 6 were subjected to various heat treatments to test the thermal stability of the modified seed storage protein in the seeds.

1) Roasted Group of Transformed Soybean Seeds

The A1aB1bM3-transformed soybean seeds were pulverized, and 10 mg of the pulverized product was processed in an autoclave sterilization equipment at 100° C. for 10 minutes, followed by extracting total protein by the method described in the above Example 7 and evaluating the amount of accumulation of Aβ4-10 in the seeds by Western blotting using an antibody specific to Aβ4-10.

2) Water-Boiled Group of Transformed Soybean Seeds

The A1aB1bM3-transformed soybean seeds were pulverized, and 30 μl of distilled water was added to 10 mg of the pulverized product, and the resultant was processed in an autoclave sterilization equipment at 100° C. for 10 minutes, followed by extracting total protein by the method described in the above Example 7 and evaluating the amount of accumulation of Aβ4-10 in the seeds by Western blotting using an antibody specific to Aβ4-10.

3) Group in which Extract from Transformed Soybean Seeds was Heat-Treated

The A1aB1bM3-transformed soybean seeds were pulverized, and total protein was extracted by the method described in the above Example 7, followed by processing the total protein in an autoclave sterilization equipment at 100° C. for 10 minutes. Thereafter, the amount of accumulation of Aβ4-10 in the seeds was evaluated by Western blotting using an antibody specific to Aβ4-10.

As a result, the signal bands corresponding to Aβ4-10 was confirmed in the roasted group and the water-boiled group. It was confirmed that the amounts were equivalent to that in the heat-untreated group, and hence that the modified seed storage protein in the seeds is heat-stable (FIG. 8).

Example 10

Form of (β-Amyloid Antigenic Determinant

The peptide having the amino acid sequence of Aβ-10 (P1), the peptide having the amino acid sequence wherein two copies of P1 are tandemly linked (P2), and the peptide having the amino acid sequence wherein three copies of P1 are tandemly linked (P3) were synthesized using a custom peptide synthesis service.

```
P1: FRHDSGY                    (SEQ ID NO: 3)

P2: FRHDSGY FRHDSGY            (SEQ ID NO: 60)

P3: FRHDSGY FRHDSGY FRHDSGY    (SEQ ID NO: 61)
```

Subsequently, KLH-P1, KLH-P2 and KLH-P3, wherein a carrier protein key-limpet-hemocyanin (KLH, Mw. 1000000)

is linked to the N-termini of the peptides P1, P2 and P3, respectively, through cysteine (Cys) as a cross-linker, were prepared.

In physiological saline, 50 μg each of these KLH-P1, KLH-P2 and KLH-P3 was dissolved, and the resulting solution was administered to mice (BALBc) of 4-weeks old five times at intervals of 1 week by subcutaneous injection (3 individuals/group). Nine weeks after the administration, blood was collected from the mice to collect antiserum. The obtained antiserum was affinity-purified to prepare purified antibodies against KLH-P1, KLH-P2 and KLH-P3.

Commercially available synthetic Aβ42 in amounts of 400 and 1000 picomoles was subjected to electrophoresis by SDS-PAGE, and the above-described purified antibodies against KLH-P1, KLH-P2 and KLH-P3 were allowed to react with the Aβ42, followed by detection using ECL Advance Western Blotting Detection Kit (manufactured by GE Healthcare Bio-Science KK). The chemiluminescence image was captured by LAS4000miniPR (manufactured by FUJIFILM Corporation), and the signal intensities were compared to assume the binding capacities of the antibodies to Aβ42. As a result, it was shown that the signal intensity for KLH-P2 was evidently stronger than the signal intensities for KLH-P1 and KLH-P3, and hence that a specific antibody having a high antibody titer against Aβ can be obtained by tandemly linking two copies of the peptide having the amino acid sequence of Aβ4-10 (FIG. 9).

Industrial Applicability

Since, by the present invention, it is possible to produce and accumulate an Alzheimer's disease vaccine in soybean seeds as a fusion protein with a seed storage protein such as soybean 11S globulin or 7S globulin, common bean arcelin, or rice prolamin, a large amount of the Alzheimer's disease vaccine can be produced and supplied for prophylaxis and therapy of Alzheimer's disease.

What is claimed is:

1. A transformed soybean plant comprising a gene encoding a modified seed storage protein, wherein said gene encoding the modified seed storage protein comprises a gene encoding an Alzheimer's disease vaccine inserted into one or more variable region(s) of a gene encoding a wild-type seed storage protein such that frameshift does not occur, and wherein said modified seed storage protein is expressed an accumulates in a seed, wherein said Alzheimer's disease vaccine is a β-amyloid antigenic determinant, and wherein said wild-type seed storage protein is an A1aB1b subunit of soybean 11S globulin which comprises the amino acid sequence shown in SEQ ID NO:2 or an amino acid sequence having an identity of not less than 90% to the amino acid sequence shown in SEQ ID NO:2, and wherein at least one of the variable regions encodes amino acid positions 198-216 in wild-type SEQ ID NO:2 prior to said modification.

2. The transformed soybean plant according to claim 1, wherein said β-amyloid antigenic determinant comprises a sequence having one to three copies of the peptide comprising the sequence shown in SEQ ID NO:3 which are linked to each other.

3. The transformed soybean plant according to claim 1, wherein endogenous soybean 11S globulin and/or soybean 7S globulin is/are deficient.

4. The transformed soybean plant according to claim 1, wherein said β-amyloid antigenic determinant is inserted into additional variable regions, wherein said variable regions encode amino acid positions 111-128 and/or amino acid positions 268-315 in wild-type SEQ ID NO:2 prior to said modification.

5. The transformed soybean plant according to claim 1, wherein expression of said gene encoding a modified seed storage protein is regulated by a promoter of a common bean arcelin 2 gene or a promoter of an A1aB1b subunit of soybean 11S globulin gene.

6. A seed of the transformed soybean plant according to claim 1.

7. A method for producing an Alzheimer's disease vaccine using the transformed soybean plant according to claim 1, wherein said Alzheimer's disease vaccine is produced in a seed of said transformed soybean plant.

8. A vector comprising:

a promoter which induces soybean seed-specific expression; and a gene encoding a modified seed storage protein linked downstream of said promoter, wherein said gene encoding the modified seed storage protein comprises an A1lab1b subunit of soybean 11S globulin which comprises the amino acid sequence shown in SEQ ID NO:2 or an amino acid sequence having an identity of not less than 90% to the amino acid sequence shown in SEQ ID NO:2 , wherein the A1aB1b subunit comprises an insertion of a gene encoding a β-amyloid antigenic determinant into at least one variable regions, and wherein at least one of the variable region(s) encodes amino acid positions 198-216 in wild-type SEQ ID NO:2 prior to said modification such that frameshift does not occur.

9. The vector according to claim 8, wherein said promoter is a promoter of a common bean arcelin 2 gene or a promoter of an A1aB1b subunit of soybean 11S globulin gene.

10. The transformed soybean plant according to claim 2, wherein endogenous soybean 11S globulin and/or soybean 7S globulin is/are deficient.

11. The transformed soybean plant according to claim 2, wherein said β-amyloid antigenic determinant is inserted into additional variable regions, wherein said variable regions encode amino acid positions 111-128and/or amino acid positions 268-315 in wild-type SEQ ID NO:2 prior to said modification.

12. The transformed soybean plant according to claim 3, wherein said β-amyloid antigenic determinant is inserted into additional variable regions, wherein said variable regions encode amino acid positions 111-128 and/or amino acid positions 268-315 in wild-type SEQ ID NO:2 prior to said modification.

13. The transformed soybean plant according to claim 2, wherein expression of said gene encoding a modified seed storage protein is regulated by a promoter of a common bean arcelin 2 gene or a promoter of an A1aB1b subunit of soybean 11S globulin gene.

14. The transformed soybean plant according to claim 3, wherein expression of said gene encoding a modified seed storage protein is regulated by a promoter of a common bean arcelin 2 gene or a promoter of an A1aB1b subunit of soybean 11S globulin gene.

15. The transformed soybean plant according to claim 4, wherein expression of said gene encoding a modified seed storage protein is regulated by a promoter of a common bean arcelin 2 gene or a promoter of an A1aB1b subunit of soybean 11S globulin gene.

16. A seed of the transformed soybean plant according to claim 2.

17. A seed of the transformed soybean plant according to claim 3.

18. A seed of the transformed soybean plant according to claim 4.

19. A seed of the transformed soybean plant according to claim 5.

20. A method for producing an Alzheimer's disease vaccine using the transformed soybean plant according to claim 2, wherein said Alzheimer's disease vaccine is produced in a seed of said transformed soybean plant.

21. A method for producing an Alzheimer's disease vaccine using the transformed soybean plant according to claim 3, wherein said Alzheimer's disease vaccine is produced in a seed of said transformed soybean plant.

22. A method for producing an Alzheimer's disease vaccine using the transformed soybean plant according to claim 4, wherein said Alzheimer's disease vaccine is produced in a seed of said transformed soybean plant.

23. A method for producing an Alzheimer's disease vaccine using the transformed soybean plant according to claim 5, wherein said Alzheimer's disease vaccine is produced in a seed of said transformed soybean plant.

24. The transformed soybean plant according to claim 10, wherein expression of said gene encoding a modified seed storage protein is regulated by a promoter of a common bean arcelin 2 gene or a promoter of an A1aB1b subunit of soybean 11S globulin gene.

25. The transformed soybean plant according to claim 19, wherein expression of said gene encoding a modified seed storage protein is regulated by a promoter of a common bean arcelin 2 gene or a promoter of an A1aB1b subunit of soybean 11S globulin gene.

26. The transformed soybean plant according to claim 20, wherein expression of said gene encoding a modified seed storage protein is regulated by a promoter of a common bean arcelin 2 gene or a promoter of an A1aB1b subunit of soybean 11S globulin gene.

27. A seed of the transformed soybean plant according to claim 10.

28. A seed of the transformed soybean plant according to claim 11.

29. A seed of the transformed soybean plant according to claim 12.

30. A seed of the transformed soybean plant according to claim 13.

31. A seed of the transformed soybean plant according to claim 14.

32. A seed of the transformed soybean plant according to claim 15.

33. A seed of the transformed soybean plant according to claim 24.

34. A seed of the transformed soybean plant according to claim 25.

35. A seed of the transformed soybean plant according to claim 26.

36. A method for producing an Alzheimer's disease vaccine using the transformed soybean plant according to claim 1, which Alzheimer's disease vaccine is produced in a seed of said transformed soybean plant.

* * * * *

UNITED STATES PATENT AND TRADEMARK OFFICE
CERTIFICATE OF CORRECTION

PATENT NO. : 8,937,218 B2  
APPLICATION NO. : 13/130465  
DATED : January 20, 2015  
INVENTOR(S) : Teruhiko Terakawa et al.

Page 1 of 1

It is certified that error appears in the above-identified patent and that said Letters Patent is hereby corrected as shown below:

In the Drawings

Sheet 2 of 5 (FIG. 2) at line 8, Change "PCRAmplification" to --PCR Amplification--.

In the Specification

In column 5 at line 29, Change "o f" to --of--.

In column 17 at lines 3-4, Change "a of" to --of--.

In column 23 at line 17, Change "A2PA1aB1bM 1," to --A2PA1aB1bM1,--.

In column 24 at line 21, Change "A1aB1bM1" to --A1aB1M1--.

In column 24 at line 25, Change "A1aB1bM1" to --A1aB1M1--.

In the Claims

In column 93 at line 26, In Claim 1, change "an" to --and--.

In column 93 at line 67, In Claim 8, change "A1laB1b" to --A1aB1b--.

In column 94 at line 38, In Claim 19, change "111-128and/or" to --111-128 and/or--.

In column 95 at line 24, In Claim 25, change "claim 19," to --claim 11,--.

In column 96 at line 1, In Claim 26, change "claim 20," to --claim 12,--.

In column 96 at lines 25-26, In Claim 36, change "claim 1," to --claim 10,--.

Signed and Sealed this  
First Day of December, 2015

Michelle K. Lee  
*Director of the United States Patent and Trademark Office*